United States Patent
Thibonnier

(10) Patent No.: US 12,286,625 B2
(45) Date of Patent: *Apr. 29, 2025

(54) INHIBITION OF MIR-22 miRNA BY APT-110

(71) Applicant: AptamiR Therapeutics, Inc., Naples, FL (US)

(72) Inventor: Marc Thibonnier, Naples, FL (US)

(73) Assignee: APTAMIR THERAPEUTICS, INC., Naples, FL (US)

( * ) Notice: Subject to any disclaimer, the term of this patent is extended or adjusted under 35 U.S.C. 154(b) by 170 days.

This patent is subject to a terminal disclaimer.

(21) Appl. No.: 16/947,905

(22) Filed: Aug. 24, 2020

(65) Prior Publication Data

US 2021/0079392 A1 Mar. 18, 2021

Related U.S. Application Data

(63) Continuation of application No. 16/097,012, filed as application No. PCT/IB2017/052505 on Apr. 28, 2017, now abandoned.

(60) Provisional application No. 62/329,537, filed on Apr. 29, 2016.

(51) Int. Cl.
| | |
|---|---|
| *C12N 15/113* | (2010.01) |
| *A61K 9/127* | (2025.01) |
| *A61K 31/202* | (2006.01) |
| *A61K 31/7125* | (2006.01) |
| *A61K 47/14* | (2017.01) |
| *A61K 47/66* | (2017.01) |
| *A61K 47/69* | (2017.01) |
| *A61P 3/04* | (2006.01) |

(52) U.S. Cl.
CPC ............ *C12N 15/113* (2013.01); *A61K 9/127* (2013.01); *A61K 31/202* (2013.01); *A61K 31/7125* (2013.01); *A61K 47/14* (2013.01); *A61K 47/66* (2017.08); *A61K 47/6917* (2017.08); *A61P 3/04* (2018.01); *C12N 2310/113* (2013.01); *C12N 2310/321* (2013.01); *C12N 2310/3341* (2013.01)

(58) Field of Classification Search
CPC ............ C12N 15/113; C12N 2310/113; C12N 2310/321; C12N 2310/3341; C12N 2310/315; C12N 2310/3231; C12N 2310/346; A61K 31/202; A61K 31/7125
See application file for complete search history.

(56) References Cited

U.S. PATENT DOCUMENTS

| | | |
|---|---|---|
| 5,013,830 A | 5/1991 | Ohtsuka et al. |
| 5,149,797 A | 9/1992 | Pederson et al. |
| 5,220,007 A | 6/1993 | Pederson et al. |
| 5,256,775 A | 10/1993 | Froehler |

(Continued)

FOREIGN PATENT DOCUMENTS

| | | |
|---|---|---|
| EP | 1800695 A1 | 6/2007 |
| WO | WO 1993/007883 | 4/1993 |

(Continued)

OTHER PUBLICATIONS

Stenvang et al.(Silence 2012, 3:1, 17 pages) (Year: 2012).*

(Continued)

*Primary Examiner* — Richard A Schnizer
(74) *Attorney, Agent, or Firm* — Norton Rose Fulbright US LLP

(57) ABSTRACT

Increase of energy expenditure as an effective treatment of obesity and related disorders is a target for drug research and development. A 15% increase of energy expenditure is believed to be sufficient to achieve significant weight and fat mass reduction while providing meaningful improvement of metabolic parameters. Disclosed herein is a method for pharmacological inhibition of miR-22-3p, which represents a new therapeutic approach for treating human obesity, diabetes, and hypercholesterolemia.

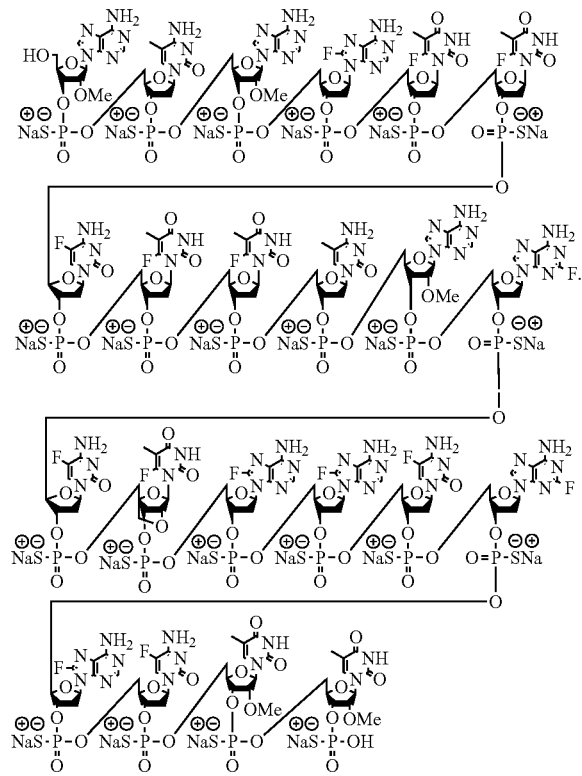

16 Claims, 38 Drawing Sheets

Specification includes a Sequence Listing.

(56) References Cited

U.S. PATENT DOCUMENTS

| | | |
|---|---|---|
| 5,294,542 A | 3/1994 | Sioma et al. |
| 5,366,878 A | 11/1994 | Pederson et al. |
| 5,403,711 A | 4/1995 | Walder et al. |
| 5,491,133 A | 2/1996 | Walder et al. |
| 5,539,082 A | 7/1996 | Nielsen et al. |
| 5,565,350 A | 10/1996 | Kmiec |
| 5,623,065 A | 4/1997 | Cook et al. |
| 5,652,355 A | 7/1997 | Metelev et al. |
| 5,652,356 A | 7/1997 | Agrawal |
| 5,700,922 A | 12/1997 | Cook |
| 5,714,331 A | 2/1998 | Buchardt et al. |
| 5,716,928 A | 2/1998 | Benet et al. |
| 5,719,262 A | 2/1998 | Buchardt et al. |
| 5,858,401 A | 1/1999 | Bhalani et al. |
| 6,107,094 A | 8/2000 | Crooke |
| 6,180,767 B1 | 1/2001 | Wickstrom et al. |
| 6,350,853 B1 | 2/2002 | Nielsen et al. |
| 7,759,318 B1 | 7/2010 | Perera et al. |
| 9,034,839 B2 | 5/2015 | Thibonnier |
| 9,453,224 B2 * | 9/2016 | Thibonnier ........... C12Q 1/6883 |
| 9,803,203 B2 * | 10/2017 | Thibonnier ........... C12N 15/115 |
| 10,253,319 B2 * | 4/2019 | Thibonnier ............... C12Q 1/68 |
| 11,690,804 B2 * | 7/2023 | Thibonnier ............. A61K 31/12 |
| | | 424/450 |
| 2004/0028670 A1 | 2/2004 | Carlson et al. |
| 2005/0191294 A1 | 9/2005 | Arap et al. |
| 2005/0203041 A1 | 9/2005 | Mourich et al. |
| 2005/0261218 A1 | 11/2005 | Esau et al. |
| 2007/0123482 A1 | 5/2007 | Stoffel |
| 2008/0311040 A1 | 12/2008 | Berry et al. |
| 2009/0291049 A1 | 11/2009 | Nuno Sereno De Almeida Moreira et al. |
| 2009/0291907 A1 | 11/2009 | Esau et al. |
| 2010/0063131 A1 | 3/2010 | Takeuchi et al. |
| 2010/0255545 A1 | 10/2010 | Smolke et al. |
| 2010/0266491 A1 | 10/2010 | Farokhzad et al. |
| 2010/0298410 A1 | 11/2010 | Obad et al. |
| 2011/0014118 A1 | 1/2011 | Tamarkin et al. |
| 2011/0038923 A1 | 2/2011 | Weisinger et al. |
| 2011/0224286 A1 | 9/2011 | Yu et al. |
| 2013/0159091 A1 | 6/2013 | Harper |
| 2013/0331440 A1 | 12/2013 | Scheideler et al. |
| 2013/0344135 A1 | 12/2013 | Van Rooij et al. |
| 2015/0111949 A1 | 4/2015 | Pandolfi et al. |
| 2015/0133521 A1 * | 5/2015 | Bloch ..................... A61K 45/06 |
| | | 536/24.5 |
| 2015/0216802 A1 | 8/2015 | Leroux et al. |
| 2016/0375113 A1 | 12/2016 | Narain et al. |
| 2018/0208927 A1 | 7/2018 | Jadhav et al. |

FOREIGN PATENT DOCUMENTS

| | | |
|---|---|---|
| WO | WO 2010/108126 | 9/2010 |
| WO | WO 2010/135714 | 11/2010 |
| WO | WO 2010/144485 | 12/2010 |
| WO | WO 2011/039729 | 4/2011 |
| WO | WO 2011/079263 | 6/2011 |
| WO | WO 2011/138457 | 11/2011 |
| WO | WO 2011/153542 | 12/2011 |
| WO | WO 2012/007725 | 1/2012 |
| WO | WO 2012/080459 | 6/2012 |
| WO | WO 2012/083005 | 6/2012 |
| WO | WO 2012/148952 | 11/2012 |
| WO | WO 2013/159091 | 10/2013 |
| WO | WO 2013/181613 | 12/2013 |
| WO | WO 2013/192576 | 12/2013 |
| WO | WO 2017/187426 | 11/2017 |

OTHER PUBLICATIONS

Abente, et al., MicroRNAs in Obesity-Associated Disorders, *Archives of Biochemistry and Biophysics*, 589(1); 589; 109-119, 2016.

Abumrad, et al., Cloning a Rat Adipocyte Membrane Protein Implicated in Binding or Transport of Long-Chain Fatty Acids That is Induced During Preadipocyte Differentiation, *JBC*, 268; 17665-17668, 1993.

Accardo, Antonella and Giancarlo Morelli, "Peptide-Targeted Liposomes for Selective Drug Delivery: Advantages and Problematic Issues" Peptide Science 2015, 104(5), 462-479.

Alexander, et al., "MicroRNAs in Adipogenesis and as Therapeutic Targets for Obesity," *Expert Opinion on Therapeutic Targets*, 15(5):623-36, 2011.

Allen et al., "Liposomes with prolonged circulation times: factors affecting uptake by reticuloendothelial and other tissues" *Biochim. Biophys. Acta* 1989, 981(1), 27-35.

Andersen, et al., "The Frequent UCP2 -866G> APolymorphism Protects Against Insulin Resistance and is Associated with Obesity: A Study of Obesity and Related Metabolic Traits Among 17 636 Danes," *International Journal of Obesity*, 37(2); 175-81, 2013.

Bader, et al., "Developing Therapeutic MicroRNAs for Cancer," *Gene Therapy*. 18(12);1121-26, 2011.

Banigan, et al., "Differential Expression of Exosomal MicroRNAS in Prefrontal Cortices of Schizophrenia and Bipolar Disorder Patients," *PLOS One*, 8(1); e48814 (1-18), 2013.

Borgdorff, et al., "Multiple MicroRNAs Rescue from Ras-Induced Senescence by Inhibiting P21," *Oncogene*, 29(15);2262-2271, 2010.

Broderick, et al., "MicroRNA Therapeutics," *Gene Therapy*, 18(12);1104-1110, 2011.

Cao, et al., "White to Brown Fat Phenotypic Switch Induced by Genetic and Environmental Activation of a Hypothalamic-Adipocyte Axis", *Cell Metabolism* 14; 324-338, 2011.

Ceppi, et al., "MicroRNA-155 Modulates the Interleukin-1 Signaling Pathway in Activated Human Monocyte-Derived Dendritic Cells," *PNAS*, 106(8); 2735-2740, 2009.

Cerchia, et al., "Coupling Aptameters to Short Interfering RNAs as Therapeutics," *Pharmaceuticals*, 4(12); 1434-1449, 2011.

Chen, et al., " In Vitro Evidence Suggests that MiR-133a-Mediated Regulation of Uncoupling Protein 2 (UCP2) is an Indispensable Step in Myogenic Differentiation," *The Journal of Biological Chemistry*, 284; 5362-5369, 2009.

Chen, et al., "In Vitro Evidence Suggests That MIR-133a-Mediated Regulation of Uncoupling Protein 2 (UCP2) is an Indispensable Step in Myogenic Differentiation," *Journal of Biological Chemistry*, 284(8); 5362-5369, 2009.

Chen, et al., "MicroRNA-22 Can Reduce Parathymosin Expression in Transdifferentiated Hepatocytes," *PLoS One* 7(4); e34116, 2012.

Chen, et al., "Nanoparticles Modified with Tumor-Targeting ScFv Deliver SiRNA and MiRNA for Cancer Therapy," *Mol Therapy*, 18; 1650-1656, 2010.

Czech, et al., "RNAi-Based Therapeutic Strategies for Metabolic Disease," *Nature Reviews Endocrinology*, 7(8);473-84, 2011.

Davidson, et al., "Current Prospects for RNA Interference-Based Therapies," *Nature Reviews Genetics*, 12(5);329-340, 2011.

Dawson et al., "Three Distinct D-Amino Acid Substitutions Confer Potent Antiangiogenic Activity on an Inactive Peptide Derived from Thrombospondin-1 Type 1 Repeat" *Molecular Pharmacology* 1999, 55, 332-338.

Dehwah, et al., "MicroRNAs and Type 2 Diabetes/Obesity," *Journal of Genetics and Genomics*, 39(1); 11-18, 2011.

Ebert, et al., "MicroRNA Sponges: Competitive Inhibitors of Small RNAs in Mammalian Cells," *Nature Methods*, 4(9); 721-726, 2007.

Elmen, et al., "LNA-Mediated MicroRNA Siliencing in Non-Human Primates," *Nature*, 452;896-99, 2008.

Esau, et al., "MIR-122 Regulation of Lipid Metabolism Revealed by In Vivo Antisense Targeting," *Cell Metabolism*, 3(2); 87-98, 2006.

Esterbauer, et al., "A Common Polymorphism in the Promoter of UCP2 is Associated with the Decreased Risk of Obesity in Middle-Aged Humans," *Nature Genetics*, 28(2); 178-83, 2001.

Extended European Search Report Issued in Corresponding European Patent Application No. 17788937.5, dated Dec. 2, 2019.

Ferrante, et al., "Adipocyte-Derived Exosomal MiRNAs: A Novel Mechanism for Obesity-Related Disease," *Pediatric Research*, 77(3); 447-454, 2015.

(56) References Cited

OTHER PUBLICATIONS

Friedman, et al., "MiRror: A Combinatorial Analysis Took for Ensembles of MicroRNAs and their Targets," *BMC Bioinformatics*, 26(15); 1920-1921, 2010.
Fujiki, et al., "Expression of the Peroxisome Proliferator Activated Receptor y Gene is Repressed by DNA Methylation in Visceral Adipose Tissue of Mouse Models of Diabetes," *BMC Biology*, 7(38); 1-14, 2009.
Gallagher, et al., "Integration of MicroRNA Changes In Vivo Identifies Novel Molecular Features of Muscle Insulin Resistance in Type 2 Diabetes," *Genome Medicine*, 2(2), 1-18, 2010.
Hajer, et al., "Adipose Tissue Dysfunction in Obesity, Diabetes, and Vascular Diseases," *European Heart Journal* 29; 2959-2971, 2008.
Hao, et al., "Inhibitors Targeting on Cell Wall Biosynthesis Pathway of MRSA," *Molecular BioSystems*, 8(11); 2828-2838, 2012.
Hao, et al., "The Reconstruction and Analysis of Tissue Specific Human Metabolic Networks," *Molecular BioSystems*, 8(2);663-670, 2012.
He, et al., "The Emerging Roles of Fatty Acid Translocase/CD36 and the Aryl Hydrocarbon Receptor in Fatty Liver Disease," *Experimental Biology and Medicine*, 236; 1116-1121, 2011.
Ho, et al., "Mitochondrial Uncoupling Protein-2 (UCP2) Mediates Leptin Protection Against MPP+ Toxicity in Neuronal Cells", *Neurotoxicity Research*, 17; 332-343, 2010.
Hsu, et al., "MiRTarBase: A Database Curates Experimentally Validated MicroRNA-Target Interactions," *Nucleic Acids Research*, 39 (Database Issue); D163-169, 2011.
International Search Report and Written Opinion in PCT Application No. PCT/US2013/053613 mailed, Jan. 2, 2014.
International Search Report and Written Opinion Issued in Corresponding PCT Application No. PCT/IB2017/052505, mailed Oct. 6, 2017.
International Search Report and Written Opinion Issued in Corresponding PCT Application No. PCT/US2013/037579, mailed Oct. 25, 2013.
Jimenez-Mateos, et al., "microRNA Targeting of the P2x7 Purinoceptor Opposes a Contralateral Epileptogenic Focus in the Hippocampus," Scientific Reports, 5(1): 2015.
Kanasaki, et al., "Biology of Obesity: Lessons from Animal Models of Obesity," *Journal of Biomedicine and Biotechnology*; Article 197636, 2011.
Kanwar, et al., "Chimeric Aptamers in Cancer Cell-Targeted Drug Delivery," *Critical Reviews in Biochemistry and Molecular Biology*, 46(6); 459-77, 2011.
Kaur, et al., "Comprehensive MiRNome and In Silico Analyses Identify the Wnt Signaling Pathway to be Altered in the Diabetic Liver," *Molecular BioSystems*, 7;3234-3244, 2011.
Kaur, et al., "Elevated Hepatic miR-22-3p Expression Impairs Gluconeogenesis by Silencing the Wnt-Responsive Transcription Factor Tcf7," Diabetes, 64(11): 3659-3669, 2015.
Kim, et al., "Molecular Imaging of a Cancer-Targeting Theragnostics Probe Using a Nucleolin Aptamer- and MicroRNA-221 Molecular Beacon-Conjugated Nanoparticle," *Biomaterials*, 33(1);20-17, 2012.
Krutzfeldt, et al., "Silencing of MicroRNAs In Vivo with 'Antagomirs'," *Nature*, 438(1);685-9, 2005.
Lennox & Behlke, "Chemical Modification and Design of Anti-MiRNA Oligonucleotides," *Gene Therapy*, 18(12);1111-1120, 2011.
Liu, et al., "An Association Between—866G/A Polymorphism in the Promoter of UCP2 and Obesity: A Meta-Anaysis," *Gene*, 514(1);41-47, 2013.
Liu, et al., "Reversal of Paclitaxel Resistance in Epithelial Ovarian Carcinoma Cells by a MUC1 Aptamer-let-7i Chimera," *Cancer Investigations*, 30(8); 577-582, 2012.
Liu, et al., "Selection of Aptamers Specific for Adipose Tissue," *PLoS One*, 7(5); e37789, 2012.
Lowell & Spiegelman, "Towards a Molecular Understanding of Adaptive Thermogenesis," *Nature*404(6778); 652-60, 2000.
Mao et al. "The cardiovascular action of hexarelin" *J. Ger. Cardiol* 2014, 11, 253-258.

McGregor & Choi, "MicroRNAs in the Regulation of Adipogenesis and Obesity," *Current Molecular Medicine*, 11(4); 304-316, 2011.
Muller, et al., "Microvesicles Released from Rat Adipocytes and Harboring Glycosylphosphatidylinositol-Anchored Proteins Transfer RNA Stimulating Lipid Synthesis," *Cellular Signalling*, 23; 1207-1223, 2011.
O'Connell, et al., "MicroRNA-155 Promotes Autoimmune Inflammation by Enhancing Inflammatory T Cell Development," *Immunity*, 33(4); 607-619, 2010.
Okada, et al., "Histone Demethylase JHDM2A is Involved in Male Infertility and Obesity," *Journal of Andrology*, 31(1);75-78, 2010.
Petrovic, et al., "Chronic Peroxisome Proliferator-Activated Receptor γ (PPARγ) Activation of Epididymally Derived White Adipocyte Cultures Reveals a Population of Thermogenically Competent, UCP1-Containing Adipocytes Molecularly Distinct from Classic Brown Adipocytes," *Journal of Biological Chemistry*, 285(10); 7153-7164, 2010.
Price & Fernandez-Hernando, "MIRNA Regulation of White and Brown Adipose Tissue Differentiation and Function," *Biochimica et Biophysica Acta—Molecular and Cell Biology of Lipids*, 1861(12Pt B); 2104-2110, 2016.
Rantalainen, et al., "MicroRNA Expression in Abdominal and Gluteal Adipose Tissue is Associated with mRNA Expression Levels and Partly Genetically Driven," *PLoS One*. 6(11): e27338, 2011.
Reiher et al., "Inhibition of Tumor Growth by Systemic Treatment with Thrombospondin-1 Peptide Mimetics" *Int. J. Cancer* 2002, 98, 682-689.
Rieger, et al., "MiRNA-DISTILLER: A Stand-Alone Application to Compile MicroRNA Data from Databases," *Frontiers in Genetics*, 2(39); 1-6, 2011.
Rosen & Spiegelman, "What We Talk About When We Talk About Fat," *Cell*, 156; 20-45, 2014.
Snead & Rossi, "RNA Interference Trigger Variants: Getting the Most Out of RNA for RNA Interference-Based Therapeutics," *Nucleic Acid Therapeutics*, 22(3); 139-146, 2012.
Speakman, et al., "Animal Models of Obesity," *Obesity Reviews*. 8(Suppl 1); 55-61, 2007.
Sun, et al., "MicroRNA Let-7 Regulates 3T3-L1 Adipogenesis," *Molecular Endocrinology*, 23; 925-931, 2009.
Sun, et al., "MicroRNA-15a Positively Regulates Insulin Synthesis by Inhibiting Uncoupling Protein-2 Expression", *Diabetes Research and Clinical Practice* 91; 94-100, 2011.
Sun, et al., "Mir193b-365 is Essential for Brown Fat Differentiation," *Nature Cell Biology*, 13(8); 958-965, 2011.
Supplementary Partial European Search Report Issued in for EP13777669.6, dated May 10, 2016.
Tagliani, et al., "Selection of an Antibody Library Identifies a Pathway to Induce Immunity by Targeting CD36 on Steady-State CD8 Alpha+ Dendritic Cells," *The Journal of Immunology*, 180; 3201-3209, 2008.
TargetScan 5.2, "Prediction of MicroRNA Targets of miR-22", Jun. 2011. Retrieved on Mar. 23, 2016.
Thorsen, et al., "The Therapeutic Potential of MicroRNAs in Cancer," *The Cancer Journal*, 18(3); 275-284, 2012.
Tivnan, et al., "Inhibition of Neuroblastoma Tumor Growth by Targeted Delivery of MicroRNA-34A Using Anti-Disialoganglioside GD2 Coated Nanoparticles," *PLoS One*, 7(5) e38129, 2012.
Van Rooij, et al., "Developing MicroRNA Therapeutics," *Circulation Research*, 110(3); 496-507, 2012.
Wang & Liao, "A Mouse Model of Diet-Induced Obesity and Insulin Resistance," *Methods Molecular Biology*, 821 ; 421-433, 2012.
Wang, et al., "Uncoupling Protein-2 Polymorphisms in Type 2 Diabetes, Obesity, and Insulin Secretion," *American Journal of Physiology-Endocrinology and Metabolism*, 286(1); E1-7, 2004.
Weber, et al., "The MicroRNA Spectrum in 12 Body Fluids," *Clinical Chemistry*, 56(11); 1733-1741, 2010.
Wu, et al., "Second-Generation Aptamer-Conjugated PSMA-Targeted Delivery System for Prostate Cancer Therapy," *International Journal of Nanomedicine*, 6; 1747-1756, 2011.

(56) References Cited

OTHER PUBLICATIONS

Xiao, et al., "Novel Approaches for Gene-Specific Interference Via Manipulating Actions of MicroRNAs: Examination on the Pacemaker Channel Genes HCN2 and HCN4," *Journal of Cellular Physiology*, 212; 285-92, 2007.

Xie, et al., "MicroRNAs Induced During Adipogenesis that Accelerate Fat Cell Development Are Downregulated in Obesity," *Diabetes*, 58; 1050-1057, 2009.

Yin, et al., "MicroRNA-133 Controls Brown Adipose Determination in Skeletal Muscle Satellite Cells by Targeting Prdm16," *Cell Metabolism*, 17(2):210-224, 2013.

Zaragosi, et al., "Small RNA Sequencing Reveals MiR-642a-3P as a Novel Adipocyte-Specific MicroRNA and MiR-30 as a Key Regulator of Human Adipogenesis," *Genome Biology*, 12;1-13, 2011.

Abe, Y. et al., "JMJD1A is a signal-sensing scaffold that regulates acute chromatin dynamics via SWI/SNF association for thermogenesis." Nature Communications, 2015. 6: p. 7052.

Blechinger et al., "Short, terminally modified 2'-OMe RNAs as inhibitors of microRNA." Chem Commun (Camb) 2013, 49(67), p. 7397-9.

Beamer et al. "MicroRNA-22 controls aberrant neurogenesis and changes in neural morphology after status epilepticus", Front. Mol. Neurosci, vol. 11, No. 442, 2018.

Bozzuto et al., "Liposomes as nanomedical devices." International Journal of Nanomedicine, 10:975-999, 2015.

Buzzetti et al. "The multiple-hit pathogenesis of nonalcoholic fatty liver disease (NAFLD)." Metabolism, 2016. 65(8): p. 1038-48.

Chen, C., et al., "Structural basis for molecular recognition of folic acid by folate receptors." Nature, 2013. 500(7463): p. 486-9.

Cheung, A., et al., "Targeting folate receptor alpha for cancer treatment." Oncotarget, 2016. 7(32): p. 52553-52574.

Chi et al., "Safety of antisense oligonucleotide and siRNA-based therapeutics." Drug Discov Today 2017, 22(5), p. 823-833.

Chorn, G., et al., "Single-stranded microRNA mimics." RNA, 2012. 18(10): p. 1796-804.

Cook, D.P. and B.C. Vanderhyden. "Ovarian Cancer and the evolution of subtype classifications using transcriptional profiling dagger." Biol Reprod, 2019. 101(3): p. 645-658.

Correa, L.H et al. "The Impact of the Adipose Organ Plasticity on Inflammation and Cancer Progression." Cells, 2019. 8(7).

Croft, P.K et al., "Ovarian-Cancer-Associated Extracellular Vesicles: Microenvironmental Regulation and Potential Clinical Applications." Cells, 2021. 10(9).

Dahlman et al., "In vivo endothelial siRNA delivery using polymeric nanoparticles with low molecular weight." Nature Nanotechnology, 9(8): 648-655, 2014.

Deb et al., "miRNAs and Ovarian Cancer: An overview." J Cell Physiol, 2018. 233(5): p. 3846-3854.

Della-Longa, S. et al. "Structural and functional insights on folate receptor alpha (FRα) by homology modeling, ligand docking and molecular dynamics." J Mol Graph Model, 2013. 44: p. 197-207.

Dong et al., "Lipopeptide nanoparticles for potent and selective siRNA delivery in rodents and nonhuman primates." Proc. Natl. Acad. Sci. U S A., 111(11):3955-3960, 2014.

Dowdy, S.F., et al., "Delivery of RNA Therapeutics: The Great Endosomal Escape!" Nucleic Acid Ther., 2022. 32(5): p. 361-368.

Falzone, L., et al., "A multidisciplinary approach remains the best strategy to improve and strengthen the management of Ovarian Cancer (Review)." Int J Oncol, 2021. 59(1).

Flierl et al., "Phosphorothioate backbone modifications of nucleotide-based drugs are potent platelet activators." J Exp Med 2015, 212(2), p. 129-37.

Frazier, K.S., "Antisense oligonucleotide therapies: the promise and the challenges from a toxicologic pathologist's perspective." Toxicol Pathol 2015, 43(1), p. 78-89.

Gajek, A et al., "Current Implications of microRNAs in Genome Stability and Stress Responses of Ovarian Cancer." Cancers (Basel), 2021. 13(11).

Gaona-Luviano et al., "Epidemiology of Ovarian Cancer." Chin Clin Oncol, 2020. 9(4): p. 47.

Ghafouri-Fard et al., "miRNA profile in Ovarian Cancer." Exp Mol Pathol, 2020. 113: p. 104381.

Gharpure, K.M. et al., "FABP4 as a key determinant of metastatic potential of Ovarian Cancer." Nat Commun, 2018. 9(1): p. 2923.

Glatz, J. F et a l., "Regulation of the subcellular trafficking of CD36, a major determinant of cardiac fatty acid utilization." Biochimica et Biophysica Acta, 2016. 1861(10): p. 1461-71.

Glatz, J.F. et al. "From fat to Fat (CD36/SR-B2): Understanding the regulation of cellular fatty acid uptake." Biochimie, 2017. 136: p. 21-26.

Guo, L., et al., "Expression profiles analysis reveals an integrated miRNA-lncRNA signature to predict survival in Ovarian Cancer patients with wild-type BRCA1/2." Oncotarget, 2017. 8(40): p. 68483-68492.

Gutierrez, et al. "Thrombospondin 1 in Metabolic Diseases." Front. Endocrinol. (Lausanne), 2021. 12: p. 638536.

Ha, M. et al. "Regulation of microRNA biogenesis." Nat. Rev. Mol. Cell Biol., 2014. 15(8): p. 509-24.

Hammond, S.M., et al., "Delivery of oligonucleotide-based therapeutics: challenges and opportunities." EMBO Mol Med, 2021. 13(4): p. e13243.

Hanson, A., et al. "The Role of Long Non-Coding RNAs (lncRNAs) in the Development and Progression of Fibrosis Associated with Nonalcoholic Fatty Liver Disease (NAFLD)." Noncoding RNA, 2018. 4(3).

Hardee, G.E., "Oral delivery of nucleic acid-based therapeutics." Ther. Deliv., 3(2):143-145, 2012.

Hausler, S.F., et al., "Whole blood-derived miRNA profiles as potential new tools for Ovarian Cancer screening." Br J Cancer, 2010. 103(5): p. 693-700.

Hu, J., et al., "Exploring the effect of sequence length and composition on allele-selective inhibition of human huntingtin expression by single-stranded silencing RNAs." Nucleic Acid Ther., 2014. 24(3): p. 199-209.

International Search Report and Written opinion issued in corresponding International Application No. PCT/US19/40259 mailed on Sep. 20, 2019.

International Search Report and Written Opinion issued in Corresponding PCT Application No. PCT/US2019/049855, dated Dec. 18, 2019.

Inui et al., "MicroRNA control of signal transduction." Nat Rev Mol Cell Biol, 2010. 11: p. 252-63.

Iyoshi, S., et al., "Pro-tumoral behavior of omental adipocyte-derived fibroblasts in tumor microenvironment at the metastatic site of Ovarian Cancer." Int J Cancer, 2021. 149(11): p. 1961-1972.

Jastreboff, A.M., et al., "Tirzepatide Once Weekly for the Treatment of Obesity." New England J. Med., 2022. 387(3): p. 205-216.

Ji, Z., et al., "Deregulation of Lipid Metabolism: The Critical Factors in Ovarian Cancer." Front Oncol, 2020. 10: p. 593017.

Kalfert, D., et al., "Multifunctional Roles of miR-34a in Cancer: A Review with the Emphasis on Head and Neck Squamous Cell Carcinoma and Thyroid Cancer with Clinical Implications." Diagnostics (Basel), 2020. 10(8).

Kalli, K.R., et al., "Folate receptor alpha as a tumor target in epithelial Ovarian Cancer." Gynecol Oncol, 2008. 108(3): p. 619-26.

Khvorova, A. et al. "The chemical evolution of oligonucleotide therapies of clinical utility." Nat Biotechnol 2017, 35(3), p. 238-248.

Kossai, M., et al., "Ovarian Cancer: A Heterogeneous Disease." Pathobiology, 2018. 85(1-2): p. 41-49.

Iacomino, G. et al. "Role of microRNAs in obesity and obesity-related diseases." Genes Nutr., 2017. 12: p. 23.

Iacomino, G., "miRNAs: The Road from Bench to Bedside." Genes (Basel), 2023. 14(2).

Lajoie, P., et al., "Lattices, rafts, and scaffolds: domain regulation of receptor signaling at the plasma membrane." J Cell Biol, 2009. 185(3): p. 381-5.

Le Roux, C. W ., et al., "Tirzepatide for the treatment of obesity: Rationale and design of the SURMOUNT clinical development program." Obesity (Silver Spring), 2023. 31(1): p. 96-110.

(56) References Cited

OTHER PUBLICATIONS

Lheureux et al., "Epithelial Ovarian Cancer: Evolution of management in the era of precision medicine." CA Cancer J Clin, 2019. 69(4): p. 280-304.

Li et al., "Therapeutic targeting of microRNAs: current status and future challenges." Nature Reviews Drug Discovery, 13(8):622-638, 2014.

Liang, Z., et al., "Targeting Membrane Receptors of Ovarian Cancer Cells for Therapy." Curr Cancer Drug Targets, 2019. 19(6): p. 449-467.

Lima, W.F., et al., "Single-stranded siRNAs activate RNAi in animals." Cell, 2012. 150(5): p. 883-94.

Lopez-Camarillo, C., et al., "Deciphering the Long Non-Coding RNAs and MicroRNAs Coregulation Networks in Ovarian Cancer Development: An Overview." Cells, 2021. 10(6).

Luiken, J.J., et al., "Post-translational modifications of CD36 (SR-B2): Implications for regulation of myocellular fatty acid uptake." Biochimica et Biophysica Acta, 2016. 1862(12): p. 2253-2258.

Maher et al., "Safety and efficacy of sodium caprate in promoting oral drug absorption: from in vitro to the clinic", Adv. Drug Deliv. Rev., 61(15):1427-1449, 2009.

Marchetti, C., et al., "Targeted drug delivery via folate receptors in recurrent Ovarian Cancer: a review." Onco Targets Ther, 2014. 7: p. 1223-36.

Marechal, L., et al., The CD36-PPARgamma Pathway in Metabolic Disorders. Int. J. Mol. Sci., 2018. 19(5).

Martin-Sabroso, C., et al., "Active Targeted Nanoformulations via Folate Receptors: State of the Art and Future Perspectives." Pharmaceutics, 2021. 14(1).

Matsui, M., et al. "Argonaute 2-dependent Regulation of Gene Expression by Single- stranded miRNA Mimics." Mol. Ther., 2016. 24(5): p. 946-55.

Milhas et al., "Sphingomyelin metabolism at the plasma membrane: implications for bioactive sphingolipids." FEBS Lett, 2010. 584(9): p. 1887-94.

Mirahmadi, Y., et al., "MicroRNAs as Biomarkers for Early Diagnosis, Prognosis, and Therapeutic Targeting of Ovarian Cancer." J Oncol, 2021. 2021 : p. 3408937.

Moccia et al., "Insights on chiral, backbone modified peptide nucleic acids: Properties and biological activity." Artif Dna Pna Xna 2014, 5, 1-15.

Mosa et al., Hexarelin, a Growth Hormone Secretagogue, Improves Lipid Metabolic Aberrations in Nonobese Insulin-Resistant Male MKR Mice. Endocrinology, 158(10):3174-3187, 2017.

Motohara, T., et al., "An evolving story of the metastatic voyage of Ovarian Cancer cells: cellular and molecular orchestration of the adipose-rich metastatic microenvironment." Oncogene, 2019. 38(16): p. 2885-2898.

Moumne, L., "Oligonucleotide Therapeutics: From Discovery and Development to Patentability." Pharmaceutics, 2022. 14(2).

Mukherjee, A., et al., "Adipocyte-Induced FABP4 Expression in Ovarian Cancer Cells Promotes Metastasis and Mediates Carboplatin Resistance." Cancer Res, 2020. 80(8): p. 1748-1761.

Nielsen et al., Sequence-selective recognition of DNA by strand displacement with a thymine-substituted polyamide. Science, 1991, 254, 1497-1500.

Nieman, K.M., et al., "Adipocytes promote Ovarian Cancer metastasis and provide energy for rapid tumor growth." Nat Med, 2011. 17(11): p. 1498-503.

Nikam, R.R. et al. Journey of siRNA: Clinical Developments and Targeted Delivery.: Nucleic Acid Ther., 2018. 28(4): p. 209-224.

Obad et al., "Silencing of microRNA families by seeding-targeting tiny LNAs", Nat Genet, 2011, 43, p. 371-8.

Oh et al. "A highly effective and long-lasting inhibition of miRNAs with PNA- based antisense oligonucleotides", Mol. Cells, vol. 28, pp. 341-345, 2009.

Pascual-Anton, L., et al., "Mesothelial-to-Mesenchymal Transition and Exosomes in Peritoneal Metastasis of Ovarian Cancer." Int J Mol Sci, 2021. 22(21).

Prakash et al., "Synergistic effect of phosphorothioate, 5'-vinylphosphonate and GalNAc modifications for enhancing activity of synthetic siRNA." Bioorg Med Chem Lett 2016, 26(12), p. 2817-2820.

Roberts, T.C., et sl. "Advances in oligonucleotide drug delivery." Nat Rev Drug Discov, 2020. 19(10): p. 673-694.

Rodrigue-Way, A., et al., "A growth hormone-releasing peptide promotes mitochondrial biogenesis and a fat burning-like phenotype through scavenger receptor CD36 in white adipocytes." Endocrinology, 2007. 148(3): p. 1009-18.

Roett, M.A. et al. "Ovarian Cancer: an overview." Am Fam Physician, 2009. 80(6): p. 609-16.

Rottiers et al., "Pharmacological inhibition of a microRNA family in nonhuman primates by a seed-targeting 8-mer antimiR." Sci Transl Med 2013, 5(212), p. 212ra162, 21 p.

Rupaimoole, R. et al. "MicroRNA therapeutics: towards a new era for the management of cancer and other diseases." Nat Rev Drug Discov 2017, 16(3), p. 203-222.

Rupert, J.E. et al. "Fatty acid translocase: a culprit of lipid metabolism dysfunction in disease." Immunometabolism (Cobham), 2022. 4(3): p. e00001.

Sarwar, R., et al. "Obesity and nonalcoholic fatty liver disease: current perspectives." Diabetes Metab. Syndr. Obes., 2018. 11: p. 533-542.

Scaranti, M., et al., "Exploiting the folate receptor alpha in oncology." Nat Rev Clin Oncol, 2020. 17(6): p. 349-359.

Sewing et al., "Assessing single-stranded oligonucleotide drug-induced effects in vitro reveals key risk factors for thrombocytopenia." PLoS One 2017, 12(11), p. e0187574, 18 pages.

Slabakova, E., et al., "Alternative mechanisms of miR-34a regulation in cancer." Cell Death Dis, 2017. 8(10): p. e3100.

Strumidlo, A., et al., "The potential role of miRNAs in therapy of breast and Ovarian Cancers associated with BRCA1 mutation." Hered Cancer Clin Pract, 2017. 15: p. 15.

Sung, H., et al., "Global Cancer Statistics 2020: GLOBOCAN Estimates of Incidence and Mortality Worldwide for 36 Cancers in 185 Countries." CA Cancer J Clin, 2021. 71(3): p. 209-249.

Suparpprom, C et al. "Perspectives on conformationally constrained peptide nucleic acid (PNA): insights into the structural design, properties and applications." RSC Chem. Biol., 2022. 3(6): p. 648-697.

Talhouk, A., et al., "Development and Validation of the Gene Expression Predictor of High-grade Serous Ovarian Carcinoma Molecular SubTYPE (PrOTYPE)." Clin Cancer Res, 2020. 26(20): p. 5411-5423.

Tateishi, K., et al., "Role of Jhdm2a in regulating metabolic gene expression and obesity resistance." Nature, 2009. 458(7239): p. 757-61.

Thibonnier et al., "Metabolic and energetic benefits of microRNA-22 inhibition." BMJ Open Diabetes Res. Care, 8(1):e001478, 2020.

Thibonnier et al., "Metabolic Benefits of MicroRNA-22 Inhibition." Nucleic Acid Ther., 30(2):104-116, 2020.

Thibonnier, M. et al. "Strategy for Pre-Clinical Development of Active Targeting MicroRNA Oligonucleotide Therapeutics for Unmet Medical Needs." Int J Mol Sci, 2023. 24(8).

Van Rooij et al., "Development of microRNA therapeutics is coming of age." EMBO Mol. Med., 6(7):851-864, 2014.

Wallace-Povirk, A., et al., "Folate Transport and One-Carbon Metabolism in Targeted Therapies of Epithelial Ovarian Cancer." Cancers (Basel), 2021. 14(1).

Webb et al., "Sphingomyelin-cholesterol liposomes significantly enhance the pharmacokinetic and therapeutic properties of vincristine in murine and human tumour models." Br. J. Cancer., 72(4):896-904, 1995.

Wilding, J.P.H., et al., "Once-Weekly Semaglutide in Adults with Overweight or Obesity." New England J. Med., 2021. 384(11): p. 989-1002.

Wittrup et al., "Knocking down disease: a progress report on siRNA therapeutics." Nature Reviews Genetics, 16(9):543-552, 2015.

Wu, M., et al., "Identification of Hub Genes in High-Grade Serous Ovarian Cancer Using Weighted Gene Co-Expression Network Analysis." Med Sci Monit, 2020. 26: p. e922107.

(56) References Cited

OTHER PUBLICATIONS

Yang, D., et al., "Integrated bioinformatics analysis for the screening of hub genes and therapeutic drugs in Ovarian Cancer." J Ovarian Res, 2020. 13(1): p. 10.

Yang, Y., et al., "Identification of metastasis and prognosis-associated genes for serous Ovarian Cancer." Biosci Rep, 2020. 40(6).

Yang, Y., et al., "Tumor Microenvironment in Ovarian Cancer: Function and Therapeutic Strategy." Front Cell Dev Biol, 2020. 8: p. 758.

Yavari, N., "Uptake, Stability, and Activity of Antisense Anti-acpP PNA-Peptide Conjugates in Escherichia coli and the Role of SbmA." ACS Chem. Biol., 2021. 16(3): p. 471-479.

Yoshida, K., et al., "The clinical impact of intra- and extracellular miRNAs in Ovarian Cancer." Cancer Sci, 2020. 111(10): p. 3435-3444.

Younossi, Z., et al., "Global burden of NAFLD and NASH: trends, predictions, risk factors and prevention." Nat. Rev. Gastroenterol. Hepatol., 2018. 15(1): p. 11-20.

Yu et al., "Insight into mechanisms of cellular uptake of lipid nanoparticles and intracellular release of small RNAs." Pharm. Res., 31(10):2685-2695, 2014.

Zatsepin et al., "Lipid nanoparticles for targeted siRNA delivery—going from bench to bedside." Int. J. Nanomedicine, 11:3077-3086, 2016.

Zhang et al., "Progress in microRNA delivery." J. Control Release., 172(3):962-974, 2013.

Zhang, C et al. "RNA therapeutics: updates and future potential." Sci. China Life Sci., 2023. 66(1): p. 12-30.

Zhao et al., "Ovarian Cancer-Why Lipids Matter." Cancers (Basel), 2019. 11(12).

Zhou, D., et al., "CD36 level and trafficking are determinants of lipolysis in adipocytes." Faseb J., 2012. 26(11): p. 4733-42.

\* cited by examiner

FIG. 1

| | | | |
|---|---|---|---|
| ACLY | ELOVL6 | NR3C1 | SIRT1 |
| ALDH1A1 | FGF19 | NRF1 | SREBF1 |
| ALDH5A1 | FGF21 | NRIP1 | SREBF2 |
| BMP4 | FOXC2 | PCLO | STAT5A |
| BMP7 | INSR | PHACTR2 | TNFRSF1A |
| CAV3 | KDM3A | PPARA | TRIM67 |
| CD1D | KDM6B | PPARGC1A | TRPM8 |
| CDKN1A | KLF11 | PPARGC1B | UCP1 |
| CEBPA | KLF6 | PRDM16 | UCP2 |
| CEBPD | LAMC1 | PRDX3 | WNT1 |
| CIDEC | LRP6 | PRKAA1 | WNT10B |
| CREB1 | MAPK14 | PRKACA | WNT5A |
| CREBBP | MFGE8 | PRKACB | |
| CTNNB1 | NAA20 | PRKAR1A | |
| DIO2 | NCOA1 | RUNX1T1 | |
| EIF4EBP2 | NPPA | RUNX2 | |

FIG. 2

| miR-22-3p Targets | Control (rpm) | miR-22-3p (rpm) | Fold Change | P value | P adj value |
|---|---|---|---|---|---|
| CEBPD | 183 | 277 | 1.52 | 0.00 | 8.13593E-05 |
| CREB1 | 441 | 534 | 1.21 | 0.01 | 0.0783094 |
| EIF4EBP2 | 1,973 | 2,353 | 1.19 | 0.00 | 0.017610613 |
| KDM3A | 223 | 290 | 1.30 | 0.00 | 0.030445954 |
| KDM6B | 51 | 86 | 1.70 | 0.00 | 0.016626718 |
| KLF11 | 146 | 185 | 1.27 | 0.02 | 0.159828799 |
| KLF6 | 441 | 557 | 1.26 | 0.00 | 0.014730829 |
| LAMC1 | 13,242 | 15,567 | 1.18 | 0.02 | 0.124571301 |
| MFGE8 | 1,484 | 1,284 | 0.87 | 0.02 | 0.143404353 |
| NAA20 | 267 | 224 | 0.84 | 0.04 | 0.228487863 |
| NCOA1 | 436 | 505 | 1.16 | 0.04 | 0.221436136 |
| PPARA | 466 | 719 | 1.54 | 0.00 | 6.21199E-09 |
| PPARGC1B | 131 | 163 | 1.24 | 0.02 | 0.162224841 |
| PRDX3 | 1,472 | 1,176 | 0.80 | 0.01 | 0.06880409 |
| RUNX2 | 59 | 86 | 1.47 | 0.01 | 0.069401676 |
| SIRT1 | 241 | 290 | 1.20 | 0.03 | 0.184643015 |
| TRPM8 | 11 | 16 | 1.53 | 0.17 | 0.516413136 |
| UCP1 | 8 | 12 | 1.48 | 0.18 | 0.535730354 |

Inguinal fat

Saline | APT-110

Perirenal fat

Saline | APT-110

Subscapular white fat

Saline | APT-110

Subscapular brown fat

Saline | APT-110

- Fluorescent miRNAs were delivered to mature human adipocytes in culture via natural lipid nanoparticles developed by AptamiR
- Nuclei are stained in blue, lipid droplets in green and fluorescent miRNAs in red Cells transfected with lipofectamine Cells transfected with AptamiR's carrier Non transfected cells

INHIBITION OF MIR-22 miRNA BY APT-110

CROSS-REFERENCE TO RELATED APPLICATIONS

This application is a continuation of U.S. patent application Ser. No. 16/097,012 filed Oct. 26, 2018, which is a national phase application under 35 U.S.C. § 371 of International Application No. PCT/IB2017/052505 filed Apr. 28, 2017, which claims the benefit of priority of U.S. Provisional Patent Application No. 62/329,537 filed Apr. 29, 2016, all of which are hereby incorporated by reference in their entirety.

REFERENCE TO A SEQUENCE LISTING

This application contains a Sequence Listing in computer readable form. The computer readable form is incorporated herein by reference. Said ASCII copy, created on Apr. 3, 2024, is named APTA_P0007USC1_1001134313_SL.txt and is 12,965 bytes in size.

FIELD OF THE INVENTION

This invention relates to the fields of molecular biology, microbiology, pharmacology, and synthetic organic chemistry.

BACKGROUND

Human obesity has become a worldwide pandemic due to sedentary lifestyle and excessive consumption of energy-dense foods rich in saturated fats and sugars. It currently affects one third of the world population, including adolescents and children (Ng, M., et al., 2014). Obesity and excessive weight are major risk factors for many chronic diseases, including diabetes mellitus, hyperlipidemia, cardiovascular diseases, visceral inflammation, and several cancers (Wilborn, C., et al., 2005). Furthermore, obesity and excessive weight are the cause of lost earnings, restricted activity days, absenteeism, lower productivity at work (presenteeism), reduced quality of life, permanent disability, significant morbidity and mortality, and shortened lifespan. About 400,000 deaths per year in the US are related to obesity. Obesity is responsible for more than 10% of US total healthcare costs (Wang, Y., et al., 2008). Furthermore, voluntary spending on weight loss, mostly on unproven means, exceeds $75 billion annually.

Current medical treatments of human obesity have poor benefit-to-risk profiles, fail to attain long-term therapeutic goals, do not meet patients' expectations and are often not covered by health insurance plans (Haslam, D. W., et al., 2005). Therefore, there is a pressing need to develop an effective and safe medical treatment of human obesity and related disorders that should significantly reduce health care expenses, improve and save human lives.

Obesity is the result of a chronic imbalance between energy intake and expenditure. This imbalance leads to storage of excess energy as fat (triglycerides) into adipocytes, which typically exhibit both hypertrophy (increase in cell size) and hyperplasia (increase in cell number or adipogenesis). Therefore, treatments that target this imbalance are needed.

SUMMARY

The inventor has identified methods for treating human obesity and related disorders through the administration of a novel inhibitor of mir-22 microRNA (miRNA). Specifically, it has been found that administration of a mir-22 inhibitor brings about a series of positive metabolic effects, including weight loss, fat mass reduction, increased energy expenditure, and improvement of glucose control, insulin sensitivity and cholesterol levels. The disclosure provides a miRNA inhibitor that provides upstream control of a variety of proteins involved in metabolism and thermogenesis. In some embodiments, the miRNA inhibitor inhibits mir-22 miRNA. In further embodiments, the miRNA inhibitor inhibits the mature 3p nucleotide of mir-22 miRNA. mir-22 has the stem-loop structure shown in FIG. 16. The mature sequence, hsa-mir-22-3p is aagcugccaguugaagaacugu (SEQ ID NO: 6), and the mature sequence, hsa-mir-22-5p, is aguuc-uucaguggcaagcuuua (SEQ ID NO: 12). In some aspects, administration of a mir-22 inhibitor to a subject increases thermogenesis in the subject.

In some embodiments, the mi-RNA inhibitor is a compound of the formula (SEQ ID NO: 13):

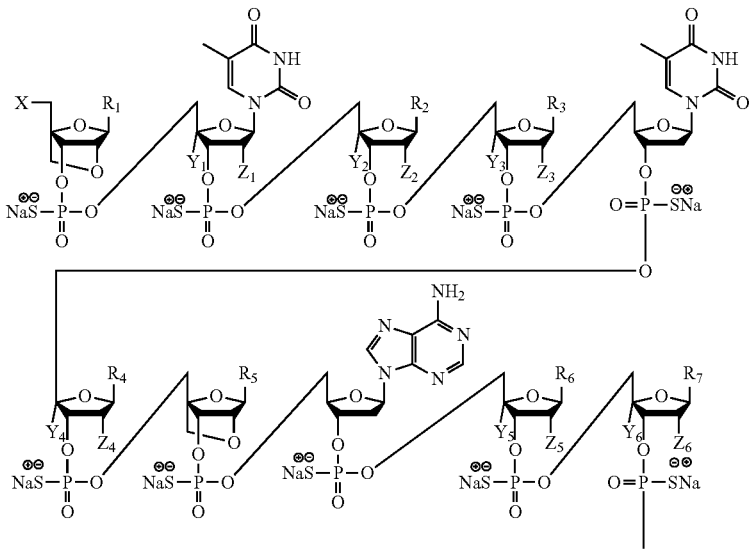

-continued

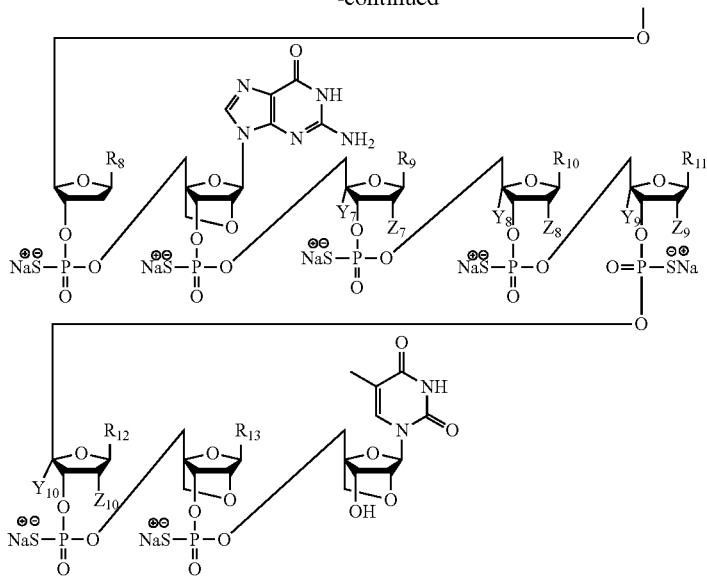

wherein X is OH or a sodium or protonated phosphorothioate 5'-hydroxy nucleotide; R1 is cytosine, 5-methyl cytosine, guanine, or thymine; R2, R3, R4, R7, and R13 are each independently cytosine, 5-methyl cytosine, or thymine; R5, R6, and R10 are each independently adenine, 5-methyl cytosine, or cytosine; R8 is guanine or thymine; R9 and R12 are each independently cytosine, 5-methyl cytosine, or guanine; R11 is adenine or guanine; R12 is cytosine, 5-methyl cytosine, or thymine; and Y1-Y10 are H and Z1-Z10 each independently H or OMe, or the respective Y and Z groups on a sugar moiety join to form an internal ether where Y is methylene and Z is an oxygen atom. In some embodiments, the miRNA inhibitor comprises counter-ions other than sodium, or is a protonated version thereof.

Methods of inhibiting mir-22 in a cell are disclosed herein. In some embodiments, a method of inhibiting mir-22 in a cell comprises administering to the cell a mir-22 antagonist, a molecule comprising a therapeutic agent conjugated to a fatty acid, a liposome comprising phospholipids, cholesterol, and a therapeutic agent, or a nanoparticle containing a therapeutic agent. The cell may be an adipocyte, pre-adipocyte, fibroblast, or vascular endothelial cell. In some embodiments, the cell is an adipose tissue cell. In further embodiments, the adipose tissue cell is subcutaneous white adipose cell or brown adipose tissue cell.

Some aspects of the present disclosure are directed towards a molecule comprising a therapeutic agent conjugated to a fatty acid. In some embodiments, the fatty acid may be a C10 to C35 chain fatty acid. In some embodiments, the fatty acid selected from decanoic acid, dodecanoic acid, oleic acid, stearic acid, docosanoic acid, and dotriacontahexaenoic acid. In some embodiments, the therapeutic agent is a nucleic acid (Oligonucleotide Therapeutic, ONT), a gene editing agent, a polypeptide, or a small molecule. In some embodiments, the nucleic acid is a miRNA.

Some aspects of the present disclosure are directed towards a liposome comprising phospholipids and cholesterol. The liposome diameter may range from 100 to 200 nm. In some embodiments, the liposome comprises a targeting element such as a peptide or an antibody. In some embodiments, the targeting element is a TSP-1 polypeptide. In some embodiments, the TSP-1 polypeptide comprises the sequence GVITRIR (SEQ ID NO:1). In some embodiments, the targeting element is a Hexarelin polypeptide. In some embodiments, the Hexarelin polypeptide comprises the sequence HWAWFL (SEQ ID NO:2). In some embodiments, the targeting element is a Prohibitin polypeptide. In some embodiments, the Prohibitin polypeptice comprises the sequence CKGGRAKDC (SEQ ID NO:3). The liposomal phospholipids and cholesterol may be present in a weight ratio of 80:20. In some embodiments, the phospholipids are selected from sphingomyelin, 1,2-dimyristoyl-sn-glycero-3-phosphocholine (DMPC), or both. In some embodiments, the liposome comprises both sphingomyelin and DMPC. Sphingomyelin, DMPC, and cholesterol may be present in a weight ratio of 40:40:20. In some embodiments, the liposome further comprises a therapeutic agent. In some embodiments, the therapeutic agent may be a polypeptide, a nucleic acid, or a small molecule. In some embodiments, the therapeutic agent is conjugated to a fatty acid.

Some aspects of the present disclosure are directed towards a method for delivering a therapeutic agent to an adipocyte. In some embodiments, the method comprises administering a molecule comprising a therapeutic agent conjugated to a fatty acid, a liposome comprising phospholipids, cholesterol, and a therapeutic agent, or a nanoparticle containing a therapeutic agent to an adipocyte. In some embodiments, the adipocyte is an in vivo adipocyte. In some embodiments, the biodistribution of the therapeutic agent is at least 50% in adipocytes.

In some aspects, a method for upregulating the histone demethylase activity of KDM3A or KDM6B in a cell is provided. The method comprises administering to the cell a mir-22 antagonist, a liposome comprising phospholipids, cholesterol, and a therapeutic agent, or a molecule comprising a therapeutic agent conjugated to a fatty acid. Upregulation of KDM3A and/or KDM6B increases histone demethylation in the PPARA gene region, which in turn upregulates expression of PPARA. In some embodiments, upregulation of PPARA expression activates lipid catabolism and thermogenesis. Upregulation of KDM3A and/or KDM6B increases histone demethylation in the UCP1 gene region, which in turn upregulates expression of UCP1. In some embodiments, upregulation of UCP1 expression increases mitochondrial proton leak. In some embodiments, increasing mitochondrial proton leak increases cellular thermogenesis and cellular caloric expenditure.

The compositions disclosed herein may be used to positively affect a multitude of metabolic processes. Some aspects of the present disclosure are directed towards a method for affecting weight and fat mass reduction in a subject. Some aspects are directed towards increasing caloric expenditure in a subject. Some aspects are directed towards a method of decreasing total fat mass in a subject. In some aspects, methods of decreasing blood glucose levels in a subject are presented. In some aspects, methods of decreasing blood insulin levels in a subject are presented. In some embodiments, methods of decreasing blood cholesterol levels in a subject are presented. In some embodiments, methods of decreasing blood leptin levels in a subject are presented. Some embodiments are directed towards methods of maintaining insulin sensitivity in a subject. In some aspects, methods for converting white adipocytes to brown adipocytes are disclosed. In some embodiments, methods for increasing lipolysis in a subject are disclosed. Some embodiments of the present disclosure are directed towards methods for increasing beta-oxidation of fatty acids in a subject. Some aspects of the present disclosure are directed towards methods for increasing thermogenesis in a subject. The methods comprise administering to a subject a composition comprising a miRNA or therapeutic agent of the formula (SEQ ID NO: 13):

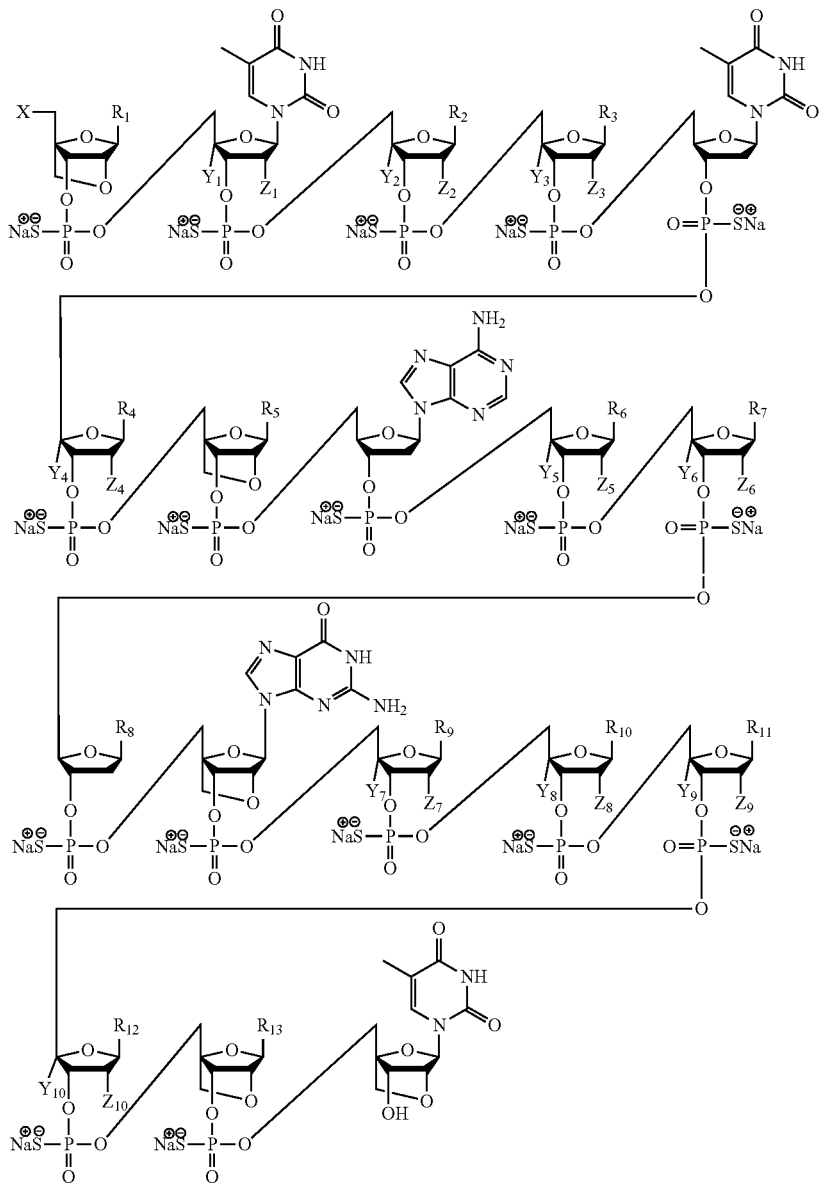

wherein X is OH or a sodium or protonated phosphorothioate 5'-hydroxy nucleotide; R1 is cytosine, 5-methyl cytosine, guanine, or thymine; R2, R3, R4, R7, and R13 are each independently cytosine, 5-methyl cytosine, or thymine; R5, R6, and R10 are each independently adenine, 5-methyl cytosine, or cytosine; R8 is guanine or thymine; R9 and R12 are each independently cytosine, 5-methyl cytosine, or guanine; R11 is adenine or guanine; R12 is cytosine, 5-methyl cytosine, or thymine; and Y1-Y10 are H and Z1-Z10 each independently H or OMe, or the respective Y and Z groups on a sugar moiety join to form an internal ether where Y is methylene and Z is an oxygen atom. In some embodiments, the miRNA inhibitor comprises counter-ions other than sodium, or is a protonated version thereof.

In particular embodiments, the miRNA inhibitor or therapeutic agent is a compound of the following structure (SEQ ID NO: 17):

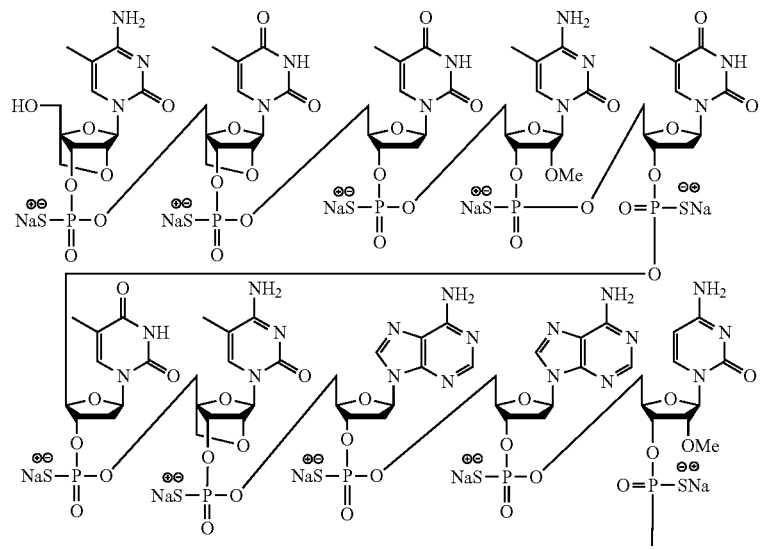

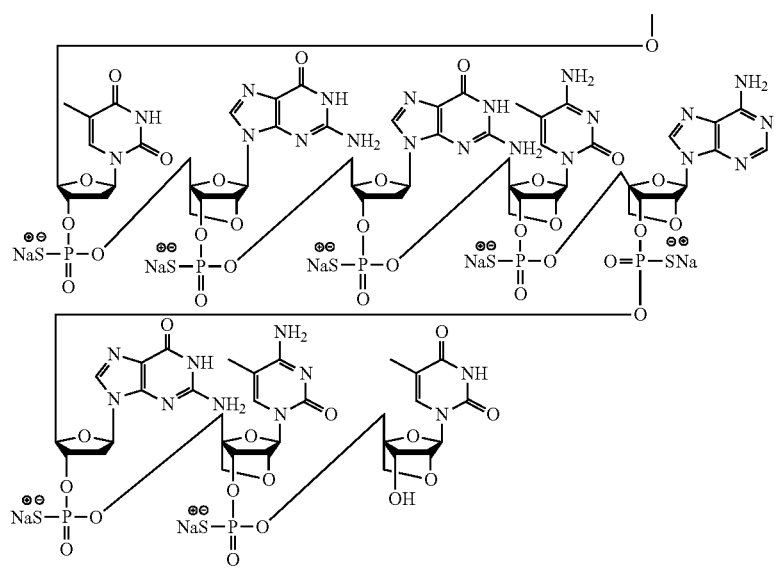

In some embodiments, the miRNA inhibitor or therapeutic agent is a compound of the following structure (SEQ ID NO: 14):

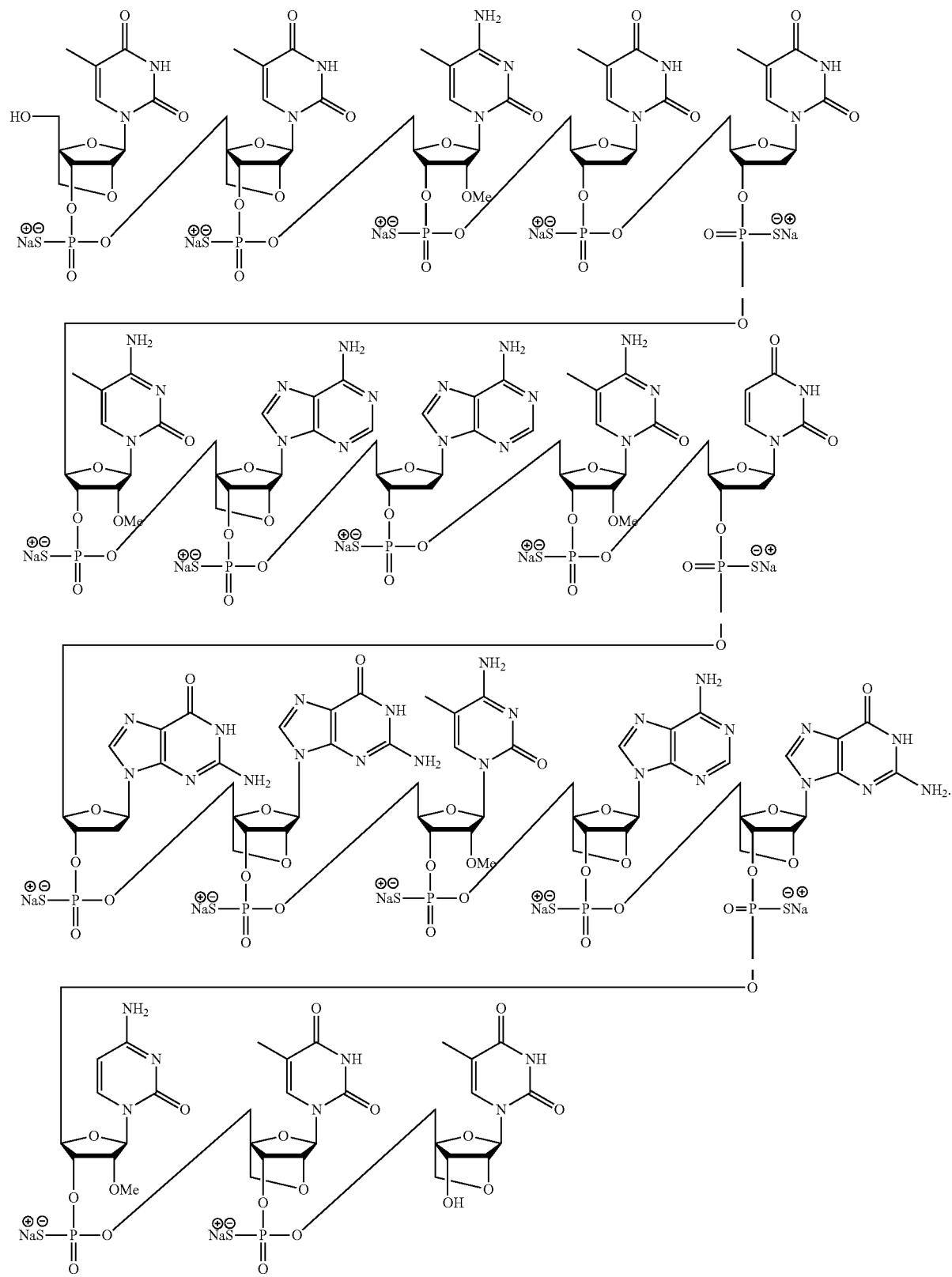
APT-109

In further embodiments, the miRNA inhibitor or therapeutic agent is a compound of the following structure (SEQ ID NO: 15):
APT-133
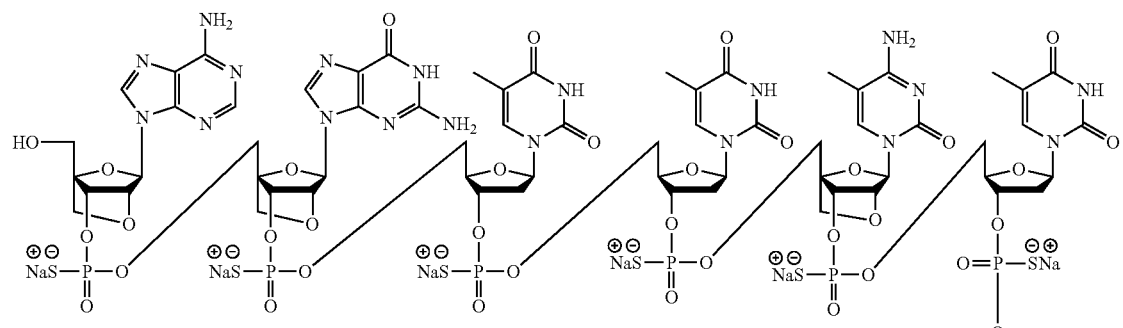
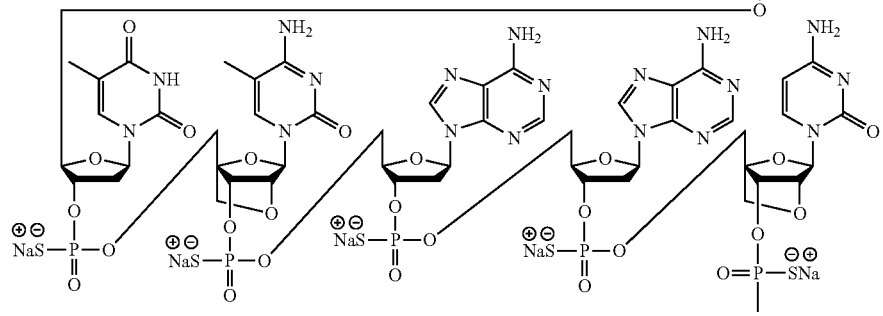
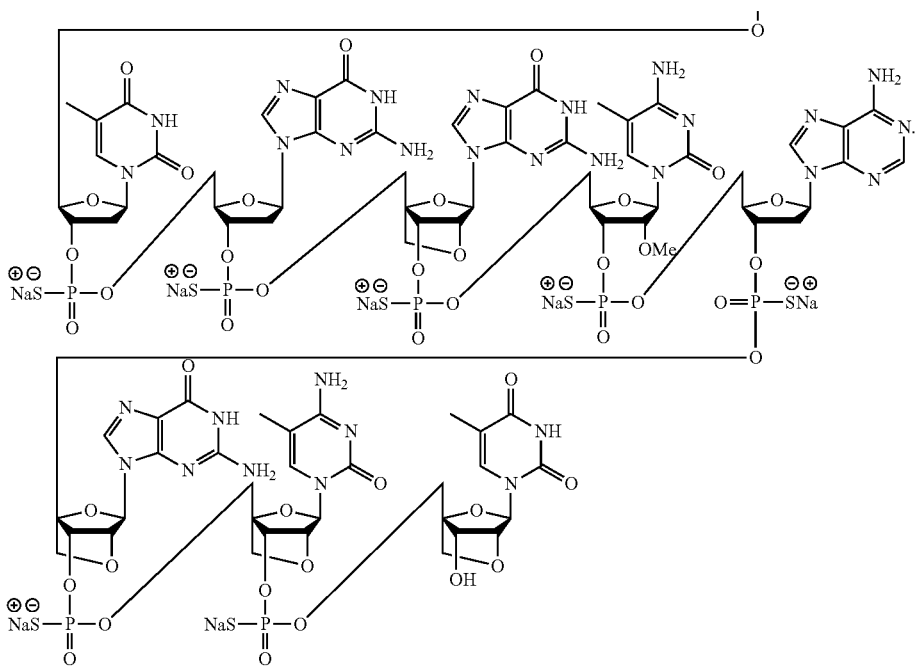
In other embodiments, the miRNA inhibitor or therapeutic agent is a compound of the following structure (SEQ ID NO: 16):

APT-140

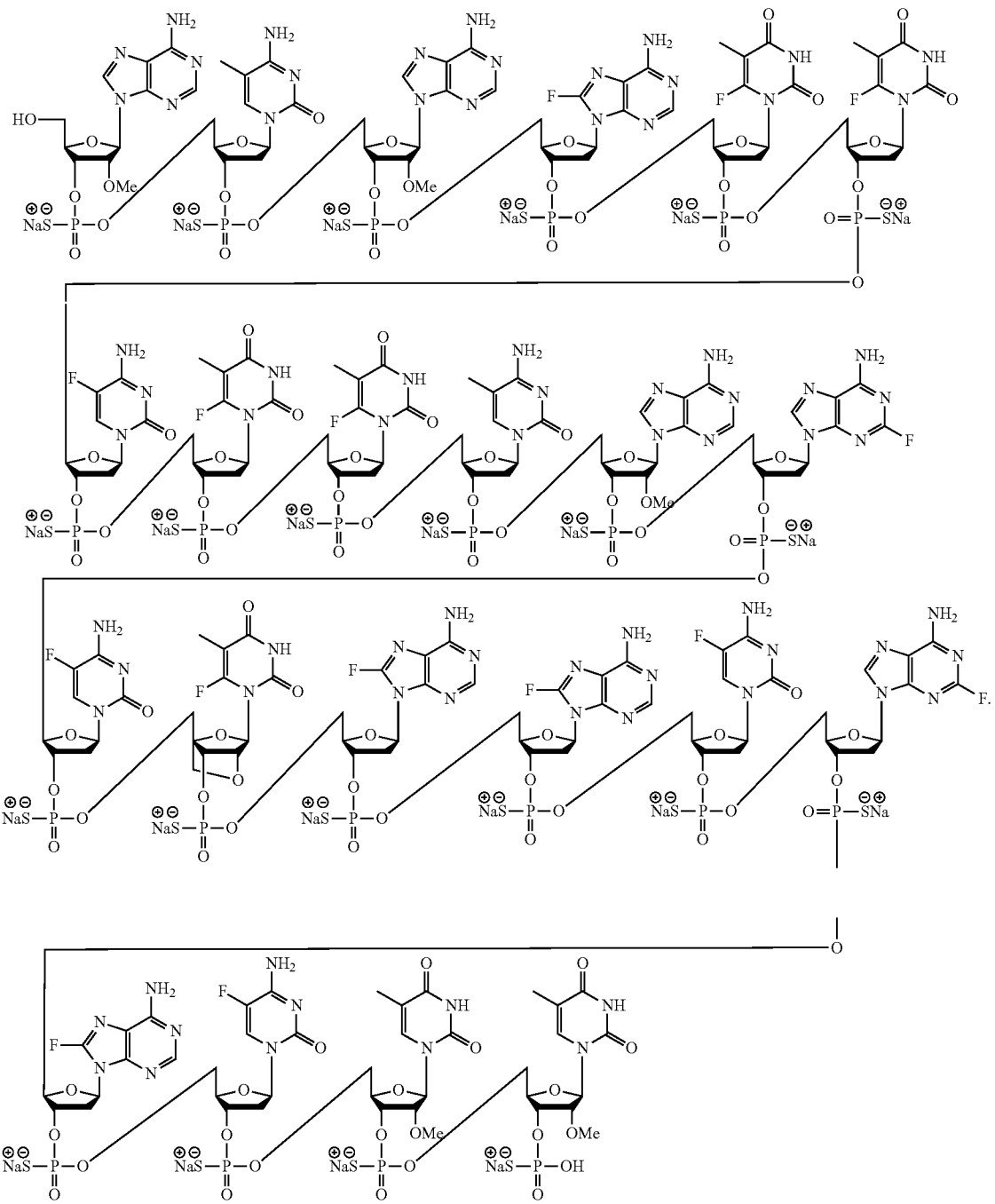

Various analogs, including protonated acid variants, compounds with modifications to one or more ribose sugars, compounds with different bases, including both naturally-occurring and synthetic or semi-synthetic variants are contemplated. In some embodiments, a variant includes at least one of a modified backbone, a modified sugar moiety, and a modified base. Modifications include, but are not limited to, replacement of atoms, e.g., S→O, addition of functional groups, e.g., 2'OMe and N-alkylated amines, replacement, omission, or addition of backbone thiophosphate, ribose sugar, or base. Various salts, including replacement of counter-ions, e.g., Na→K, or modification of an ionic functional group to a non-ionic functional group, e.g., OMe→COO⁻, and vice versa, e.g., S⁻→SMe, are contemplated. The terms "antagonist", "inhibitor" and "antagomir" are used interchangeably herein.

A "disease" is defined as a pathological condition of a body part, an organ, or a system resulting from any cause, such as infection, genetic defect, or environmental stress. A "health-related condition" is defined herein to refer to a condition of a body part, an organ, or a system that may not be pathological, but for which treatment is sought. Examples include conditions for which therapy is sought, such as diabetes, obesity, high cholesterol and the like. The disease can be any disease, and non-limiting examples include diabetes mellitus, dyslipidemia, obesity, high cholesterol, and metabolic syndrome.

As used herein, the phrases "treating and/or preventing" or "treatment and/or prevention" includes the administration of the compositions, compounds or agents of the invention to prevent or delay the onset of the symptoms, complications, or biochemical indicia of a disease, alleviating or ameliorating the symptoms or arresting or inhibiting further development of the disease, condition, or disorder (e.g., obesity). "Treating and/or preventing" further refers to any indicia of success in the treatment or amelioration or prevention of the disease, condition, or disorder, including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms can be based on objective or subjective parameters; including the results of an examination by a physician. Accordingly, the phrase "treating and/or preventing" includes the administration of the therapeutic agents of the disclosure to prevent or delay, to alleviate, or to arrest or inhibit development of the symptoms or conditions associated with obesity, diabetes mellitus and dyslipidemia.

A "therapeutically effective amount" of a substance/molecule may vary according to factors such as the disease state, age, sex, and weight of the individual, and the ability of the substance/molecule to elicit a desired response in the individual. A therapeutically effective amount is also one in which any toxic or detrimental effects of the substance/molecule are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

By "reduce or inhibit" is meant the ability to cause an overall decrease of 20%, 30%, 40%, 50%, 60%, 70%, 75%, 80%, 85%, 90%, 95%, or greater. Reduce or inhibit can refer to the symptoms of the disorder being treated, the presence or size of metastases, or the size of the primary tumor.

It is specifically contemplated that any limitation discussed with respect to one embodiment of the invention may apply to any other embodiment of the invention. Furthermore, any composition of the invention may be used in any method of the invention, and any method of the invention may be used to produce or to utilize any composition of the invention.

The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, the methods and systems of the present invention that "comprises," "has," "includes" or "contains" one or more elements possesses those one or more elements, but is not limited to possessing only those one or more elements. Likewise, an element of a method or system of the present invention that "comprises," "has," "includes" or "contains" one or more features possesses those one or more features, but is not limited to possessing only those one or more features.

Any method or system of the present invention can consist of or consist essentially of—rather than comprise/include/contain/have—any of the described elements and/or features and/or steps. Thus, in any of the claims, the term "consisting of" or "consisting essentially of" can be substituted for any of the open-ended linking verbs recited above, in order to change the scope of a given claim from what it would otherwise be using the open-ended linking verb.

Throughout this application, the term "about" is used to indicate that a value includes the standard deviation of error for the device and/or method being employed to determine the value.

The term "substantially" is defined as being largely but not necessarily wholly what is specified (and include wholly what is specified) as understood by one of ordinary skill in the art. In any disclosed embodiment, the term "substantially" may be substituted with "within [a percentage] of" what is specified, where the percentage includes 0.1, 1, 5, and 10 percent.

As used herein, in the specification, "a" or "an" may mean one or more, unless clearly indicated otherwise. As used herein, in the claim(s), when used in conjunction with the word "comprising," the words "a" or "an" may mean one or more than one. As used herein "another" may mean at least a second or more.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 1 Prediction of miRNAs conserved pairing to the 3'UTR region of KDM3A and other thermogenic genes (SEQ ID NOS:5-10).

FIG. 2 Sixty putative target genes of miR-22-3p involved in lipid metabolism, oxidative phosphorylation, mitochondrial functions, respiratory cycle, browning of adipocytes and thermogenesis.

FIG. 3A In vitro validation of miRNA candidates in primary cultures of human subcutaneous adipocytes. FIG. 3B mRNA profiling of primary cultures of human subcutaneous adipocytes in the presence of a miR-22-3p inhibitor. FIG. 3C Activation of the PPAR pathway in primary cultures of human subcutaneous adipocytes in the presence of a miRNA 22-3p inhibitor (Kyoto Encyclopedia of Genes and Genomes (KEGG) resource).

FIG. 4A Body weight profile of C57Bl/J6 young male mice on 60% high fat diet alone (saline, black dotted line) or in the presence of a scrambled miRNA inhibitor (gray line) or a miR-22-3p inhibitor (black line) during 8 weeks of treatment, starting at week 6 of age. FIG. 4B Body composition by NMR analysis of C57Bl/J6 young male mice on 60% high fat diet alone (saline, gray columns) or in the presence of a scrambled miRNA inhibitor (black columns) or a miR-22-3p inhibitor (red columns) at week 4 of treatment, starting at week 6 of age.

FIG. 5A Body weight profile of C57Bl/J6 adult male mice on 10% high fat diet alone (saline 10% fat, gray line) or on 60% high fat diet alone (saline 60% fat, black dotted line) or in the presence of a miR-22-3p inhibitor (black solid line) during 8 weeks of treatment, starting at week 14 of age. FIG. 5B Representative pictures of 22-week old C57Bl/J6 adult male mice on normal diet (left picture), 60% high fat diet alone (right picture) or 60% high fat diet on miR-22-3p inhibitor (middle picture) at the end of 8 weeks of treatment. Average body weight per group is represented under each corresponding picture. FIG. 5C Body composition measure by NMR analysis at week 1 of C57Bl/J6 adult male mice switched at week 13 to a 10% fat diet and receiving saline injections (gray columns) or kept on 60% high fat diet and receiving saline injections (black columns) or kept on 60% high fat diet and receiving a miR-22-3p inhibitor (red columns) during 8 weeks of treatment, starting at week 14 of age. FIG. 5D Body composition measure by NMR analysis at week 4.

FIG. 6A Body weight profile of C57Bl/J6 adult male mice on 60% high fat diet alone (saline, dotted line) or in the presence of a custom-designed miR-22-3p inhibitor (solid line) during 6 weeks of treatment, starting at week 14 of age. FIG. 6B H&E staining of various fat tissues of 22-week old C57Bl/J6 adult male mice on 60% high fat diet alone (saline) or 60% high fat diet plus miR-22-3p inhibitor (APT-110) at the end of 6 weeks of treatment.

FIG. 7A Oxygen Consumption Rate (OCR) of human adipocytes cultured in the presence of BSA or the PPARG agonist rosiglitazone (100 nM) under basal conditions (a), then after successive additions of oligomycin (ATP turnover (b) and protein leak (c)), FCCP (Maximum respiration), and Rotenone/Antimycin A (Non-mitochondrial respiration). The value recorded after the final addition (dotted line e) was subtracted from the other values. FIG. 7B is a bar graph depicting relative OCR values for BSA and rosiglitazone-treated adipocytes. FIG. 7C Oxygen Consumption Rate (OCR) of human adipocytes cultured in the presence of the PPARG agonist rosiglitazone (100 nM) alone or in the presence of palmitate (utilization of exogenous fatty acids) or palmitate plus etomoxir (Carnitine palmitoyl transferase-1 inhibitor). FIG. 7D is a bar graph depicting relative OCR values for adipocytes treated with BSA, rosiglitazone, rosiglitazone+palmitate, or rosiglitazone+palmitate+etomoxir. FIG. 7E Oxygen Consumption Rate (OCR) of human adipocytes cultured in the presence of the mir-22-3p inhibitor APT-110 alone or in the presence of palmitate (utilization of exogenous fatty acids) or palmitate plus etomoxir (Carnitine palmitoyl transferase-1 inhibitor). FIG. 7F is a bar graph depicting relative OCR values for adipocytes treated with BSA, mir-22-3p inhibitor APT-110, APT-110+palmitate, or APT-110+palmitate+etomoxir.

FIG. 10A Energy expenditure measured on day 10. FIG. 10B Energy expenditure measured on day 11. FIG. 10C Energy expenditure measured on day 28. FIG. 10D Energy expenditure measured on day 52.

DETAILED DESCRIPTION

Figures 3A, 3B:
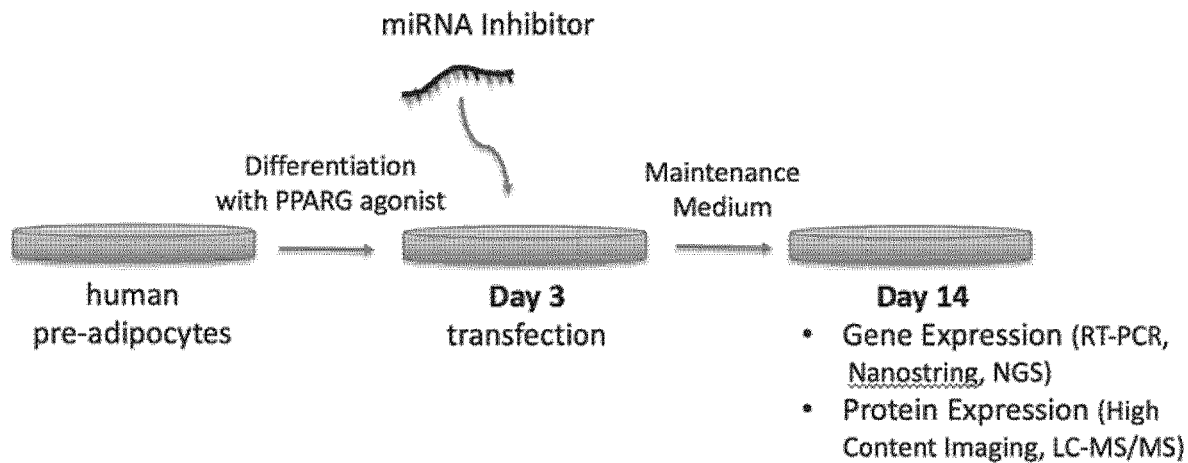
FIGS. 3A-3C.

Mir-22 is an upstream regulator of a series of genes involved in metabolism. Pharmacological attenuation of mir-22 activity provides an approach for positively affecting a series of metabolic outcomes.

It is well established that adipose tissues play a pivotal role in regulating energy balance (Cinti, S., 2012). Experimental evidence has demonstrated that subcutaneous white adipocytes (scWAT) can evolve into calories-burning "beige" or "brite" adipocytes (Cohen, P., et al., 2015, and Sharp., et al., 2012). Mitochondrial uncoupling protein 1 (UCP1), also named thermogenin, is responsible for thermogenesis in brown adipose tissue (BAT) and heat dissipation by uncoupling oxidative phosphorylation from ATP synthesis (Rousset, S., et al., 2004). Activation of UCP1 in various tissues may provide a promising approach for enhancing energy expenditure and combating obesity-related disorders.

Increase of energy expenditure is an effective treatment for obesity and related disorders. Specific miRNAs are involved in a variety of metabolic functions, including adipogenesis, obesity, browning of adipocytes, insulin resistance, lipid and glucose metabolism and have been shown to be dysregulated in various cardiometabolic diseases [24-29].

UCP1 biosynthesis is mainly controlled at the transcription level. The promoter region of the UCP1 gene contains many distinct regulatory sites, allowing a wide range of molecules to modulate its transcription (Del Mar Gonzalez-Barroso et al. 2000. Of importance is the high degree of methylation of the UCP1 gene promoter region (Shore, A., et al., 2010). The human lysine (K)-specific demethylase 3A (KDM3A) regulates the expression of metabolic genes and obesity resistance (Tateishi, K., et al., 2009). KDM3A directly regulates peroxisome proliferator-activated receptor alpha (PPARA) and UCP1 expression. KDM3A gene expression is regulated by mir-22 microRNA. Inhibition of miR-22 leads to the upregulation of KDM3A, thereby increasing demethylation of the UCP1 gene promoter region, and increasing expression of UCP1. Pharmacological inhibition of mir-22 is therefore an approach to affect meaningful changes in metabolism and thermogenesis.

A. Increasing Energy Expenditure

Obesity is the result of a chronic imbalance between energy intake and expenditure. Increasing energy expenditure alters the imbalance and leads to a net loss of weight.

Mammalian adipocytes can be categorized into two major categories based on their functional profiles: 1) White adipocytes (WAT) that store energy in the form of triglyceride lipids and; 2) Brown adipocytes (BAT) that are rich in mitochondria and expend energy via uncoupled fatty oxidation. It is well-established that adipose tissues play a pivotal role in regulating energy balance (Cinti, S., 2012). Regarding the distribution and activity of BAT in adult humans: 1) multiple depots of BAT are present in the cervical, supraclavicular, axillary and paravertebral regions in adult subjects; 2) BAT in adult humans can be rapidly activated by exposure to cold temperatures; 3) there is an inverse correlation between the activity of BAT and age, body-mass index (BMI), the percentage of body fat, fasting plasma glucose level, beta-blocker use and outdoor temperature; 4) BAT expansion may drive the weight loss associated with catecholamine-producing phaeochromocytomas; 5) Beta3-adrenoreceptor polymorphisms leading to a reduction in receptor function have been linked to weight gain and early onset type 2 diabetes mellitus (Virtanen, K. A., 2013).

Recently, experimental evidence demonstrated that subcutaneous white adipocytes (scWAT) can evolve into calories-burning "beige" or "brite" adipocytes (Cohen, P. et al., 2015; Sharp, L. Z., et al., 2012).

Thus, promoting brown-like transformation in subcutaneous WAT is a promising strategy for combating human obesity and its related cardiometabolic problems (Wu, J., et al., 2013).

Mitochondrial uncoupling proteins (UCP) are members of the family of mitochondrial anion carrier proteins (MACP) (Collins, S. et al., 2010). UCPs dissociate ("uncouple") oxidative phosphorylation from ATP synthesis, which results in energy dissipated as heat (also referred to as the "mitochondrial proton leak"). UCPs facilitate the transfer of anions from the inner to the outer mitochondrial membrane and the return transfer of protons from the outer to the inner mitochondrial membrane generating heat in the process. UCPs are the primary proteins responsible for thermogenesis and heat dissipation (Mozo, J., et al., 2005). UCP1, also named thermogenin, is responsible for thermogenesis in BAT and heat dissipation, whereas UCP2 is ubiquitous and UCP3 is muscle-specific. UCP1 biosynthesis is mainly controlled at the transcription level. The promoter region of the UCP1 gene contains many distinct regulatory sites, allowing a wide range of molecules to modulate its transcription. Of importance is the high degree of methylation ("CG islands") of the promoter region of the UCP1 gene (Shore, A., et al., 2010). Methylation of CG islands within gene promoters can lead to their silencing. Conversely, in most instances the CG islands of promoters are unmethylated when genes are expressed.

The human lysine (K)-specific demethylase 3A (KDM3A, also known as JHDM2a) is critically important in regulating the expression of metabolic genes and obesity resistance, as demonstrated by Yi Zhang et al (Tateishi, K., et al., 2009; Okada, Y. et al., 2010).

JHDM2a regulates metabolic genes related to energy homeostasis including adipogenesis, regulation of fat storage, glucose transport and type 2 diabetes mellitus. Mice deficient in JHDM2a (JHDM2a-/-) develop adult onset obesity, hypertriglyceridemia, hypercholesterolemia, hyperinsulinemia and hyperleptinemia, which are hallmarks of the metabolic syndrome. JHDM2a-/- mice furthermore exhibit fasted induced hypothermia, indicating reduced energy expenditure. They also have a higher respiratory quotient indicating less fat utilization for energy production.

JHDM2a possesses organ/tissue-specific target genes, and impairment of this molecule cannot be compensated by other JmjC-containing histone demethylases, suggesting the importance of this molecule in vivo. KDM3A (JHDM2a) plays a role in regulating fat metabolic gene expression in muscle and brown fat tissue, as KDM3A knockout mice were revealed to exhibit obesity and hyperlipidemia (Okada, Y. et al., 2010).

KDM3A directly regulates peroxisome proliferator-activated receptor alpha (PPARA) and UCP1 expression. Beta-adrenergic stimulation of KDM3A expression and binding to the PPAR responsive element (PPRE) of the UCP1 gene not only decreases levels of H3K9me2 (dimethylation of lysine 9 of histone H3) at the PPAR Response Element (PPRE), but also facilitates the recruitment of PPARG and RXRA and their co-activators PPARGC1A, CREBBP and NCOA1 to the PPRE. The loss of KDM3A functions disrupts beta-adrenergic-stimulation of glycerol release and oxygen consumption in brown fat, resulting in enlargement and accumulation of lipid droplets. KDM3A loss of function also decreases fat oxidation and glycerol release in skeletal muscles. By employing microarray technology, Zhang et al. demonstrated that a significant proportion of the genes involved in PPAR signaling, fatty acid oxidation and thermogenesis (e.g. PPARA, PPARG, ACADM, ACADL, ACADVL, ACOX2, AQP7, UCP1) were down-regulated in response to KDM3A knockout ($p \leq 1^{-11}$) (Tateishi, K., et al., 2009).

As a class of new therapeutic agents (Li, Z. and T. M. Rana, 2014), microRNA analogs have several potential clinical advantages for the chronic treatment of cardiometabolic diseases, including: convenient once-weekly subcutaneous self-injections in the abdomen, improved patient adherence to treatment, fat mass reduction ≥15% meeting patients' expectations and exceeding regulatory requirements, increased calorie expenditure even in the absence of diet and exercise changes, improved glucose, insulin and cholesterol profile, reduced liver fatty infiltration, no adverse events at the level of the brain (e.g. depression, suicidality), cardiovascular system (e.g. tachycardia and hypertension) and digestive tract (e.g. malabsorption and diarrhea), better quality of life and limited drug-drug interactions The degree of methylation of the promoter regions of various genes, like PPARA and UCP1, involved in metabolism and thermogenesis is under the control of demethylases like KDM3A and KDM6B. Removal of miR-22 inhibition of these demethylases expression by a miR-22 inhibitor results in meaningful changes in metabolism and thermogenesis. Data indicate that miR-22 is highly expressed in human subcutaneous adipocytes (Liang, Y., et al., 2007). Therefore, introduction of a miR-22 inhibitor into human subcutaneous adipocytes should prevent the endogenous miR-22 from down-regulating gene expression. Opposite to the KDM3A knockout or knock-down experiments that produced obesity and metabolic disorders, expression and activation of KDM3A and KDM6B leads to reduction of obesity and improvement of metabolic parameters.

Initial in silico work identified miR-22 as a candidate to investigate in the context of obesity and related metabolic disorders. The experiments and studies performed in vitro and in vivo demonstrate that miR-22-3p inhibition activates the PPARA pathway with stimulation of lipid metabolism, fatty acid oxidation and thermogenesis in human subcutaneous adipocytes, reduces the accumulation of fat in the mouse model of diet induced obesity as tested in animals of various ages, modifies the phenotype of adipocytes with cellular size reduction, increase of mitochondrial mass/activity and UCP1 expression (the "Browning Effect"), increases energy expenditure, has a dramatic effect on glucose homeostasis and insulin sensitivity, reduces levels of circulating cholesterol, and alters favorably the release of adipokines (reduction of pro-inflammatory leptin while anti-inflammatory adiponectin remains steady. These metabolic benefits were observed even though the animals consumed the same amount of high fat diet and no hyperthermia was recorded.

In transgenic mice with enhanced cardiac expression of miR-22, the expression of PPARA, PPARGC1A and SIRT1 (all involved in energy substrate metabolism) was repressed [30]. Furthermore, the results represent the opposite pattern of what was observed in KDM3A knockout mice in regards to the expression of genes involved in PPAR signaling, fatty acid oxidation and thermogenesis (Tateishi, K., et al., 2009).

B. Oligonucleotides

The term "nucleotide" refers to a nucleoside having a phosphate group on its 3' or 5' sugar hydroxyl group. The term "nucleoside" refers to a unit made up of a heterocyclic base and its sugar. Thus nucleosides, unlike nucleotides, have no phosphate group. "Oligonucleotide" refers to a plurality of joined nucleotide units formed in a specific sequence from naturally occurring bases and pentofuranosyl groups joined through a sugar group by native phosphodiester bonds. This term refers to both naturally occurring and synthetic species formed from naturally occurring subunits.

The presently disclosed compounds generally can be viewed as "oligonucleotide analogs", that is, compounds which function like oligonucleotides but which have non-naturally occurring portions. Oligonucleotide analogs can have altered sugar moieties, altered base moieties or altered inter-sugar linkages. An oligonucleotide analog having non-phosphodiester bonds, i.e., an altered inter-sugar linkage, is considered to be an "oligonucleoside." The term "oligonucleoside" thus refers to a plurality of nucleoside units joined by linking groups other than native phosphodiester linking groups. The term "oligomers" is intended to encompass oligonucleotides, oligonucleotide analogs or oligonucleosides. Thus, in speaking of "oligomers" reference is made to a series of nucleosides or nucleoside analogs that are joined via either natural phosphodiester bonds or other linkages, including the four atom linkers. Although the linkage generally is from the 3' carbon of one nucleoside to the 5' carbon of a second nucleoside, the term "oligomer" can also include other linkages such as 2'-5' linkages.

Oligonucleotide analogs also can include other modifications, particularly modifications that increase nuclease resistance, improve binding affinity, and/or improve binding specificity. For example, when the sugar portion of a nucleoside or nucleotide is replaced by a carbocyclic moiety, it is no longer a sugar. Moreover, when other substitutions, such a substitution for the inter-sugar phosphorodiester linkage are made, the resulting material is no longer a true nucleic acid species. All such compounds are considered to be analogs. Throughout this specification, reference to the sugar portion of a nucleic acid species shall be understood to refer to either a true sugar or to a species taking the structural place of the sugar of wild type nucleic acids. Moreover, reference to inter-sugar linkages shall be taken to include moieties serving to join the sugar or sugar analog portions in the fashion of wild type nucleic acids.

The present disclosure concerns modified oligonucleotides, i.e., oligonucleotide analogs or oligonucleosides, and methods for effecting the modifications. These modified oligonucleotides and oligonucleotide analogs may exhibit increased chemical and/or enzymatic stability relative to their naturally occurring counterparts. Extracellular and intracellular nucleases generally do not recognize and therefore do not bind to the backbone-modified compounds. When present as the protonated acid form, the lack of a negatively charged backbone may facilitate sequence specific binding of the oligonucleotide analogs or oligonucleosides to targeted RNA.

The modified internucleoside linkages are intended to replace naturally-occurring phosphodiester-5'-methylene linkages with four atom linking groups to confer nuclease resistance and enhanced cellular uptake to the resulting compound. Preferred linkages have structure CH2-RA-NR1 CH2, CH2-NR1-RA-CH2, RA-NR1-CH2-CH2, CH2-CH2-NR1-RA, CH2-CH2-RA-NR1, or NR1-RA-CH2-CH2 where RA is O or NR2.

Methods for the preparation of oligonucleosides are disclosed. Modifications may be effected using solid supports which may be manually manipulated or used in conjunction with a DNA synthesizer using methodology commonly known to those skilled in DNA synthesizer art. Generally, the procedure involves functionalizing the sugar moieties of two nucleosides which will be adjacent to one another in the selected sequence. In a 5' to 3' sense, an "upstream" synthon such as structure H is modified at its terminal 3' site, while a "downstream" synthon such as structure H1 is modified at its terminal 5' site.

Oligonucleosides linked by hydrazines, hydroxylamines and other linking groups, can be protected by a dimethoxytrityl group at the 5'-hydroxyl and activated for coupling at the 3'-hydroxyl with cyanoethyldiisopropyl-phosphite moieties. These compounds can be inserted into any desired sequence by standard, solid phase, automated DNA synthesis techniques. One of the most popular processes is the phosphoramidite technique [52], wherein a nucleoside or oligonucleotide having a free hydroxyl group is reacted with a protected 2'-cyanoethyl phosphoramidite monomer or oligomer in the presence of a weak acid to form a phosphite linked structure. Oxidation of the phosphite linkage followed by hydrolysis of the cyanoethyl group yields the desired phosphate or phosphorothioate linkage.

Oligonucleotides containing a uniform backbone linkage can be synthesized by use of CPG-solid support and standard nucleic acid synthesizing machines such as Applied Biosystems Inc. 380B and 394 and Milligen/Biosearch 7500 and 8800s. The initial nucleotide (number 1 at the 3'-terminus) is attached to a solid support such as controlled pore glass. In sequence specific order, each new nucleotide is attached either by manual manipulation or by the automated synthesizer system.

Free amino groups can be alkylated with, for example, acetone and sodium cyanoboro hydride in acetic acid. The alkylation step can be used to introduce other, useful, functional molecules on the macromolecule. Such useful functional molecules include but are not limited to reporter molecules, RNA cleaving groups, groups for improving the pharmacokinetic properties of an oligonucleotide, and groups for improving the pharmacodynamic properties of an oligonucleotide. Such molecules can be attached to or conjugated to the macromolecule via attachment to the nitrogen atom in the backbone linkage. Alternatively, such molecules can be attached to pendent groups extending from a hydroxyl group of the sugar moiety of one or more of the nucleotides. Examples of such other useful functional groups are provided by U.S. patent application Ser. No. 782,374, entitled Derivatized Oligonucleotides Having Improved Uptake & Other Properties, assigned to the same assignee as this application, herein incorporated by reference, and in other of the above-referenced patent applications.

Solid supports may include any of those known in the art for polynucleotide synthesis, including controlled pore glass (CPG), oxalyl controlled pore glass Alul, et al., 1991.

TentaGel Support—an aminopolyethyleneglycol derivatized support (Wright, et al., 1993) or Poros—a copolymer of polystyrene/divinylbenzene. Attachment and cleavage of nucleotides and oligonucleotides can be effected via standard procedures (Pon, R. T., 1993).

As used herein, the term solid support further includes any linkers (e.g., long chain alkyl amines and succinyl residues) used to bind a growing oligonucleoside to a stationary phase such as CPG.

C. Compositions Comprising miRNA Modulators

The compositions of the disclosure may comprise compounds of the disclosure combined with one or more carrier/ targeting elements (e.g., any of the targeting agents described herein) to enhance specific cellular uptake, cellular distribution, and/or cellular activity of the compound. The compounds of the disclosure may directly or indirectly reprograms mesenchymal stem cells (ATMSCs) or white adipocytes (WAT) to become brown adipocytes (BAT) or beige adipocytes. The compounds can act directly on a target gene or on an activator or repressor of a target gene, or on a target miRNA that directly or indirectly modulates the activity of a thermogenic regulator (e.g., a mitochondrial uncoupler or an activator or repressor thereof). As used herein, the term "mitochondrial uncoupler" refers to a protein (or the encoding nucleic acid) that can dissipate of the mitochondrial inner membrane proton gradient, thereby preventing the synthesis of ATP in the mitochondrion by oxidative phosphorylation. Exemplary mitochondrial uncouplers include UCP1, UCP2 and UCP3.

In some embodiments, a compound of the disclosure is linked (covalently or non-covalently) to a fatty acid or the targeting agent (e.g., aptamer). In other embodiments, a compound of the disclosure is admixed with the targeting element in a single composition (e.g., in a liposome, exosome or nanoparticle formulation).

1. AptamiR Compositions

In certain exemplary embodiments, a compound of the disclosure is combined with an aptamer to create an "AptamiR" composition. There are many different ways to combine an aptamer and a compound to create an aptamir. They include, for example, aptamer-compound chimeras, aptamer-splice-switching oligonucleotide chimeras, and aptamer conjugated to nanoparticles or exosomes containing the compound.

Aptamers are usually single-stranded, short molecules of RNA, DNA or a nucleic acid analog, that may adopt three-dimensional conformations complementary to a wide variety of target molecules. Methods of constructing and determining the binding characteristics of aptamers are well known in the art. For example, such techniques are described in U.S. Pat. Nos. 5,582,981, 5,595,877 and 5,637,459, each incorporated herein by reference.

Aptamers may be prepared by any known method, including synthetic, recombinant, and purification methods, and may be used alone or in combination with other ligands specific for the same target. In general, a minimum of approximately 3 nucleotides, preferably at least 5 nucleotides, are necessary to effect specific binding. Aptamers of sequences shorter than 10 bases may be feasible, although aptamers of 10, 20, 30 or 40 nucleotides may be preferred.

Aptamers need to contain the sequence that confers binding specificity, but may be extended with flanking regions and otherwise derivatized. In preferred embodiments, the target-binding sequences of aptamers may be flanked by primer-binding sequences, facilitating the amplification of the aptamers by PCR or other amplification techniques. In a further embodiment, the flanking sequence may comprise a specific sequence that preferentially recognizes or binds a moiety to enhance the immobilization of the aptamer to a substrate.

Aptamers may be isolated, sequenced, and/or amplified or synthesized as conventional DNA or RNA molecules. Alternatively, aptamers of interest may comprise modified oligomers. Any of the hydroxyl groups ordinarily present in aptamers may be replaced by phosphonate groups, phosphate groups, protected by a standard protecting group, or activated to prepare additional linkages to other nucleotides, or may be conjugated to solid supports. One or more phosphodiester linkages may be replaced by alternative linking groups, such as P(O)O replaced by P(O)S, P(O)NR2, P(O)R, P(O)OR', CO, or CNR2, wherein R is H or alkyl (1-20C) and R' is alkyl (1-20C); in addition, this group may be attached to adjacent nucleotides through O or S. Not all linkages in an oligomer need to be identical.

Methods for preparation and screening of aptamers that bind to particular targets of interest are well known, for example U.S. Pat. Nos. 5,475,096 and 5,270,163, each incorporated by reference. The technique generally involves selection from a mixture of candidate aptamers and stepwise iterations of binding, separation of bound from unbound aptamers and amplification. Because only a small number of sequences (possibly only one molecule of aptamer) corresponding to the highest affinity aptamers exist in the mixture, it is generally desirable to set the partitioning criteria so that a significant amount of aptamers in the mixture (approximately 5-50%) are retained during separation. Each cycle results in an enrichment of aptamers with high affinity for the target. Repetition for between six to twenty selection and amplification cycles may be used to generate aptamers that bind with high affinity and specificity to the target. Aptamers may be selected to specifically bind to adipocytes and related cells.

In one embodiment, an aptamiR composition comprises an aptamer that is directly linked or fused to a compound of the disclosure. Such aptamiRs are entirely chemically synthesized, which provides more control over the composition of the conjugate. For instance, the stoichiometry (ratio of compound per aptamer) and site of attachment can be precisely defined. The linkage portion of the conjugate presents a plurality (2 or more) of nucleophilic and/or electrophilic moieties that serve as the reactive attachment point for the aptamers and compounds of the disclosure. In addition, the aptamir may further comprise a linker between the aptamer and the compound. In some embodiments, the linker is a polyalkylene glycol, particularly a polyethylene glycol. In other embodiments, the linker is a exosome, dendrimer, or comb polymer. Other linkers can mediate the conjugation between the aptamer and the compound, including a biotinstreptavidin bridge, or a ribonucleic acid. Exemplary non-covalent linkers include linkers formed by base pairing a single stranded portion or overhang of the miRNA element and a complementary single-stranded portion or overhang of the aptamer element.

2. ExomiR Composition

In a further particular embodiment, an aptamer is combined with a compound of the disclosure in the form of a carrier-based aptamiR, described as an "ExomiR". Exemplary carriers include liposomes, nanoparticles, or exosomes. Nanoparticle approaches have several functional advantages, including, for example, cellular uptake, the ability to cross membranes, and triggered nanoparticle disassembly. In some embodiments, the miRNA agent is encapsulated within the nanoparticle exosome. In some embodiments, the targeting agent is bound to the outside of the nanoparticle. The nano particle is no more than 100 nm in diameter.

In a particular embodiment, an aptamer is anchored at the surface of an exosome containing a load of active ingredient (i.e. compound of the disclosure). Exosomes are spherical nanostructures made of a lipid bilayer that can be loaded with pharmaceuticals, such as miRNAs.

Exosomes were first described as a means for reticulocytes to selectively discard transferrin receptors as they matured into erythrocytes (Johnstone, et al., 1987). For a long time thereafter, they were seen as mere 'garbage cans' for the removal of unwanted cellular components. However, since the discovery that B cells shed exosomes containing antigen-specific MHC II capable of inducing T cell responses (Raposo, et al., 1996), an abundance of exosome research has revealed that these small vesicles are involved in a multitude of functions, both physiological and pathological.

Exosomes are small membrane vesicles of endocytic origin that are secreted by many cell types. For example, exosomes may have a diameter of about 30 to about 100 nm. They may be formed by inward budding of the late endosome leading to the formation of vesicle-containing multivesicular bodies (MVB) which then fuse with the plasma membrane to release exosomes into the extracellular environment. Though their exact composition and content depends on cell type and disease state, exosomes all share certain structural characteristics.

In certain aspects, the exosomes may be purified by ultracentrifugation in a sucrose gradient, then identified by the presence of marker proteins such as Alix and CD63 (Schorey & Bhatnagar, 2008) or enrichment of tetraspanins and heat shock protein 70 (Lee, et al., 2011), all of which are specifically expressed in exosomes.

Exosomes also have the potential for directional homing to specific target cells, dependent on the physical properties of their membranes. Their effect can be local, regional or systemic. Exosomes do not contain a random sampling of their parent cell's cytoplasm, but are enriched in specific mRNA, miRNA, and proteins (Bobrie, et al., 2011). This cargo is protected from degradation by proteases and RNases while the vesicle is in the interstitial space, and retains bioactivity once taken up by a recipient cell. In this way, they facilitate the transfer of interactive signaling and enzymatic activities that would otherwise be restricted to individual cells based on gene expression (Lee, et al., 2011). For example, Skog and coworkers show that mRNA for a reporter protein can be incorporated into exosomes, transferred to a recipient cell, and translated (Skog, et al., 2008).

Selective purification or enrichment of physiologically active subpopulations of exosomes may be achieved via several procedures. In certain embodiments, effective exosomes may be concentrated to an enriched sample via use of specific surface protein markers and related separation techniques. In other embodiments, effective exosomes may be harvested from enriched primary cells cultures identified as capable of producing the effective exosomes. In further embodiments, based on screening procedures used to identify candidate effective exosome species, other exosomes may be fabricated using molecular engineering strategies designed to selectively produce exosomes containing the target (i.e., postulated) therapeutic molecular species. The latter may be confirmed by application of exosomes containing fabricated species to naïve cultures, where the desired effect (e.g., increased myelination) may be verified.

The exosome surface can be loaded with different substances, such as polyethylene glycol (extending their systemic half life) or molecular recognition elements like aptamers for specific binding and fusion to targeted cells. For example, aptamer-modified exosomes have been developed, with each exosome displaying approximately 250 aptamers tethered to its surface to facilitate target binding.

Glycosylphosphatidylinositol-anchored adiposomes transfer antilipolytic compounds from large donor adipocytes to small acceptor adipocytes.

In a preferred embodiment, exosomes are created to encapsulate compound(s) and display at their surface aptamers that specifically bind with high affinity and specificity to molecules (e.g. lipid transporters) highly expressed at the surface of adipocytes and ATMSCs. The fusion of the exosomes with the targeted cells causes the release of the compound(s) into the cell cytoplasm, which then alter a specific intra-cellular pathway. Alternatively, stable thio-aptamers may be inserted at the surface of exosomes to guide delivery of the exosome compound(s) load to targeted ATMSCs and adipocytes.

Exosomes are naturally occurring biological membrane vesicles measuring 30 to 100 nm that are secreted by most cells. They display surface receptors/molecules for cell targeting, adhesion and fusion, and also contain lipids, proteins, mRNAs and miRNAs. Exosomes are involved in the transport of genetic material while preserving it from circulating nucleases, the modulation of the immune system and cell-to-cell communications. Exosomes and their cargo load can efficiently cross barriers such as the skin, the intestinal mucosae and the blood-brain barrier. Exosomes are not recognized by macrophages, are not subject to attack by opsonins, complement factors, coagulation factors or antibodies in the circulation. They do not trigger innate immune reactions and are not cytotoxic.

Being natural shuttles of functional miRNAs, exosomes represent novel nano-scale delivery vehicles of compounds directly into the cytosol of target cells, as an alternative to liposomes. For instance, human breast milk exosomes contain 602 unique mature miRNAs which can be transferred from the mother to her infant (Zhou, 2012).

Exosomes released by "donor adipocytes", which harbor glycosylphosphatidylinositol (GPI)-anchored proteins like Gce-1 and CD73, can specifically transfer mRNAs and miRNAs to "acceptor adipocytes" where they modulate lipogenesis and cell size (Müller, 2011). Such paracrine and endocrine regulation of adipocyte functions and size represents a novel therapeutic approach to metabolic diseases such as obesity and metabolic syndrome.

Such carrier-based aptamir compositions have the capability of delivering a cargo of a load comprising one or more compounds of the disclosure to the target cell in a single carrier. To accomplish targeting and accumulation, the carriers are formulated to present the targeting element on their external surface so they can react/bind with selected cell surface antigens or receptors on the adipose target cell. As an example, carriers may be created to encapsulate compounds of the disclosure while displaying at their surface aptamers that specifically bind with high affinity and specificity to molecules (e.g. lipid transporters) highly expressed at the surface of adipocytes and ATMSCs. The internalized exosomes release inside the cell cytoplasm their compound(s) load, which alters a specific intra-cellular pathway.

In one embodiment, the carrier is an exosome. Exosomes, which originate from late endosomes, are naturally occurring nanoparticles that are specifically loaded with proteins, mRNAs, or miRNAs, and are secreted endogenously by cells. Exosomes are released from host cells, are not cytotoxic, and can transfer information to specific cells based on their composition and the substance in/on the exosome. Because exosomes are particles of approximately 30-100 nm in diameter, the exosomes evade clearance by the mononuclear phagocyte system (which clears circulating particles >100 nm in size), and are very efficiently delivered to target tissues.

Moreover, synthetic exosomes may offer several advantages over other carriers. For example, they may deliver their cargo directly into the cytosol, while their inertness avoids immune reactions and clearance in the extracellular environment. The structural constituents of exosomes may include small molecules responsible for processes like signal transduction, membrane transport, antigen presentation, targeting/adhesion, among many others.

3. Liposome Delivery Systems

Certain aspects of the disclosure relate to liposome delivery systems that target adipose tissues. A liposome is a spherical vesicle having at least one lipid bilayer. The liposome can be used as a vehicle for administration of therapeutic agents such as the compounds of the disclosure, nucleic acids, polypeptides, antibodies, small molecules, and molecules described in the disclosure. Liposomes are most often composed of phospholipids that are compatible with a lipid bilayer structure.

The major types of liposomes are the multilamellar vesicle (MLV, with several lamellar phase lipid bilayers), the small unilamellar liposome vesicle (SUV, with one lipid bilayer), the large unilamellar vesicle (LUV), and the cochleate vesicle. A less desirable form are multivesicular liposomes in which one vesicle contains one or more smaller vesicles. The liposomes of the disclosure may be comprised or consist essentially of, or consist of one or more of 1,2-dimyristoyl-sn-glycero-3-phosphocholine (DMPC), 1,2-Dimyristoyl-sn-glycero-3-phosphorylglycerol (DMPG), hydrogenated soybean phosphatidylcholine (HSPC), Cholesterol, Sphingomyelin, 1,2-Distearoyl-sn-glycero-3-phosphoglycerol (DSPG), LIPOVA-E120, LECIVA-570, LECIVA-590, 1,2-Dioleoyl-sn-glycero-3-phosphocholine (DOPC), 1,2-Dipalmitoyl-sn-glycero-3-phosphoglycerol (DPPG), Egg PG, 1,2-Dimyristoyl-sn-glycero-3-phosphocholine (DMPC), Leciva-S90, 1,2-Distearoyl-sn-glycero-3-phosphoethanolamine (DSPE), soybean oil, polysorbate 80, sphinogomyelin, and phosphatidylcholine. In some embodiments, the phospholipids in the liposome consists of a phospholipid described above.

The weight percentage of any one of the components in the liposome may be at least, at most, or exactly 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89 90 91, 92, 93, 94, 95, 96, 97, 98, 99, or 100 weight % (or any derivable range therein).

The diameter of the liposome may be at most, at least, or exactly 75, 80, 85, 90, 95, 100, 110, 120, 130, 140, 150, 160, 170, 180, 190, 200, 220, 230, 240, 250, 260, 270, 280, 290, 300, 320, 340, 360, 380, 400, 420, 440, 460, 480, 500, 525, 550, 575, 600, 625, 650, 676, 700, 750, 800, 850, 900, or 1000 nm (or any derivable range therein).

Embodiments of the disclosure are contemplated in which the liposomes specifically exclude any component described herein. In some embodiments, the liposomes consist essentially of a specified list of components. The term "consist essentially of" in this sense, excludes any additional molecules that provide structure to the liposome, but may include non-structural components.

Embodiments of the disclosure relate to liposomes, as described herein, and a therapeutic agent. The therapeutic agent may be a nucleic acid, a polypeptide, a small molecule, a compound of the disclosure, or a therapeutic agent-fatty acid conjugate described herein.

4. Nanoparticle Delivery of Therapeutic Agents

Certain aspects of the disclosure relate to nanoparticle delivery of a therapeutic agent (e.g., a compound of the disclosure, nucleic acid, genetic editing agent, polypeptide, or small molecule) to an adipocyte by combination of the therapeutic agent to nanoparticles. A nanoparticle is a particle whose one dimension in the nanometer (nm) range. Nanoparticles can be used as a vehicle for administration of therapeutic agents such as the compounds of the disclosure, nucleic acids, polypeptides, antibodies, small molecules, and molecules described in the disclosure.

The diameter of the nanoparticle may be at most, at least, or exactly 25, 30, 50, 75, 80, 85, 90, 95, 100, 110, 120, 130, 140, 150, 160, 170, 180, 190, 200, 300, 400, 500, 600, 700, 800, 900, or 950 nm (or any derivable range therein).

In some embodiments, the nanoparticles consist essentially of a specified list of components. The term "consist essentially of," in this sense, excludes any additional molecules that provide structure to the liposome, but may include non-structural components.

Embodiments of the disclosure relate to nanoparticles, as described herein, and a therapeutic agent. The therapeutic agent may be a nucleic acid, a gene editing agent, a polypeptide, a small molecule, a compound of the disclosure, or a therapeutic agent-fatty acid conjugate described herein.

5. Fatty Acid Delivery of Therapeutic Agents

In some embodiments, the disclosure provides for delivery of a therapeutic agent (e.g., a compound of the disclosure, nucleic acid (the "LipomiRs"), polypeptide, or small molecule) to an adipocyte by conjugation of the therapeutic agent to a fatty acid. In chemistry, particularly in biochemistry, a fatty acid is a carboxylic acid with a long aliphatic chain, which is either saturated or unsaturated. Most naturally occurring fatty acids have an unbranched chain of an even number of carbon atoms, from 4 to 28. Fatty acids are usually derived from triglycerides or phospholipids. Fatty acids that have carbon-carbon double bonds are known as unsaturated. Fatty acids without double bonds are known as saturated. They differ in length as well. In some embodiments, the fatty acid is an unsaturated fatty acid. In some embodiments, the fatty acid is a saturated fatty acid. Fatty acid chains differ by length, often categorized as short to very long. Short-chain fatty acids (SCFA) are fatty acids with aliphatic tails of fewer than six carbons (e.g., butyric acid). Medium-chain fatty acids (MCFA) are fatty acids with aliphatic tails of 6-12 carbons, which can form medium-chain triglycerides. Long-chain fatty acids (LCFA) are fatty acids with aliphatic tails 13 to 21 carbons. Very long chain fatty acids (VLCFA) are fatty acids with aliphatic tails longer than 22 carbons. In some embodiments, the fatty acids are short, medium, long, or very long chain fatty acids. In some embodiments, the fatty acids are short chain fatty acids. In some embodiments, the fatty acids are medium chain fatty acids. In some embodiments, the fatty acids are long chain fatty acids. In some embodiments, the fatty acids are very long chain fatty acids.

Unsaturated fatty acids have one or more double bonds between carbon atoms. The two carbon atoms in the chain that are bound next to either side of the double bond can occur in a cis or trans configuration. A cis configuration means that the two hydrogen atoms adjacent to the double bond stick out on the same side of the chain. The rigidity of the double bond freezes its conformation and, in the case of the cis isomer, causes the chain to bend and restricts the conformational freedom of the fatty acid. The more double bonds the chain has in the cis configuration, the less flexibility it has. When a chain has many cis bonds, it becomes quite curved in its most accessible conformations. For example, oleic acid, with one double bond, has a "kink" in it, whereas linoleic acid, with two double bonds, has a more pronounced bend. Alpha-linolenic acid, with three double bonds, favors a hooked shape. The effect of this is that, in restricted environments, such as when fatty acids are part of a phospholipid in a lipid bilayer, or triglycerides in lipid droplets, cis bonds limit the ability of fatty acids to be closely packed, and therefore can affect the melting temperature of the membrane or of the fat.

A trans configuration, by contrast, means that the adjacent two hydrogen atoms lie on opposite sides of the chain. As a result, they do not cause the chain to bend much, and their shape is similar to straight saturated fatty acids. In most naturally occurring unsaturated fatty acids, each double bond has three n carbon atoms after it, for some n, and all are cis bonds. Most fatty acids in the trans configuration (trans fats) are not found in nature and are the result of human processing (e.g., hydrogenation).

Fatty acids having from 8 to 52 carbon atoms are contemplated. Fatty acids include, for example, arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride, butyric acid, valeric acid, caproic acid, enanthic acid, pelargonic acid, undecylic acid, tridecylic acid, pentadecylic acid, heptadecylic acid, nonadecanoic acid, arachic acid, isocrotonic acid, undecylenic acid, elaidic acid, sorbic acid, decanoic, dodecanoic, docosanoic, and dotriacontahexaenoic.

6. Adipose-Specific Targeting

In some embodiments, the disclosure provides compositions and methods for targeted delivery of compounds to adipose tissue, e.g., white adipose tissue (WAT). Specifically, the goal is to selectively deliver compounds of the disclosure to adipose tissue. Human subcutaneous adipose tissue contains several cell types, any of which may be selectively targeted with the compositions of the invention. For example, in certain embodiments, the target cell is an adipocyte. In other embodiments, the target cell may be an adipocyte precursor such as a pre-adipocyte or adipose tissue mesenchymal stem cell (ATMSC). ATMSCs possess the ability to differentiate into multiple lineages, such as adipocytes, osteocytes, and chondrocytes and are present in human subcutaneous adipose tissue in appreciable quantities. Human ATMSCs can be reprogrammed to become brown adipocytes (BAT) via modulation of a defined set of transcription factors.

In certain embodiments, the compositions of the disclosure bind to an adipose-target cell comprising one or more ATMSC-positive surface markers. Exemplary ATMSC-positive surface markers include CD9 (tetraspan), CD10

(MME), CD13 (ANPEP), CD29 (β-1 integrin), CD36 (FAT), CD44 (hyaluronate), CD49d (α-4 integrin), CD54 (ICAM-1), CD55 (DAF), CD59, CD73 (NT5E), CD90 (Thy1), CD91 (LPR1), CD105 (SH2, Endoglin), CD137, CD146 (Muc 18), CD166 (ALCAM), and HLA-ABC.

In other embodiments, the compositions of the disclosure selectively bind to subcutaneous or white adipose tissue (WAT). By selectively binding to WAT, compositions of the invention can facilitate targeted delivery of compounds of the disclosure (the "AdipomiRs") which promote conversion of white adipocyte to thermogenic brite or brown or beige adipocytes (BAT). Exemplary WAT-positive markers include adiponectin, caveolin-1, caveolin-2, CD36 (FAT), CLH-22 (clathrin heavy chain chr. 22), FABP4 (adipocyte protein 2, ap2), SLC27A1 (FATP1), SLC27A2 (FATP2), GLUT4 (glucose transporter 4), perilipin 1, perilipin 2, and resistin.

In yet other embodiments, the compositions of the disclosure bind to an adipose target cell comprising cellular markers (including several lipid transporters) that are preferentially expressed at the surface of adipocytes. Exemplary adipocyte cellular markers include caveolin-1 (CAV1), caveolin-2 (CAV2), CD10 (MME), CD36 (FAT), CD90 (Thy-1), CD91 (low density lipoprotein receptor-related protein 1, LRP1), CD140A (platelet-derived growth factor receptor, alpha polypeptide, PDGFRA), CD140B (platelet-derived growth factor receptor, alpha polypeptide, PDGFRB), CD146 (cell surface glycoprotein MUC18, MCAM), CD166 (activated leukocyte cell adhesion molecule, ALCAM), CLH-22 (clathrin heavy chain chromosome 22), DCN (decorin), DPT (dermatopontin), FABP4 (fatty acid binding protein 4), GLUT4 (glucose transporter 4, SLC2A4), LAMP1 (lysosomal-associated membrane protein 1), LAMP2 (lysosomal-associated membrane protein 2), NPR1 (Natriuretic peptide receptor A), SLC27A1 (FATP1), and SLC27A2 (FATP2). See Table 1. Other specific (positive) markers of adipose tissue include adiponectin, BMP7, BMP8b, CIDEC, FGF 17, FGF 19, INSG1 (Insulin-induced gene 1), leptin, LPL, MetAP2, NR1H3 (LXRA), perilipin 1, perilipin 2, perilipin 3, PPARG, RBP4, and resistin.

TABLE 1

Human adipocyte surface markers

| Name | Entrez Gene ID | Ensembl Gene ID | Mean tissue mRNA expression level | Adipocyte mRNA expression level | Expression Ratio Adipocyte/ Mean |
|---|---|---|---|---|---|
| DPT (Dermatopontin) | 1805 | ENSG00000143196 | 20 | 747 | 37.4 |
| CD10 (MME) | 4311 | ENSG00000196549 | 20 | 707 | 35.4 |
| FABP4 | 2167 | ENSG00000170323 | 161 | 5407 | 33.6 |
| CD140B (PDGFRB) | 5159 | ENSG00000113721 | 22 | 274 | 12.5 |
| CD36 (FAT) | 948 | ENSG00000135218 | 71 | 885 | 12.5 |
| Caveolin 1 (CAV1) | 857 | ENSG00000105974 | 70 | 827 | 11.8 |
| Decorin (DCN) | 1634 | ENSG00000011465 | 566 | 6342 | 11.2 |
| CD140A (PDGFRA) | 5156 | ENSG00000134853 | 101 | 923 | 9.1 |
| CD91 (LRP1) | 4035 | ENSG00000123384 | 100 | 718 | 7.2 |
| Caveolin 2 (CAV2) | 858 | ENSG00000105971 | 46 | 259 | 5.6 |
| CD90 (THY1) | 7070 | ENSG00000154096 | 60 | 299 | 5.0 |
| CD146 (MCAM) | 4162 | ENSG00000076706 | 8 | 31 | 3.9 |
| CD166 (ALCAM) | 214 | ENSG00000170017 | 27 | 87 | 3.2 |
| LAMP1 | 3916 | ENSG00000185896 | 25 | 79 | 3.2 |
| NPR1 | 4881 | ENSG00000169418 | 133 | 189 | 1.4 |
| CLH-22 | 1213 | ENSG00000141367 | 1085 | 1040 | 1.0 |
| GLUT4 (SLC2A4) | 6517 | ENSG00000181856 | 7 | 7 | 1.0 |
| SLC27A1 (FATP1) | 376497 | ENSG00000130304 | 5 | 5 | 1.0 |
| SLC27A2 (FATP2) | 11001 | ENSG00000140284 | 18 | 11 | 0.6 |
| LAMP2 | 3920 | ENSG00000005893 | 37 | 16 | 0.4 |

In certain embodiments, compositions of the invention may comprise targeting elements which selectively bind one or more the above-identified markers, thus enhancing the selective delivery of compounds of the disclosure to adipocytes in order to enhance thermogenesis. Knowledge of the cell surface markers allows for their isolation by Flow Cytometry Cell Sorting (FACS) for subsequent screening and selection of targeting aptamers, for example by the SELEX or Cell-SELEX processes. The targeting element may be one described herein or a molecule such as an antibody, polypeptide, or nucleic acid that has been engineered to specifically bind to a cellular component of the target cell.

In some embodiments, aptamers are used to achieve this cell-specific delivery. An aptamer is an isolated or purified nucleic acid that binds with high specificity and affinity to a target through interactions other than Watson-Crick base pairing. An aptamer has a three dimensional structure that provides chemical contacts to specifically bind to a target. Unlike traditional nucleic acid binding, aptamer binding is not dependent upon a conserved linear base sequence, but rather a unique secondary or tertiary structure. That is, the nucleic acid sequence s of aptamers are non-coding sequences. Any coding potential that an aptamer may possess is entirely fortuitous and plays no role whatsoever in the binding of an aptamer to a target. A typical minimized aptamer is 5-15 kDa in size (15-45 nucleotides), binds to a target with nanomolar to sub-nanomolar affinity, and discriminates against closely related targets (e.g., aptamers will typically not bind to other proteins from the same gene or functional family).

In exemplary embodiments, compositions of the invention comprise an aptamer targeting element that selectively binds to at least one of the positive markers identified above. Preferably, the aptamer element does not bind to any of the negative markers identified above. Such aptamers may be identified by any means known in the art, e.g., the SELEX™ process. Systematic Evolution of Ligands by EXponential Enrichment, or SELEX™, is a method for the in vitro evolution of nucleic acid molecules with highly specific binding to target molecules, see U.S. Pat. Nos. 5,270,163 and 5,475,096, each of which is incorporated herein by reference in its entirety. More specifically, starting with a mixture containing a starting pool of nucleic acids, the SELEX™ method includes the steps of: (a) contacting the mixture with a target under conditions favorable for binding; (b) partitioning unbound nucleic acids from those nucleic acids that have bound to the target; (c) amplifying the bound nucleic acids to yield a ligand-enriched mixture of nucleic acids; and (d) reiterating the steps of contacting, partitioning, and amplifying through as many cycles as desired to yield highly specific, high affinity aptamers to the target. Additional rounds of selection progressively favor the best ligands until the resulting nucleic acid mixture is predominantly composed of only one or a few sequences. By performing iterative cycles of selection and amplification, the SELEX™ process may be used to obtain aptamers, also referred to in the art as "nucleic acid ligands", with any desired level of target binding affinity.

In those instances where transcribed aptamers, such as DNA or RNA aptamers, are being selected, the amplification step of the SELEX™ method includes the steps of: (i) reverse transcribing the nucleic acids dissociated from the nucleic acid-target complexes or otherwise transmitting the sequence information into a corresponding DNA sequence; (ii) PCR amplification; and (iii) transcribing the PCR amplified nucleic acids or otherwise transmitting the sequence information into a corresponding RNA sequence before restarting the process.

There are numerous modifications that may be made to an aptamer either before, during, and/or after the SELEX™ process, which are known in the art. Pre-SELEX™ process modifications or those made by incorporation into the SELEX™ process yield aptamers with both specificity for their target and improved stability. Post-SELEX™ process modifications made to already identified aptamers may result in further improved stability. Pre-SELEX™ process modifications usually lead to global changes in the aptamer, while post-SELEX™ process modifications lead to local changes in the aptamer.

The starting pool of nucleic acids can be random or partially random or non-random, modified or unmodified DNA, RNA, or DNA/RNA hybrids, and acceptable modifications include modifications at a base, sugar, and/or internucleotide linkage. The oligonucleotides of the starting pool preferably include a randomized sequence portion as well as fixed sequences necessary for efficient amplification. Typically, the oligonucleotides of the starting pool contain fixed 5' and 3' terminal sequences that flank an internal region of 30-50 random nucleotides. The randomized nucleotides can be produced in a number of ways, including chemical synthesis, size selection from randomly cleaved cellular nucleic acids, mutagenesis, solid phase oligonucleotide synthesis techniques, or solution phase methods (such as trimester synthesis methods). The random portion of the oligonucleotide can be of any length and can comprise ribonucleotides and/or deoxynucleotides, and can include modified or non-natural nucleotides or nucleotide analogs. The composition of the starting pool is dependent upon the desired properties of the final aptamer. Selections can be performed with nucleic acid sequences incorporating modified nucleotides to, e.g., stabilize the aptamers against degradation in vivo. For example, resistance to nuclease degradation can be greatly increased by the incorporation of modifying groups at the 2'-position. The starting library of oligonucleotides may be generated by automated chemical synthesis on a DNA synthesizer.

The SELEX process can be modified to incorporate a wide variety of modified nucleotides in order to generate a chemically-modified aptamer. For example, the aptamer may be synthesized entirely of modified nucleotides or with a subset of modified nucleotides. The modifications can be the same or different. Some or all nucleotides may be modified, and those that are modified may contain the same modification. For example, all nucleotides containing the same base may have one type of modification, while nucleotides containing other bases may have different types of modification. All purine nucleotides may have one type of modification (or are unmodified), while all pyrimidine nucleotides have another, different type of modification (or are unmodified). In this way, transcripts, or pools of transcripts, are generated using any combination of modifications, including for example, ribonucleotides (2'-OH), deoxyribonucleotides (2'-deoxy), 2'-amino nucleotides (2'-NH2), 2'-fluoro nucleotides (2'-F) and 2'-O-methyl (2'-OMe) nucleotides.

A SELEX process can employ a transcription mixture containing modified nucleotides in order to generate a modified aptamer. For example, a transcription mixture may contain only 2'-OMe A, G, C and U and/or T triphosphates (2'-OMe ATP, 2'-OMe UTP and/or 2'-OMe TTP, 2'-OMe CTP and 2'-OMe GTP), referred to as an MNA or mRmY mixture. Aptamers selected therefrom are referred to as MNA aptamers or mRmY aptamers and contain only 2'-O-methyl nucleotides. A transcription mixture containing all 2'-OH nucleotides is referred to as a "rN" mixture, and aptamers selected therefrom are referred to as "rN", "rRrY" or RNA aptamers. A transcription mixture containing all deoxy nucleotides is referred to as a "dN" mixture, and aptamers selected therefrom are referred to as "dN", "dRdY" or DNA aptamers. Aternatively, a subset of nucleotides (e.g., C, U and/or T) may comprise a first modified nucleotides (e.g, 2'-OMe) nucleotides and the remainder (e.g., A and G) comprise a second modified nucleotide (e.g., 2'-OH or 2'-F). For example, a transcription mixture containing 2'-F U and 2'-OMe A, G and C is referred to as a "fUmV" mixture, and aptamers selected therefrom are referred to as "fUmV" aptamers. A transcription mixture containing 2'-F A and G, and 2'-OMe C and U and/or T is referred to as a "fRmY" mixture, and aptamers selected therefrom are referred to as "fRmY" aptamers. A transcription mixture containing 2'-F A and 2'-OMe C, G and U and/or T is referred to as a "fAmB" mixture, and aptamers selected therefrom are referred to as "fAmB" aptamers.

In addition to the Pre-SELEX™ process modifications discussed above, one of skill in the art can improve already identified aptamers using post-SELEX™ process modifications. Examples of post-SELEX™ process modifications include, but are not limited to, truncation, deletion, substitution, or modification of a sugar or base or internucleotide linkage, capping, and PEGylation. In addition, the sequence requirements of an aptamer may be explored through doped reselections or aptamer medicinal chemistry. Doped reselections are carried out using a synthetic, degenerate pool that has been designed based on the aptamer of interest. The level of degeneracy usually varies from about 70-85% from the aptamer of interest. In general, sequences with neutral mutations are identified through the doped reselection process. Aptamer medicinal chemistry is an aptamer improvement technique in which sets of variant aptamers are chemically synthesized. These variants are then compared to each other and to the parent aptamer. Aptamer medicinal chemistry is used to explore the local, rather than global, introduction of substituents. For example, the following modifications may be introduced: modifications at a sugar, base, and/or internucleotide linkage, such as 2'-deoxy, 2'-ribo, or 2'-O-methyl purines or pyrimidines, phosphorothioate linkages may be introduced between nucleotides, a cap may be introduced at the 5' or 3' end of the aptamer (such as 3' inverted dT cap) to block degradation by exonucleases, or a polyethylene glycol (PEG) element may be added to the aptamer to increase the half-life of the aptamer in the subject.

Variations of the SELEX process may also be used to identify aptamers. For example, one may use agonist SELEX, toggle SELEX, cell SELEX, 2'-Modified SELEX, or Counter SELEX. Each of these variations of the SELEX process is known in the art. The most preferred SELEX method used in the compositions and methods of the invention is Cell-SELEX, a variation of the SELEX™ process that is described herein and also in WO/2014/022852, which is herein incorporated by reference. In general, SELEX uses a purified protein as its target. However, cell surface receptors are difficult to purify in their properly folded and modified conformations.

Cell-SELEX uses whole living cells as the target, whereby aptamers that recognize specific molecules in their native conformation in their natural environment on the surface of intact cells are selected by repeated amplification and binding to living cells. Thus, Cell-SELEX reflects a more physiological condition because the protein is displayed on the cell surface, including its post-translational modifications, rather than as an isolated and purified protein. In this cell-based selection, specific cell surface molecules/receptors, even unknown, can be directly targeted within their native environment, allowing a straightforward enrichment of cell-specific aptamers. Cell-SELEX generally consists of 2 procedures: positive selection with the target cells, and negative selection with non-targeted cells. Therefore, the specificity and affinity of aptamers essentially relies upon the differences between 2 types of cells or different states of a cell, which also makes it possible to simultaneously enrich for aptamers against several membrane receptors.

Cell surface proteins cycle intra-cellularly to some extent, and many surface receptors are actively internalized in response to ligand binding. For example, the glucose transporter GLUT4 is internalized by adipocytes through clathrin- and caveolin-mediated pathways. Therefore, aptamers that bind to cell surface receptors may be exploited for the delivery of a variety of cargos into cells. As a result, Cell-SELEX is used in the compositions and methods of the invention to identify aptamers that can drive the selective delivery of the compound of the disclosure to the targeted human cells (for example, ATMSCs and adipocytes).

Briefly, the selection of aptamers by Cell-SELEX starts with a library of single-stranded DNA and modified RNA nucleic acids that contain an approximately 40 to 60-mer random sequence region flanked by two approximately 20-mer PCR primer sequences. The library is incubated with the live and intact target ATMSCs and adipocyte cells to allow binding to take place. Then the cells are washed and the nucleic acid sequences bound to the cell surface are eluted. The collected sequences are then allowed to interact with excess negative control cells, and only the nucleic acid sequences that remain free in the supernatant are collected and amplified for the next round selection. The subtraction process efficiently eliminates the nucleic acid sequences that are bound to the control cells, while those target-cell-specific aptamer candidates are enriched. After multi-round selection (usually about 10 to 20 rounds achieve excellent enrichment of aptamer candidates), the highly enriched aptamer pools are cloned and sequenced by a high-throughput Next Generation Sequencing (NGS) method.

Further optimization for both large-scale synthesis and in vivo applications is achieved through a progressive set of modifications. Various modifications can be made to an aptamer to increase its stability and functionality, such as one or more modifications at the sugar, base, or internucleotide linkage. These modifications include, for example, 5'- and 3'-terminal and internal deletions to reduce the size of the aptamer, reselection for sequence modifications that increase the affinity or efficiency of target binding, introduction of stabilizing base-pair changes that increase the stability of helical elements in the aptamer, site-specific modifications of the 2'-ribose and phosphate positions to increase thermodynamic stability and to block nuclease degradation in vivo, and the addition of 5'- and/or 3'-caps to block degradation by exonucleases. For example, pyrimidine bases may be modified at the 5th position with iodide (I), bromide (Br), chloride (Cl), amino (NH3), azide (N3) to enhance the stability of the aptamer. Also by way of example, sugar residues may be modified at the 2' position with amino (NH2), fluoro (F), and methoxy (OCH3) groups. Other modifications include substitution of 4-thiouridine, substitution of 5-bromo or 5-iodouracil, backbone modifications, methylations, unusual base pairing combinations such as isobases, isocytidine, and isoguanodine, and 3' capping. Aptamers generated through these optimizations are typically 15 to 40 nucleotides long and exhibit serum half-lives greater than 10 hours.

In certain embodiments, the aptamer element may include Locked Nucleic Acid (LNA) bases or thiophosphate modifications. The incorporation of LNA bases (methylene link between the 2' oxygen and 4' carbon of the ribose ring) into a stem-loop structure has been shown to increase the melting temperature, nuclease stability and overall stability of the secondary structure of aptamers. Thiophosphate-modified aptamers (thioaptamers) bind to target proteins with high affinity (Kd in nM range) and specificity, and are characterized by a) enhanced nuclease resistance, b) easy synthesis and chemical modification, and c) lack of immunogenicity. Such modifications may be desirable in certain applications.

E. Methods of Treatment

In some embodiments, provided herein are methods for delivering a therapeutic compound to a specific cell, tissue, or organ in a subject and methods for treating obesity or metabolic disorders in a subject. The method generally comprises administering to the human subject an effective amount of a compound of the disclosure that modulates activity of at least one thermogenic regulator, (e.g., a mitochondrial uncoupler, such as UCP1 and/or UCP2).

Such methods of treatment may be specifically tailored or modified, based on knowledge obtained from the field of pharmacogenomics. Thus, another aspect of the invention provides methods for tailoring an individual's prophylactic or therapeutic treatment with either the target gene molecules of the present invention or target gene modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

Aptamirs, exomirs, lipomiRs, and adipomiRs can be tested in an appropriate animal model e.g., an obesity model including Diet Induced Obesity (DIO) mice, ob/ob mice (Lindstrom, 2007) and db/db mice (Sharma et al., 2003). For example, an aptamer, exomir, lipomiR or adipomiR as described herein can be used in an animal model to determine the efficacy, toxicity, or side effects of treatment with said agent. Alternatively, a therapeutic agent can be used in an animal model to determine the mechanism of action of such an agent. For example, a compound of the disclosure can be used in an animal model to determine the efficacy, toxicity, or side effects of treatment with such an agent. Alternatively, a compound can be used in an animal model to determine the mechanism of action of such an agent.

The disclosure also provides a method of inducing pre-adipocytes to differentiate into white adipocytes and white adipocytes into brown adipocytes, comprising administering to a population of pre-adipocytes one or more compounds disclosed herein.

The disclosure also provides a method for increasing insulin sensitivity in a subject in need thereof comprising administering the subject one or more compounds disclosed herein.

The disclosure also provides a method for treating diabetes or pre-diabetes in a subject in need thereof comprising administering the subject one or more compounds disclosed herein. In some embodiments, the diabetes is type 1 diabetes. In some embodiments, the diabetes is type 2 diabetes.

The disclosure also provides a method of causing fat loss in a subject in need thereof comprising administering the subject one or more compounds disclosed herein.

A compound of the disclosure (e.g. within an aptamir or exomir) modified for enhance uptake into cells (e.g., adipose cells) can be administered at a unit dose less than about 15 mg per kg of bodyweight, or less than 10, 5, 2, 1, 0.5, 0.1, 0.05, 0.01, 0.005, 0.001, 0.0005, 0.0001, 0.00005 or 0.00001 mg per kg of bodyweight, and less than 200 nmole of compound (e.g., about 4.4.times.1016 copies) per kg of bodyweight, or less than 1500, 750, 300, 150, 75, 15, 7.5, 1.5, 0.75, 0.15, 0.075, 0.015, 0.0075, 0.0015, 0.00075, 0.00015 nmole of compound per kg of bodyweight. The unit dose, for example, can be administered by injection (e.g., intravenous or intramuscular), an inhaled dose, or a topical application. Particularly preferred dosages are less than 2, 1, or 0.1 mg/kg of body weight.

Delivery of a compound of the disclosure (within an aptamir or exomir) directly to an organ or tissue (e.g., directly to adipose tissue) can be at a dosage on the order of about 0.00001 mg to about 3 mg per organ/tissue, or preferably about 0.0001-0.001 mg per organ/tissue, about 0.03-3.0 mg per organ/tissue, about 0.1-3.0 mg per organ/tissue or about 0.3-3.0 mg per organ/tissue. The dosage can be an amount effective to treat or prevent obesity. In one embodiment, the unit dose is administered less frequently than once a day, e.g., less than every 2, 4, 8 or 30 days. In another embodiment, the unit dose is not administered with a frequency (e.g., not a regular frequency). For example, the unit dose may be administered a single time. In one embodiment, the effective dose is administered with other traditional therapeutic modalities.

In certain embodiment, a subject is administered an initial dose, and one or more maintenance doses of a composition. The maintenance dose or doses are generally lower than the initial dose, e.g., one-half less of the initial dose. A maintenance regimen can include treating the subject with a dose or doses ranging from 0.01 mg/kg to 1.4 mg/kg of body weight per day, e.g., 10, 1, 0.1, 0.01, 0.001, or 0.00001 mg per kg of bodyweight per day. The maintenance doses are preferably administered no more than once every 5, 10, or 30 days. Further, the treatment regimen may last for a period of time which will vary depending upon the nature of the particular disease, its severity and the overall condition of the patient. In preferred embodiments the dosage may be delivered no more than once per day, e.g., no more than once per 24, 36, 48, or more hours, e.g., no more than once every 5 or 8 days. Following treatment, the patient can be monitored for changes in conditions, e.g., changes in percentage of body fat. The dosage of the compound may either be increased in the event the patient does not respond significantly to current dosage levels, or the dose may be decreased if a decrease in body fat is observed, or if undesired side effects are observed.

The effective dose can be administered in a single dose or in two or more doses, as desired or considered appropriate under the specific circumstances. If desired to facilitate repeated or frequent infusions, implantation of a delivery device, e.g., a pump, semi-permanent stent (e.g., sub-cutaneous, intravenous, intraperitoneal, intracisternal or intracapsular), or reservoir may be advisable. In one embodiment, a pharmaceutical composition includes a plurality of miRNA agent species. In another embodiment, the miRNA agent species has sequences that are non-overlapping and non-adjacent to another species with respect to a naturally occurring target sequence. In another embodiment, the plurality of miRNA agent species is specific for different naturally occurring target genes. In another embodiment, the miRNA agent is allele specific. In another embodiment, the plurality of miRNA agent species target two or more SNP alleles (e.g., two, three, four, five, six, or more SNP alleles).

Following successful treatment, it may be desirable to have the patient undergo maintenance therapy to prevent the recurrence of the disease state, wherein the compound of the invention is administered in maintenance doses, ranging from 0.01 mg per kg to 100 mg per kg of body weight (see U.S. Pat. No. 6,107,094).

The "effective amount" of the compound is an amount sufficient to be effective in treating or preventing a disorder or to regulate a physiological condition in humans. The concentration or amount of miRNA agent administered will depend on the parameters determined for the agent and the method of administration, e.g. nasal, buccal, or pulmonary. For example, nasal formulations tend to require much lower concentrations of some ingredients in order to avoid irritation or burning of the nasal passages. It is sometimes desirable to dilute an oral formulation up to 10-100 times in order to provide a suitable nasal formulation.

Certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a composition of the invention can include a single treatment or, preferably, can include a series of treatments. It will also be appreciated that the effective dosage of composition for treatment may increase or decrease over the course of a particular treatment. Changes in dosage may result and become apparent from the results of diagnostic assays as described herein. For example, the subject can be monitored after administering a compound of the disclosure. Based on information from the monitoring, an additional amount of the compound can be administered.

Dosing is dependent on severity and responsiveness of the disease condition to be treated, with the course of treatment lasting from several days to several months, or until a cure is effected or a diminution of disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual compounds, and can generally be estimated based on EC50s found to be effective in in vitro and in vivo animal models. In some embodiments, the animal models include transgenic animals that express a human gene, e.g., a gene that produces a target mRNA (e.g., a thermogenic regulator). The transgenic animal can be deficient for the corresponding endogenous mRNA. In another embodiment, the composition for testing includes a miRNA analog that is complementary to a compound of the disclosure, at least in an internal region, to a sequence that is conserved between a nucleic acid sequence in the animal model and the target nucleic acid sequence in a human.

Several studies have reported successful mammalian dosing using miRNA agents. For example, Esau, et al., 2006 reported dosing of normal mice with intraperitoneal doses of miR-122 antisense oligonucleotide ranging from 12.5 to 75 mg/kg twice weekly for 4 weeks. The mice appeared healthy and normal at the end of treatment, with no loss of body weight or reduced food intake. Plasma transaminase levels were in the normal range (AST ¾ 45, ALT ¾ 35) for all doses with the exception of the 75 mg/kg dose of miR-122 ASO, which showed a very mild increase in ALT and AST levels. They concluded that 50 mg/kg was an effective, nontoxic dose. Another study by Krutzfeldt, et al., 2005, injected antagomirs to silence miR-122 in mice using a total dose of 80, 160 or 240 mg per kg body weight. The highest dose resulted in a complete loss of miR-122 signal. In yet another study, locked nucleic acids ("LNAs") were successfully applied in primates to silence miR-122. Elmen, et al., 2008, report that efficient silencing of miR-122 was achieved in primates by three doses of 10 mg per kg LNA-antimiR, leading to a long-lasting and reversible decrease in total plasma cholesterol without any evidence for LNA-associated toxicities or histopathological changes in the study animals.

The compositions of the invention may be directly introduced into a cell (e.g., an adipocyte); or introduced extracellularly into a cavity, interstitial space, into the circulation of an organism, introduced orally, or may be introduced by bathing a cell or organism in a solution containing the nucleic acid. Vascular or extravascular circulation, the blood or lymph system, and the cerebrospinal fluid are sites where the nucleic acid may be introduced.

In certain embodiments, the methods described herein include co-administration of miRNA agents with other drugs or pharmaceuticals, e.g., compositions for modulating thermogenesis, compositions for treating diabetes, compositions for treating obesity. Compositions for modulating thermogenesis include beta-3 adrenergic receptor agonists, thyroid hormones, PPARG agonists, leptin, adiponectin, and orexin.

F. Pharmaceutical Preparations

In one aspect, the methods disclosed herein can include the administration of pharmaceutical compositions and formulations comprising miRNA agents capable of modulating the activity of at least one thermogenic modulator.

In certain embodiments, the compositions are formulated with a pharmaceutically acceptable carrier. The pharmaceutical compositions and formulations can be administered parenterally, topically, by direct administration into the gastrointestinal tract (e.g., orally or rectally), or by local administration, such as by aerosol or transdermally. The pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration of pharmaceuticals are well described in the scientific and patent literature, see, e.g., Remington: The Science and Practice of Pharmacy, 21st ed., 2005.

The miRNA agents can be administered alone or as a component of a pharmaceutical formulation (composition). The compounds may be formulated for administration, in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of the compositions include those suitable for intradermal, inhalation, oral/nasal, topical, parenteral, rectal, and/or intravaginal administration. The formulations may conveniently be presented in unit dosage form and may be prepared by any methods well known in the art of pharmacy. The amount of active ingredient (e.g., oligonucleotides) which can be combined with a carrier material to produce a single dosage form will vary depending upon the host being treated, the particular mode of administration, e.g., intradermal or inhalation. The amount of active ingredient which can be combined with a carrier material to produce a single dosage form will generally be that amount of the compound which produces a therapeutic effect, e.g., an antigen specific T cell or humoral response.

Pharmaceutical formulations can be prepared according to any method known to the art for the manufacture of pharmaceuticals. Such drugs can contain sweetening agents, flavoring agents, coloring agents and preserving agents. A formulation can be admixtured with nontoxic pharmaceutically acceptable excipients which are suitable for manufacture. Formulations may comprise one or more diluents, emulsifiers, preservatives, buffers, excipients, etc. and may be provided in such forms as liquids, powders, emulsions, lyophilized powders, sprays, creams, lotions, controlled release formulations, tablets, pills, gels, on patches, in implants, etc.

Pharmaceutical formulations for oral administration can be formulated using pharmaceutically acceptable carriers well known in the art in appropriate and suitable dosages. Such carriers enable the pharmaceuticals to be formulated in unit dosage forms as tablets, pills, powder, dragées, capsules, liquids, lozenges, gels, syrups, slurries, suspensions, etc., suitable for ingestion by the patient. Pharmaceutical preparations for oral use can be formulated as a solid excipient, optionally grinding a resulting mixture, and processing the mixture of granules, after adding suitable additional compounds, if desired, to obtain tablets or dragée cores. Suitable solid excipients are carbohydrate or protein fillers include, e.g., sugars, including lactose, sucrose, mannitol, or sorbitol; starch from corn, wheat, rice, potato, or other plants; cellulose such as methyl cellulose, hydroxypropylmethyl-cellulose, or sodium carboxy-methylcellulose; and gums including arabic and tragacanth; and proteins, e.g., gelatin and collagen. Disintegrating or solubilizing agents may be added, such as the cross-linked polyvinyl pyrrolidone, agar, alginic acid, or a salt thereof, such as sodium alginate. Push-fit capsules can contain active agents mixed with a filler or binders such as lactose or starches, lubricants such as talc or magnesium stearate, and, optionally, stabilizers. In soft capsules, the active agents can be dissolved or suspended in suitable liquids, such as fatty oils, liquid paraffin, or liquid polyethylene glycol with or without stabilizers.

Aqueous suspensions can contain an active agent (e.g., oligonucleotides) in admixture with excipients suitable for the manufacture of aqueous suspensions, e.g., for aqueous intradermal injections. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

In certain embodiments, oil-based pharmaceuticals are used for administration of the miRNA agents. Oil-based suspensions can be formulated by suspending an active agent in a vegetable oil, such as arachis oil, olive oil, sesame oil or coconut oil, or in a mineral oil such as liquid paraffin; or a mixture of these. See e.g., U.S. Pat. No. 5,716,928 describing using essential oils or essential oil components for increasing bioavailability and reducing inter- and intra-individual variability of orally administered hydrophobic pharmaceutical compounds (see also U.S. Pat. No. 5,858, 401). The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle (Minto, C. F. et al.; 1997).

In certain embodiments, the pharmaceutical compositions and formulations are in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent. In alternative embodiments, these injectable oil-in-water emulsions comprise a paraffin oil, a sorbitan monooleate, an ethoxylated sorbitan monooleate and/or an ethoxylated sorbitan trioleate.

In certain embodiments, the pharmaceutical compositions and formulations are administered by in intranasal, intraocular and intravaginal routes including suppositories, insufflation, powders and aerosol formulations (for examples of steroid inhalants, see e.g., Rohatagi (1995) J. Clin. Pharmacol. 35: 1187-1193; Tjwa (1995) Ann. Allergy Asthma Immunol. 75: 107-111). Suppositories formulations can be prepared by mixing the drug with a suitable non-irritating excipient which is solid at ordinary temperatures but liquid at body temperatures and will therefore melt in the body to release the drug. Such materials are cocoa butter and polyethylene glycols.

In certain embodiments, the pharmaceutical compositions and formulations are delivered transdermally, by a topical route, formulated as applicator sticks, solutions, suspensions, emulsions, gels, creams, ointments, pastes, jellies, paints, powders, and aerosols.

In certain embodiments, the pharmaceutical compositions and formulations are delivered as microspheres for slow release in the body. For example, microspheres can be administered via intradermal injection of drug which slowly release subcutaneously; see Rao (1995) J. Biomater Sci. Polym. Ed. 7:623-645; as biodegradable and injectable gel formulations, see, e.g., Gao (1995) Pharm. Res. 12:857-863 (1995); or, as microspheres for oral administration, see, e.g., Eyles (1997) J. Pharm. Pharmacol. 49:669-674.

In certain embodiments, the pharmaceutical compositions and formulations are parenterally administered, such as by intravenous (IV) administration or administration into a body cavity or lumen of an organ. These formulations can comprise a solution of active agent dissolved in a pharmaceutically acceptable carrier. Acceptable vehicles and solvents that can be employed are water and Ringer's solution, an isotonic sodium chloride. In addition, sterile fixed oils can be employed as a solvent or suspending medium. For this purpose, any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of active agent in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated using those suitable dispersing or wetting agents and suspending agents. The sterile injectable preparation can also be a suspension in a nontoxic parenterally-acceptable diluent or solvent, such as a solution of 1,3-butanediol. The administration can be by bolus or continuous infusion (e.g., substantially uninterrupted introduction into a blood vessel for a specified period of time).

In certain embodiments, the pharmaceutical compounds and formulations are lyophilized. Stable lyophilized formulations comprising an inhibitory nucleic acid can be made by lyophilizing a solution comprising a pharmaceutical and a bulking agent, e.g., mannitol, trehalose, raffinose, and sucrose or mixtures thereof. A process for preparing a stable lyophilized formulation can include lyophilizing a solution about 2.5 mg/mL nucleic acid, about 15 mg/mL sucrose, about 19 mg/mL NaCl, and a sodium citrate buffer having a pH greater than 5.5 but less than 6.5. See, e.g., U.S. 20040028670.

In certain embodiments, the pharmaceutical compositions and formulations are delivered by the use of liposomes. By using liposomes, particularly where the liposome surface carries ligands specific for target cells, or are otherwise preferentially directed to a specific organ, one can focus the delivery of the active agent into target cells in vivo. See, e.g., U.S. Pat. Nos. 6,063,400; 6,007,839; Al-Muhammed (1996) J. Microencapsul. 13: 293-306; Chonn (1995) Curr. Opin. Biotechnol. 6:698-708; Ostro (1989) Am. J. Hosp. Pharm. 46: 1576-1587.

The formulations can be administered for prophylactic and/or therapeutic treatments. In certain embodiments, for therapeutic applications, compositions are administered to a subject who is need of reduced fat mass, glucose and lipid levels, or who is at risk of or has a disorder described herein, in an amount sufficient to cure, alleviate or partially arrest the clinical manifestations of the disorder or its complications; this can be called a therapeutically effective amount. For example, in certain embodiments, pharmaceutical compositions are administered in an amount sufficient to treat obesity in a subject.

The amount of pharmaceutical composition adequate to accomplish this is a therapeutically effective dose. The dosage schedule and amounts effective for this use, i.e., the dosing regimen, will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, e.g., Hidalgo-Aragones (1996) J. Steroid Biochem. Mol. Biol. 58:611-617; Groning (1996) Pharmazie 51: 337-341; Fotherby (1996) Contraception 54:59-69; Johnson (1995) J. Pharm. Sci. 84: 1144-1146; Rohatagi (1995) Pharmazie 50:610-613; Brophy (1983) Eur. J. Clin. Pharmacol. 24: 103-108; Remington: The Science and Practice of Pharmacy, 21st ed., 2005). The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods are correct and appropriate. Single or multiple administrations of formulations can be given depending on for example: the dosage and frequency as required and tolerated by the patient, the degree and amount of cholesterol homeostasis generated after each administration, and the like. The formulations should provide a sufficient quantity of active agent to effectively treat, prevent or ameliorate conditions, diseases or symptoms, e.g., treat obesity. In certain embodiments, pharmaceutical formulations for oral administration are in a daily amount of between about 1 to 100 or more mg per kilogram of body weight per day. Lower dosages can be used, in contrast to administration orally, into the blood stream, into a body cavity or into a lumen of an organ. Substantially higher dosages can be used in topical or oral administration or administering by powders, spray or inhalation. Actual methods for preparing parenterally or non-parenterally administrable formulations will be known or apparent to those skilled in the art and are described in more detail in such publications as Remington: The Science and Practice of Pharmacy, 21st ed., 2005.

G. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

1.1.1 Example 1

1.1.2 In Silico Identification of miRNAs Binding to KDM3A and Related Genes

Figure 1:
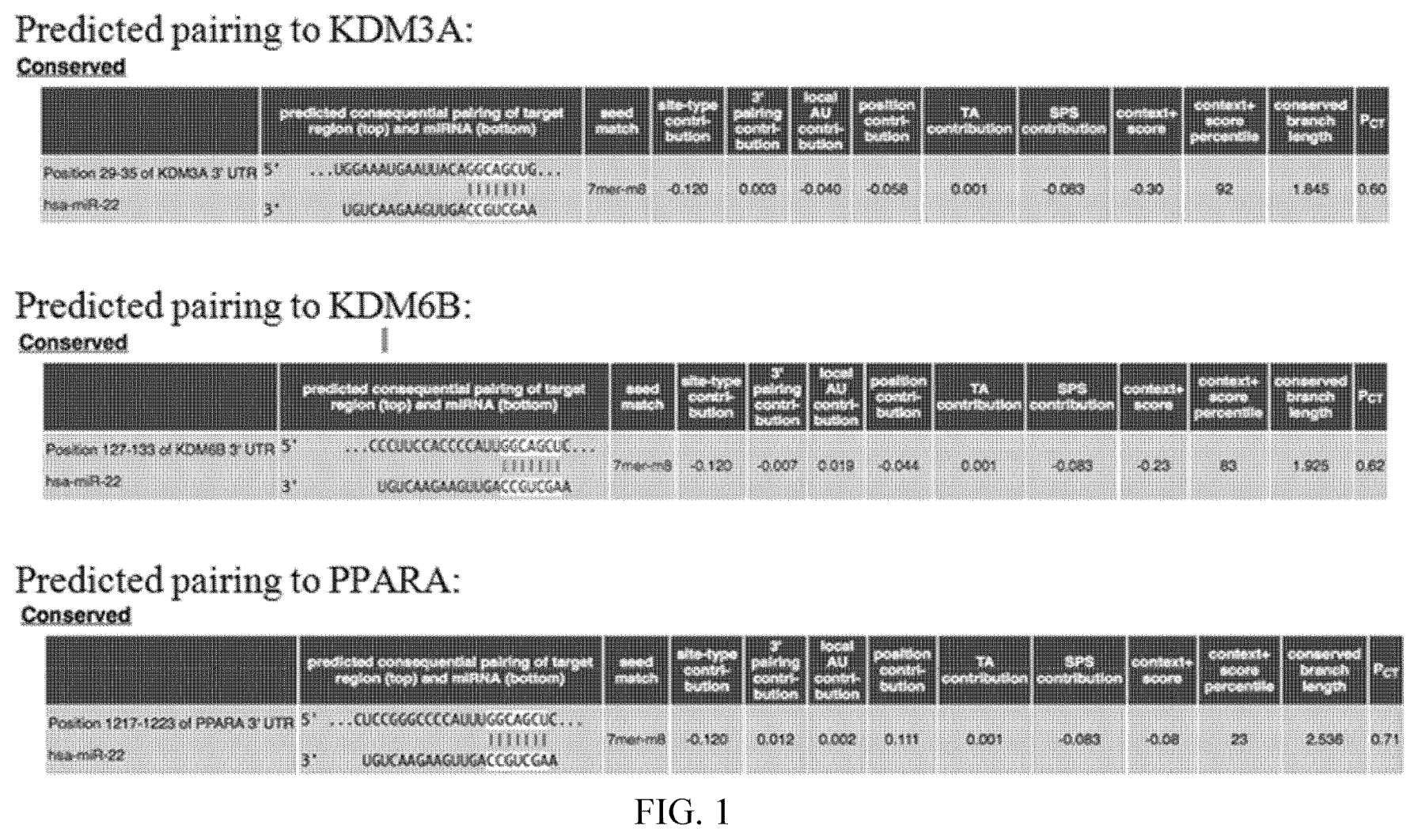

The TargetScan Human prediction database (release 6.2) was searched to identify miRNAs that potentially bind to the human KDM3A gene sequence. The human KDM3A 3' UTR 29-35 region was identified to be a conserved target for hsa-miR-22/22-3p, a miRNA that is highly expressed in human subcutaneous adipocytes (FIG. 1). Several other miRNA Targets Databases confirmed this complementarity between hsa-miR-22/22-3p and KDM3A sequences. Similarly, the human lysine (K)-specific demethylase 6B (KDM6B) 3'UTR 127-133 region is a conserved target for hsa-miR-22/22-3p. Therefore, increased production of the demethylases KDM3A and KDM6B induced by an hsa-miR-22 antagomir leads to demethylation of the UCP1 gene promoter region, thus facilitating binding of several regulatory elements to increase UCP1 production. Furthermore, the human PPARA 3'UTR 1217-1223 region is also a conserved target for hsa-miR-22/3p, suggesting that miR-22 also modulates the PPAR pathway. PPARA is a well-known factor activating lipid catabolism and thermogenesis (Hondares, E., et al., 2011; Xue, B., et al., 2005; Langin, D. et al., 2012).

1.1.3 Example 2

1.1.4 In Silico Search of Gene Targets of miR-22-3p

Surveying the published literature, digital curation of a list of 721 genes of interest involved in lipid metabolism, oxidative phosphorylation, mitochondrial functions, respiratory cycle, browning of adipocytes and thermogenesis was performed (AptamiR 721 genes, Table 2). 34 miRNA Targets and Expression in silico tools and a proprietary in silico meta-tool (R-AptamiR) were utilized to identify 542 putative mRNA targets of miR-22-3p. These 542 putative mRNA targets were matched against the AptamiR curated list of 721 target genes and 60 target genes of miR-22-3p were identified as belonging to the curated list (FIG. 2).

TABLE 2

Curated list of 721 genes involved in lipid metabolism, oxidative phosphorylation, mitochondrial functions, respiratory cycle, browning of adipocytes and thermogenesis.

| Gene | Ensembl | Gene | Ensembl | Gene | Ensembl |
|---|---|---|---|---|---|
| ADIG | ENSG00000182035 | FGF1 | ENSG00000113578 | PDGFRA | ENSG00000134853 |
| ADIPOQ | ENSG00000181092 | FGF10 | ENSG00000070193 | PDGFRB | ENSG00000113721 |
| ADRB2 | ENSG00000169252 | FGF13 | ENSG00000129682 | PDK4 | ENSG00000004799 |
| ADRB3 | ENSG00000188778 | FGF16 | ENSG00000196468 | PEBP1 | ENSG00000089220 |
| ADRBK1 | ENSG00000173020 | FGF17 | ENSG00000158815 | PEX6 | ENSG00000124587 |
| AEBP1 | ENSG00000106624 | FGF19 | ENSG00000162344 | PGRMC1 | ENSG00000101856 |
| AGPAT2 | ENSG00000169692 | FGF2 | ENSG00000138685 | PGRMC2 | ENSG00000164040 |
| AGPAT3 | ENSG00000160216 | FGF21 | ENSG00000105550 | PHACTR2 | ENSG00000112419 |
| AGPAT7 | ENSG00000138678 | FHL1 | ENSG00000022267 | PHB | ENSG00000167085 |
| AGT | ENSG00000135744 | FIS1 | ENSG00000214253 | PHB2 | ENSG00000215021 |
| AIFM2 | ENSG00000042286 | FNDC5 | ENSG00000160097 | PICALM | ENSG00000073921 |
| AKR1C3 | ENSG00000196139 | FOXC2 | ENSG00000176692 | PIGK | ENSG00000142892 |
| ALCAM | ENSG00000170017 | FOXO1 | ENSG00000150907 | PKIG | ENSG00000168734 |
| ALDH1A1 | ENSG00000165092 | G0S2 | ENSG00000123689 | PLA2G4C | ENSG00000105499 |
| ALDH5A1 | ENSG00000112294 | GAPDH | ENSG00000111640 | PLAC8 | ENSG00000145287 |
| ALDH6A1 | ENSG00000119711 | GATA2 | ENSG00000179348 | PLEKHA1 | ENSG00000107679 |
| ANGPT2 | ENSG00000091879 | GATA3 | ENSG00000107485 | PLEKHA2 | ENSG00000169499 |
| ANGPTL1 | ENSG00000116194 | GDF3 | ENSG00000184344 | PLEKHA3 | ENSG00000116095 |
| ANGPTL2 | ENSG00000136859 | GFM2 | ENSG0000016434 | PLIN1 | ENSG000001668197 |
| ANGPTL3 | ENSG00000132855 | GHSR | ENSG0000012185 | PLIN2 | ENSG000001478723 |
| ANGPTL4 | ENSG00000167772 | GK | ENSG00000019881 | PLIN3 | ENSG000001053554 |
| ANPEP | ENSG00000166825 | GLA | ENSG00000102393 | PLIN4 | ENSG00000167676 |
| ANXA1 | ENSG00000135046 | GLB1 | ENSG00000170266 | PLIN5 | ENSG00000214456 |
| ANXA10 | ENSG00000109511 | GLTP | ENSG00000139433 | PNPLA2 | ENSG00000177666 |
| ANXA11 | ENSG00000122359 | GMNN | ENSG00000112312 | PNPLA3 | ENSG00000100344 |
| ANXA2 | ENSG00000182718 | GOT1 | ENSG0000012005 | PPA1 | ENSG000001808173 |
| ANXA3 | ENSG00000138772 | GOT2 | ENSG0000012516 | PPA2 | ENSG000001387776 |
| ANXA4 | ENSG00000196975 | GPAA1 | ENSG00000197858 | PPARA | ENSG00000186951 |
| ANXA5 | ENSG00000164111 | GPAM | ENSG00000119927 | PPARD | ENSG00000112033 |
| ANXA6 | ENSG00000197043 | GPBAR1 | ENSG00000179921 | PPARG | ENSG00000132170 |
| ANXA7 | ENSG00000138279 | GPD1 | ENSG00000167588 | PPARGC1A | ENSG00000109819 |
| ANXA9 | ENSG00000143412 | GRK5 | ENSG00000198873 | PPARGC1B | ENSG00000155846 |
| APLN | ENSG00000171388 | GYPC | ENSG00000136732 | PPRC1 | ENSG00000148840 |
| APOC1 | ENSG00000130208 | HACL1 | ENSG00000131373 | PPT1 | ENSG00000131238 |
| APOD | ENSG00000189058 | HADHA | ENSG00000084754 | PRDM16 | ENSG00000142611 |
| APOE | ENSG00000130203 | HADHB | ENSG00000138029 | PRDX3 | ENSG00000165672 |
| APOL1 | ENSG00000100342 | HCCS | ENSG00000004961 | PRDX6 | ENSG00000117592 |
| APOL2 | ENSG00000128335 | HCRT | ENSG00000161610 | PREX1 | ENSG00000124126 |
| APOL3 | ENSG00000128284 | HDLBP | ENSG00000115677 | PRKAA1 | ENSG00000132356 |
| APOL4 | ENSG00000100336 | HES1 | ENSG00000114315 | PRKAA2 | ENSG00000162409 |
| APOL6 | ENSG00000221963 | HIF1A | ENSG00000100644 | PRKACA | ENSG00000072062 |
| AQP7 | ENSG00000165269 | HOXA9 | ENSG00000078399 | PRKACB | ENSG00000142875 |
| ARRDC3 | ENSG00000113369 | HOXC8 | ENSG00000037965 | PRKAR1A | ENSG00000108946 |
| ATF4 | ENSG00000128272 | HOXC9 | ENSG00000180806 | PRKAR2B | ENSG00000005249 |
| ATG7 | ENSG00000197548 | HPRT1 | ENSG00000165704 | PRKCB | ENSG00000166501 |
| ATP11B | ENSG00000058063 | HSD17B4 | ENSG00000133835 | PRKG1 | ENSG00000185532 |
| ATP12A | ENSG00000075673 | HSD17B6 | ENSG00000025423 | PRLR | ENSG00000113494 |
| ATP4A | ENSG00000105675 | HSPB7 | ENSG00000173641 | PSAP | ENSG00000197746 |
| ATP4B | ENSG00000186009 | HSPH1 | ENSG00000120694 | PTEN | ENSG00000171862 |
| ATP5A1 | ENSG00000152234 | ID1 | ENSG00000125968 | PTGIS | ENSG00000124212 |
| ATP5B | ENSG00000110955 | ID3 | ENSG00000117318 | PXDC1 | ENSG00000168994 |
| ATP5C1 | ENSG00000165629 | IDH3A | ENSG00000166411 | RAB35 | ENSG00000111737 |
| ATP5D | ENSG00000099624 | IKBKE | ENSG00000143466 | RARB | ENSG00000077092 |
| ATP5E | ENSG00000124172 | INHBB | ENSG00000163083 | RASAL1 | ENSG00000111344 |
| ATP5F1 | ENSG00000116459 | INSIG1 | ENSG00000186480 | RASGRP1 | ENSG00000172575 |
| ATP5G1 | ENSG00000159199 | INSR | ENSG00000171105 | RASGRP4 | ENSG00000171777 |
| ATP5G2 | ENSG00000135390 | IRS1 | ENSG00000169047 | RB1 | ENSG00000139687 |
| ATP5G3 | ENSG00000154518 | IRS2 | ENSG00000185950 | RBL1 | ENSG00000080839 |
| ATP5H | ENSG00000167863 | ISM1 | ENSG00000101230 | RBP4 | ENSG00000138207 |
| ATP5I | ENSG00000169020 | ITGA4 | ENSG00000115232 | RDH13 | ENSG00000160439 |
| ATP5J | ENSG00000154723 | ITGA7 | ENSG00000135424 | REEP1 | ENSG00000068615 |
| ATP5J2 | ENSG00000241468 | ITGB1 | ENSG00000150093 | REEP6 | ENSG00000115255 |
| ATP5L | ENSG00000167283 | JUN | ENSG00000177606 | RETN | ENSG00000104918 |
| ATP5L2 | ENSG00000249222 | KCNK3 | ENSG00000171303 | RGS7BP | ENSG00000186479 |
| ATP5O | ENSG00000241837 | KDM3A | ENSG00000115548 | RPLP0 | ENSG00000089157 |
| ATP6 | ENSG00000198899 | KDM4C | ENSG00000107077 | RPS6KB1 | ENSG00000108443 |
| ATP6V0A2 | ENSG00000185344 | KDM6B | ENSG00000132510 | RUNX1T1 | ENSG00000079102 |
| ATP6V0B | ENSG00000117410 | KIAA1456 | ENSG00000250305 | RUNX2 | ENSG00000124813 |
| ATP6V0D2 | ENSG00000147614 | KLF11 | ENSG00000172059 | RXRA | ENSG00000186350 |
| ATP6V1B1 | ENSG00000116039 | KLF15 | ENSG00000163884 | RXRG | ENSG00000143171 |

TABLE 2-continued

Curated list of 721 genes involved in lipid metabolism, oxidative phosphorylation, mitochondrial functions, respiratory cycle, browning of adipocytes and thermogenesis.

| Gene | Ensembl | Gene | Ensembl | Gene | Ensembl |
| --- | --- | --- | --- | --- | --- |
| ATP6V1B2 | ENSG00000147416 | KLF2 | ENSG00000127528 | SCARB2 | ENSG00000138760 |
| ATP6V1C2 | ENSG00000143882 | KLF3 | ENSG00000109787 | SCARF1 | ENSG00000074660 |
| ATP6V1D | ENSG00000100554 | KLF4 | ENSG00000136826 | SCD | ENSG00000099194 |
| ATP6V1E1 | ENSG00000131100 | KLF5 | ENSG00000102554 | SCIN | ENSG00000006747 |
| ATP6V1E1P1 | ENSG00000225099 | KLF6 | ENSG00000067082 | SCMH1 | ENSG00000010803 |
| ATP6V1E2 | ENSG00000250565 | KLF7 | ENSG00000118263 | SCO1 | ENSG00000133028 |
| ATP6V1G3 | ENSG00000151418 | KLHL13 | ENSG00000003096 | SCO2 | ENSG00000130489 |
| ATP6V1H | ENSG00000047249 | KTN1 | ENSG00000126777 | SCP2 | ENSG00000116171 |
| ATP8 | EN5G00000228253 | LAMC1 | ENSG00000135862 | SDHA | ENSG00000073578 |
| ATPAF1 | ENSG00000123472 | LAMP1 | ENSG00000185896 | SDHAF1 | ENSG00000205138 |
| ATPAF2 | ENSG00000171953 | LAMP2 | ENSG00000005893 | SDHAF2 | ENSG00000167985 |
| ATPIF1 | ENSG00000130770 | LCAT | ENSG00000213398 | SDHB | ENSG00000117118 |
| AXIN1 | ENSG00000103126 | LCN2 | ENSG00000148346 | SDHC | ENSG00000143252 |
| AZGP1 | ENSG00000160862 | LDLR | ENSG00000130164 | SDHD | ENSG00000204370 |
| B2M | ENSG00000166710 | LEP | ENSG00000174697 | SDPR | ENSG00000168497 |
| BACE1 | ENSG00000186318 | LGALS12 | ENSG00000133317 | SFRP1 | ENSG00000104332 |
| BAX | ENSG00000087088 | LHPP | ENSG00000107902 | SFRP5 | ENSG00000120057 |
| BCS1L | ENSG00000074582 | LHX8 | ENSG00000162624 | SGK2 | ENSG00000101049 |
| BDH2 | ENSG00000164039 | LIFR | ENSG00000113594 | SHBG | ENSG00000129214 |
| BHLHB9 | ENSG00000198908 | LIPE | ENSG00000079435 | SHC1 | ENSG00000160691 |
| BMP2 | ENSG00000125845 | LMNA | ENSG00000160789 | SHH | ENSG00000164690 |
| BMP4 | ENSG00000125378 | LPIN1 | ENSG00000134324 | SHOX2 | ENSG00000168779 |
| BMP7 | ENSG00000101144 | LPL | ENSG00000175445 | SIRT1 | ENSG00000096717 |
| BMP8B | ENSG00000116985 | LRP1 | ENSG00000123384 | SIRT2 | ENSG00000068903 |
| BRCC3 | ENSG00000185515 | LRP5 | ENSG00000162337 | SIRT3 | ENSG00000142082 |
| C4A | ENSG00000244731 | LRP6 | ENSG00000070018 | SIRT4 | ENSG00000089163 |
| C4B | ENSG00000224389 | LRRC17 | ENSG00000128606 | SIRT5 | ENSG00000124523 |
| C7orf25 | ENSG00000136197 | LRRC39 | ENSG00000122477 | SIRT6 | ENSG00000077463 |
| CA12 | ENSG00000074410 | MAPK14 | ENSG00000112062 | SIRT7 | ENSG00000187531 |
| CA2 | ENSG00000104267 | 1-Mar | ENSG00000186205 | SLC16A1 | ENSG00000155380 |
| CAV1 | ENSG00000105974 | MCAM | ENSG00000076706 | SLC22A23 | ENSG00000137266 |
| CAV2 | ENSG00000105971 | MCTP1 | ENSG00000175471 | SLC25A1 | ENSG00000100075 |
| CAV3 | ENSG00000182533 | MCTP2 | ENSG00000140563 | SLC25A11 | ENSG00000108528 |
| CBR1 | ENSG00000159228 | ME1 | ENSG00000065833 | SLC25A12 | ENSG00000115840 |
| CBR3 | ENSG00000159231 | MED13 | ENSG00000108510 | SLC25A18 | ENSG00000182902 |
| CBR4 | ENSG00000145439 | MEOX2 | ENSG00000066511 | SLC25A20 | ENSG00000178537 |
| CCND1 | ENSG00000110092 | METAP2 | ENSG00000111142 | SLC27A1 | ENSG00000130304 |
| CD151 | ENSG00000177697 | METRNL | ENSG00000176845 | SLC27A2 | ENSG00000140284 |
| CD1D | ENSG00000158473 | METTL7A | ENSG00000185432 | SLC27A3 | ENSG00000143554 |
| CD248 | ENSG00000174807 | MFF | ENSG00000168958 | SLC27A4 | ENSG00000167114 |
| CD34 | ENSG00000174059 | MFGE8 | ENSG00000140545 | SLC2A4 | ENSG00000181856 |
| CD36 | ENSG00000135218 | MFN1 | ENSG00000171109 | SLC36A2 | ENSG00000186335 |
| CD40 | ENSG00000101017 | MFN2 | ENSG00000116688 | SLCO2A1 | ENSG00000174640 |
| CD44 | ENSG00000026508 | MGLL | ENSG00000074416 | SLMO2 | ENSG00000101166 |
| CD63 | ENSG00000135404 | MINOS1 | ENSG00000173436 | SMAD3 | ENSG00000166949 |
| CD81 | ENSG00000110651 | MME | ENSG00000196549 | SMAD7 | ENSG00000101665 |
| CDK4 | ENSG00000135446 | MMP1 | ENSG00000196611 | SMAD9 | ENSG00000120693 |
| CDKN1A | ENSG00000124762 | MMP10 | ENSG00000166670 | SMPD3 | ENSG00000103056 |
| CDKN1B | ENSG00000111276 | MMP12 | ENSG00000110347 | SMPD4 | ENSG00000136699 |
| CEBPA | ENSG00000245848 | MMP13 | ENSG00000137745 | SOD1 | ENSG00000142168 |
| CEBPB | ENSG00000172216 | MMP15 | ENSG00000102996 | SOD2 | ENSG00000112096 |
| CEBPD | ENSG00000221869 | MMP16 | ENSG00000156103 | SOD3 | ENSG00000109610 |
| CEL | ENSG00000170835 | MMP28 | ENSG00000129270 | SORBS1 | ENSG00000095637 |
| CES1 | ENSG00000198848 | MMP3 | ENSG00000149968 | SPARC | ENSG00000113140 |
| CFD | ENSG00000197766 | MMP8 | ENSG00000118113 | SPAST | ENSG00000021574 |
| CHCHD7 | ENSG00000170791 | MMP9 | ENSG00000100985 | SPTLC3 | ENSG00000172296 |
| CHKA | ENSG00000110721 | MOCS2 | ENSG00000164172 | SRC | ENSG00000197122 |
| CIDEA | ENSG00000176194 | MOGAT1 | ENSG00000124003 | SREBF1 | ENSG00000072310 |
| CIDEC | ENSG00000187288 | MOGAT2 | ENSG00000166391 | SREBF2 | ENSG00000198911 |
| CITED1 | ENSG00000125931 | MPC1 | ENSG00000060762 | STAR | ENSG00000147465 |
| CITED2 | ENSG00000164442 | MPC2 | ENSG00000131748 | STARD3 | ENSG00000131748 |
| CITED4 | ENSG00000179862 | MPZL2 | ENSG00000149573 | STAT5A | ENSG00000126561 |
| CKMT1A | ENSG00000223572 | MRAP | ENSG00000170262 | STOM | ENSG00000148175 |
| CKMT1B | ENSG00000237289 | MRPL42 | ENSG00000198015 | STS | ENSG00000101846 |
| CKMT2 | ENSG00000131730 | MSANTD3 | ENSG00000066962 | STX10 | ENSG00000104915 |
| CLTCL1 | ENSG00000070371 | MSTN | ENSG00000138379 | STX12 | ENSG00000117758 |
| CMPK1 | ENSG00000162368 | MT-ATP6 | ENSG00000198899 | SUCLA2 | ENSG00000136143 |
| CNR1 | ENSG00000118432 | MTOR | ENSG00000198793 | SURF1 | ENSG00000148290 |
| CNTNAP3 | ENSG00000106714 | MYBPC2 | ENSG00000086967 | SYP | ENSG00000102003 |
| COA1 | ENSG00000106603 | MYF5 | ENSG00000111049 | SYT1 | ENSG00000067715 |
| COA3 | ENSG00000183978 | MYH11 | ENSG00000133392 | SYTL4 | ENSG00000102362 |
| COA4 | ENSG00000181924 | MYLPF | ENSG00000180209 | TAZ | ENSG00000102125 |
| COA5 | ENSG00000183513 | MYOG | ENSG00000122180 | TBX1 | ENSG00000184058 |
| COA6 | ENSG00000168275 | NAA20 | ENSG00000173418 | TCF21 | ENSG00000118526 |

TABLE 2-continued

Curated list of 721 genes involved in lipid metabolism, oxidative phosphorylation, mitochondrial functions, respiratory cycle, browning of adipocytes and thermogenesis.

| Gene | Ensembl | Gene | Ensembl | Gene | Ensembl |
| --- | --- | --- | --- | --- | --- |
| COBL | ENSG00000106078 | NCOA1 | ENSG00000084676 | TCF7L2 | ENSG00000148737 |
| COL1A2 | ENSG00000164692 | NCOA2 | ENSG00000140396 | TF | ENSG00000091513 |
| COL3A1 | ENSG00000168542 | NCOA3 | ENSG00000108064 | TFAM | ENSG00000108064 |
| COQ10A | ENSG00000135469 | NCOR2 | ENSG00000196498 | TGFB1 | ENSG00000105329 |
| COQ7 | ENSG00000167186 | ND1 | ENSG00000198888 | TGFB1I1 | ENSG00000140682 |
| COQ9 | ENSG00000088682 | ND2 | ENSG00000198763 | TGM2 | ENSG00000198959 |
| COX1 | ENSG00000198804 | ND3 | ENSG00000198840 | THRA | ENSG00000126351 |
| COX10 | ENSG00000006695 | ND4 | ENSG00000198886 | THRSP | ENSG00000151365 |
| COX11 | ENSG00000166260 | ND4L | ENSG00000212907 | THY1 | ENSG00000154096 |
| COX14 | ENSG00000178449 | ND5 | ENSG00000198786 | TIMM21 | ENSG00000075336 |
| COX15 | ENSG00000014919 | ND6 | ENSG00000198695 | TLE3 | ENSG00000140332 |
| COX17 | ENSG00000138495 | NDRG2 | ENSG00000165795 | TMED5 | ENSG00000117500 |
| COX18 | ENSG00000163626 | NDUFA1 | ENSG00000125356 | TMEM126B | ENSG00000171204 |
| COX19 | ENSG00000240230 | NDUFA10 | ENSG00000130414 | TMEM26 | ENSG00000196932 |
| COX2 | ENSG00000198712 | NDUFA11 | ENSG00000174886 | TMEM38A | ENSG00000072954 |
| COX20 | ENSG00000203667 | NDUFA12 | ENSG00000184752 | TNFRSF1A | ENSG00000067182 |
| COX3 | ENSG00000198938 | NDUFA13 | ENSG00000186010 | TNFRSF21 | ENSG00000146072 |
| COX4I1 | ENSG00000131143 | NDUFA2 | ENSG00000131495 | TNFRSF9 | EN5G00000049249 |
| COX4I2 | ENSG00000131055 | NDUFA3 | ENSG00000170906 | TOMM5 | ENSG00000175768 |
| COX5A | ENSG00000178741 | NDUFA4 | ENSG00000189043 | TRIM33 | ENSG00000197323 |
| COX5B | ENSG00000135940 | NDUFA4L2 | ENSG00000185633 | TRIM67 | ENSG00000119283 |
| COX6A1 | ENSG00000111775 | NDUFA5 | ENSG00000128609 | TRMT10C | ENSG00000174173 |
| COX6A2 | ENSG00000156885 | NDUFA6 | ENSG00000184983 | TRMT2B | ENSG00000188917 |
| COX6B1 | ENSG00000126267 | NDUFA7 | ENSG00000167774 | TRPM8 | ENSG00000144481 |
| COX6B2 | ENSG00000160471 | NDUFB8 | ENSG00000166136 | TRPV4 | ENSG00000111199 |
| COX6C | ENSG00000164919 | NDUFB9 | ENSG00000147684 | TSC22D3 | ENSG00000157514 |
| COX7A1 | ENSG00000161281 | NDUFC1 | ENSG00000109390 | TSPAN13 | ENSG00000106537 |
| COX7A2 | ENSG00000112695 | NDUFC2 | ENSG00000151366 | TSPAN14 | ENSG00000108219 |
| COX7A2L | ENSG00000115944 | NDUFS1 | ENSG00000023228 | TSPAN3 | ENSG00000140391 |
| COX7B | ENSG00000131174 | NDUFS2 | ENSG00000158864 | TSPAN4 | ENSG00000214063 |
| COX7B2 | ENSG00000170516 | NDUFS3 | ENSG00000213619 | TSPO | ENSG00000100300 |
| COX7C | ENSG00000127184 | NDUFS4 | ENSG00000164258 | TWIST1 | ENSG00000122691 |
| COX8A | ENSG00000176340 | NDUFS5 | ENSG00000168653 | UCP1 | ENSG00000109424 |
| COX8C | ENSG00000187581 | NDUFS6 | ENSG00000145494 | UCP2 | ENSG00000175567 |
| CPB1 | ENSG00000153002 | NDUFS7 | ENSG00000115286 | UCP3 | ENSG00000175564 |
| CPNE1 | ENSG00000214078 | NDUFS8 | ENSG00000110717 | UQCC | ENSG00000101019 |
| CPNE3 | ENSG00000085719 | NDUFV1 | ENSG00000167792 | UQCR10 | ENSG00000184076 |
| CPT1A | ENSG00000110090 | NDUFV2 | ENSG00000178127 | UQCR11 | ENSG00000127540 |
| CPT1B | ENSG00000205560 | NDUFV3 | ENSG00000160194 | UQCRB | ENSG00000156467 |
| CPT2 | ENSG00000157184 | NEGRI | ENSG00000172260 | UQCRC1 | ENSG00000010256 |
| CRAT | ENSG00000095321 | NEU3 | ENSG00000162139 | UQCRC2 | ENSG00000140740 |
| CREB1 | ENSG00000118260 | NFE2L2 | ENSG00000116044 | UQCRFS1 | ENSG00000169021 |
| CREBBP | ENSG00000204116 | NFYC | ENSG00000066136 | UQCRH | ENSG00000173660 |
| CRHR2 | ENSG00000106113 | NNAT | ENSG00000053438 | UQCRQ | ENSG00000164405 |
| CTBP1 | ENSG00000159692 | NPC1L1 | ENSG00000015520 | UTRN | ENSG00000152818 |
| CTBP2 | ENSG00000175029 | NPC2 | ENSG00000119655 | VDR | ENSG00000111424 |
| CTNNB1 | ENSG00000168036 | NPPA | ENSG00000175206 | VEGFA | ENSG00000112715 |
| CYB5R3 | ENSG00000100243 | NPR1 | ENSG00000169418 | VGF | ENSG00000128564 |
| CYC1 | ENSG00000179091 | NPR2 | ENSG00000159899 | VLDLR | ENSG00000147852 |
| CYCS | ENSG00000172115 | NPR3 | ENSG00000113389 | WDFY1 | ENSG00000085449 |
| CYFIP2 | ENSG00000055163 | NR0B2 | ENSG00000131910 | WISP2 | ENSG00000064205 |
| CYP26B1 | ENSG00000003137 | NR1H3 | ENSG00000025434 | WNT1 | ENSG00000125084 |
| CYP46A1 | ENSG00000036530 | NR2F6 | ENSG00000160113 | WNT10B | ENSG00000169884 |
| CYP4B1 | ENSG00000142973 | NR3C1 | ENSG00000113580 | WNT3A | ENSG00000154342 |
| CYTB | ENSG00000198727 | NR4A3 | ENSG00000119508 | WNT5A | ENSG00000114251 |
| DBI | ENSG00000155368 | NRF1 | ENSG00000106459 | WNT5B | ENSG00000111186 |
| DCN | ENSG00000011465 | NRIP1 | ENSG00000180530 | WTAP | ENSG00000146457 |
| DDIT3 | ENSG00000175197 | NUBPL | ENSG00000151413 | YIF1B | ENSG00000167645 |
| DDO | ENSG00000203797 | OCIAD1 | ENSG00000109180 | YWHAH | ENSG00000128245 |
| DECR1 | ENSG00000104325 | OPA1 | ENSG00000198836 | ZFYVE1 | ENSG00000165861 |
| DGAT1 | ENSG00000185000 | OPRD1 | ENSG00000116329 | ZFYVE16 | ENSG00000039319 |
| DGAT2 | ENSG00000062282 | OSBP | ENSG00000110048 | ZIC1 | ENSG00000152977 |
| DIO2 | ENSG00000211448 | OXA1L | ENSG00000155463 | | |
| DLD | ENSG00000091140 | PAFAH2 | ENSG00000158006 | | |
| FABP5 | ENSG00000164687 | PANK1 | ENSG00000152782 | | |
| FABP7 | EN5G00000164434 | PC | ENSG00000173599 | | |
| FADS1 | ENSG00000149485 | PCK1 | ENSG00000124253 | | |
| FADS2 | ENSG00000134824 | PCLO | ENSG00000186472 | | |
| FAM210A | ENSG00000177150 | PCTP | ENSG00000141179 | | |
| FASN | ENSG00000169710 | PDCD6IP | ENSG00000170248 | | |
| FFAR2 | ENSG00000126262 | PDE4D | ENSG00000113448 | | |

1.1.5 Example 3

1.1.6 In Vitro Validation of miR-22-3p Inhibition

In vitro validation of miRNA candidates (miRIDIAN microRNA Hairpin Inhibitors ordered from Dharmacon GE, CO) was carried out in primary cultures of human subcutaneous adipocytes, the ultimate targets for an anti-obesity drug (clinical trial in a dish) as depicted in FIG. 3A. A preliminary experiment suggested that a human miR-22-3p inhibitor induced several fold increases of UCP1 and UCP2 gene expression, whereas the expression of UCP3 was not altered, as assessed at Day 14 after a single transfection at Day 3.

Subsequent mRNA Profiling was done (n=3 per condition) by Next Generation Sequencing (Illumina HiSeq 2500) and the following bioinformatic analyses were performed:

1.1.7 Example 4

1.1.8 Individual Gene Expression Statistical Analysis (Ensembl Project Human Genome Database)

For the 60 target genes of miR-22-3p from the curated list, the following criteria were analyzed:
Level of expression in control condition and in the presence of the miR-22-3p inhibitor
Changes of gene expression levels in the presence of miR-22-3p vs. control
Several statistical parameters
In this experimental setting, the expression of 18 of these 60 target genes were significantly altered: CEBPD, CREB1, EIF4EBP2, KDM3A, KDM6B, KLF11, KLF6, LAMC1, MFGE8, NAA20, NCOA1, PPARA, PPARGC1B, PRDX3, RUNX2, SIRT1, TRPM8 and UCP1 (FIG. 3B).

1.1.9 Example 5

1.1.10 Gene Set Enrichment Analysis (GSEA) Analysis

Figure 3C:
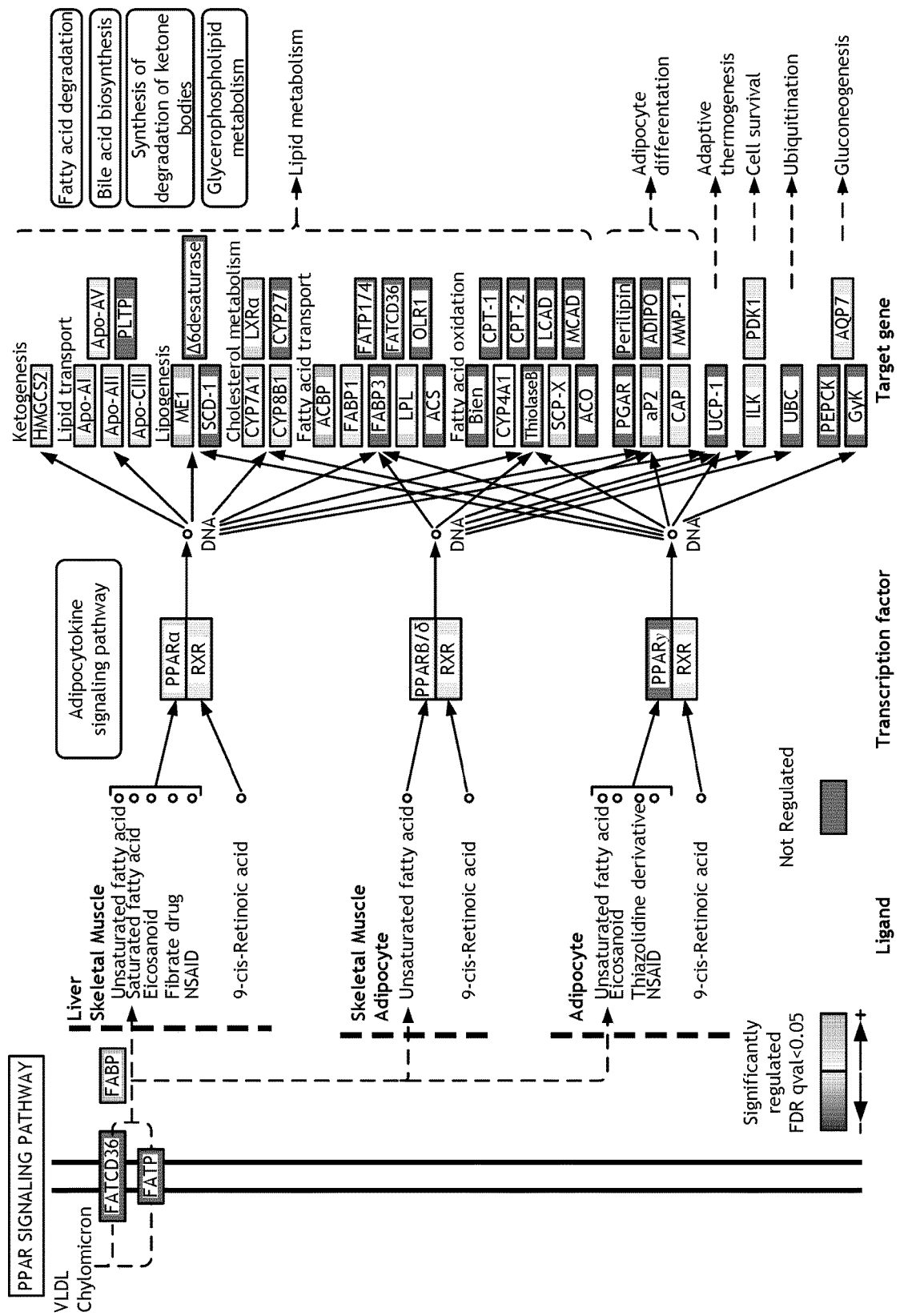

Using the GO pathway database, 129 pathways were found which were enriched in human adipocytes in culture in the presence of the miR-22-3p inhibitor, at nominal p value<1%. According to the Kyoto Encyclopedia of Genes and Genomes (KEGG) resource, it appears that the PPAR signaling pathway is activated in human adipocytes in culture in the presence of the miR-22-3p inhibitor (FIG. 3C).

The expression level of genes involved in the PPAR Signaling Pathway in the presence of KDM3A inactivation by knock out (Zhang et al. 2009, microarray data) or KDM3A activation by miR-22-3p inhibition (RNA Seq data) were compared. In most cases, opposite effects of these two interventions were noted, thus supporting that the anti-obesity and beneficial metabolic effects of miR-22 inhibition are mediated by the PPAR Signaling Pathway (data not shown).

1.1.11 Example 6

1.1.12 Beneficial Metabolic Effects of miR-22 Inhibition in Diet Induced Obesity (DIO) Mice To assess the metabolic effects of miR-22 inhibition, DIO C57BL/6J male mice (Kanasaki, K. et al., 2011) of various ages were treated with a miR-22 inhibitor for up to 3 months.

1.1.13 Example 6A

1.1.14 Reduction of High Fat Diet-Induced Weight Gain in Young Adult Mice Treated for 8 Weeks with a miR-22 Inhibitor A study of miR-22-3p inhibition was conducted in the initial phase of DIO in 6-week old C57BL/6J Male Mice. After acclimation for one week, DIO was induced in young adult (6-week old) DIO C57BL/6J male mice by feeding them a 60% high fat diet (Research Diet D12492) which was provided ad libitum for the subsequent 8 weeks of the study. The mice (n=8 per group) received subcutaneous injections in the left inguinal fat pad of saline or commercially available (Exiqon, MA) scrambled miRNA inhibitor (15 mg/kg), or miR-22-3p inhibitor (15 mg/kg) on days 0, 2, and 4 of the first week, then once a week for the next 7 weeks.

TABLE 3

| | | Group Assignment | | | |
|---|---|---|---|---|---|
| Group | N | Test Article | Dose (mg/kg) | Route | Dose Schedule |
| 1 | 8 | 1 x PBS | n/a | SC | Days 0, 2, 4 and QW thereafter |
| 2 | 8 | Scrambled miRNA inhibitor | 15 | SC | Days 0, 2, 4 and QW thereafter |
| 3 | 8 | miR-22-3p inhibitor | 15 | SC | Days 0, 2, 4 and QW thereafter |

Figure 4A:
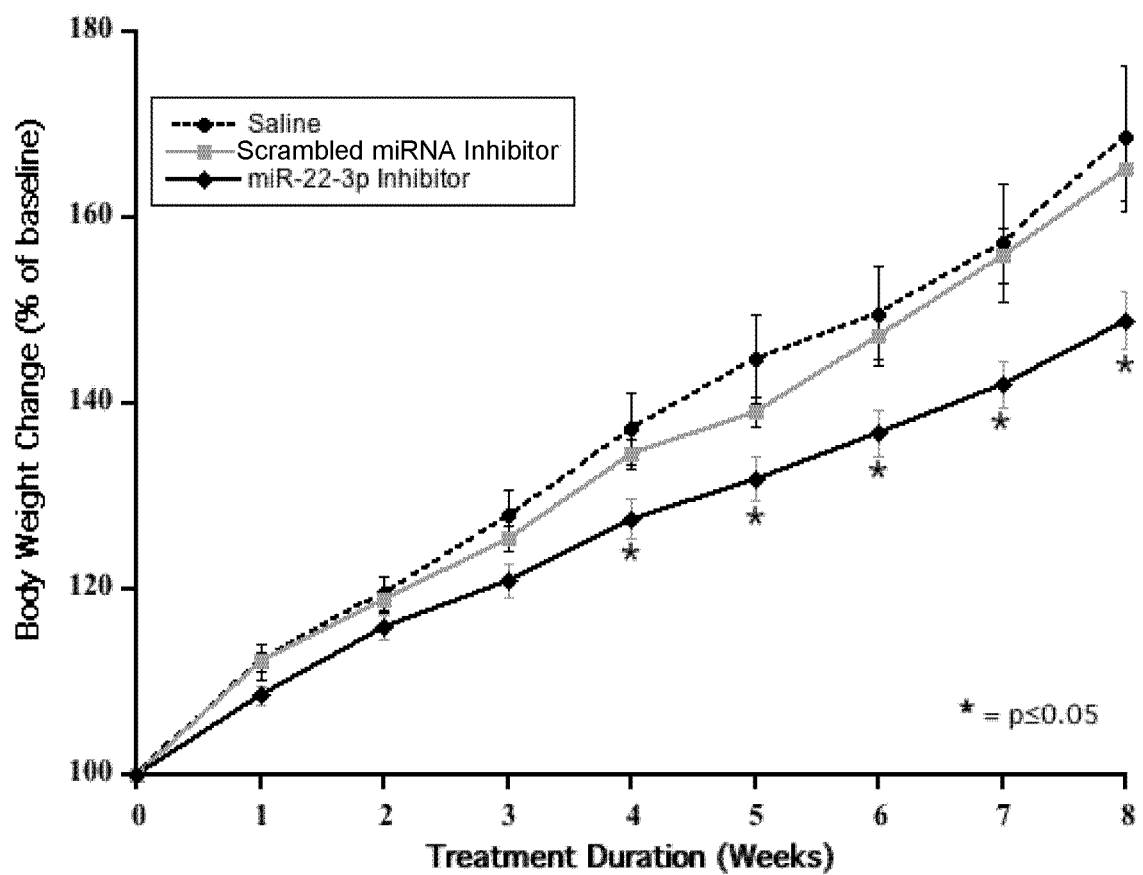
FIGS. 4A-4B.

Definitions:
n/a = not applicable;
PBS = phosphate buffered saline;
SC = subcutaneous Body weight changes were calculated for each mouse by subtracting the body weight on the first day of dosing (baseline) from the body weight on the subsequent day of dosing and calculating the percent change from baseline body weight. Average percent body weight change±SEM was then calculated by treatment group. As shown on FIG. 4A, there was a steady increase of body weight over the 8-week duration of the study in all 3 groups due to the consumption of the 60% high fat diet. However, the weights recorded on the 60% fat diet were lower in the miR-22-3p inhibitor group. At the end of 8 weeks of high fat diet (14-week old mice), the miR-22-3p inhibitor group gained 29% less weight than the saline group and 25% less weight than the scrambled miRNA group (p≤0.05).

The reduced weight gain in the miR-22-3p inhibitor group was not explained by a reduction in food consumption as this group seemed to eat more food over the 8 weeks of treatment (50.83±0.06, 51.88±0.10 and 58.55±0.15 grams over 8 weeks in the saline, scrambled miRNA inhibitor and miR-22-3p inhibitor groups, respectively, p≤0.01).

Figure 4B:
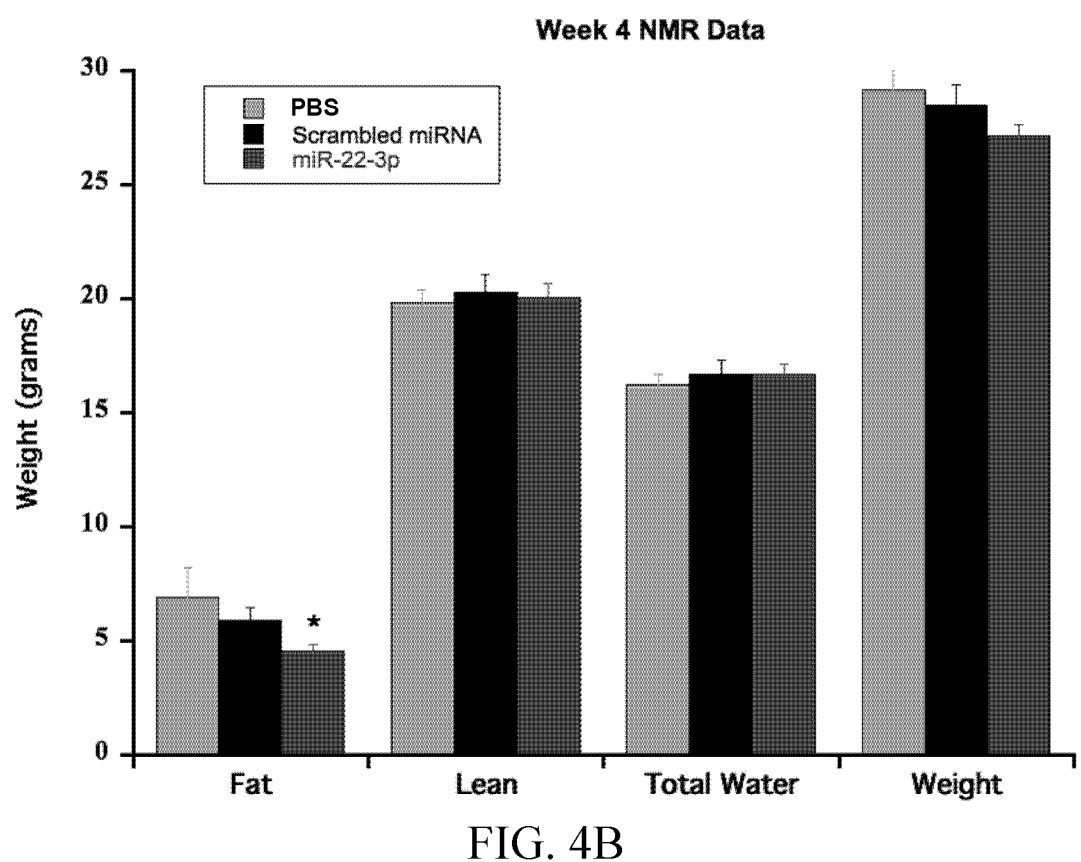
Figure 4C:
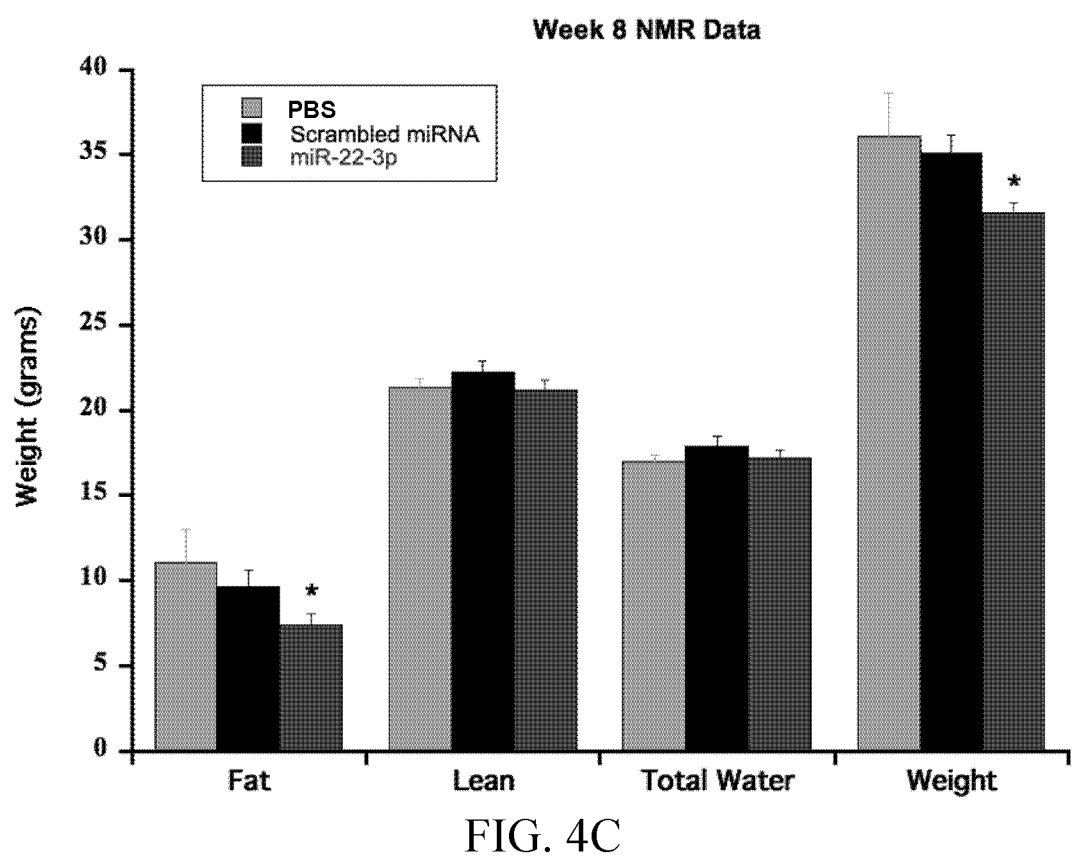
FIG. 4C Body composition by NMR analysis of C57Bl/J6 young male mice on 60% high fat diet alone (saline, gray columns) or in the presence of a scrambled miRNA inhibitor (black columns) or a miR-22-3p inhibitor (red columns) at week 8 of treatment.

Body composition was assessed by NMR analysis at Week 4 and at Week 8 of the study. Fat mass, lean mass, total water, and total body weight measurements (g±SEM) were averaged by treatment group. At Week 4 and Week 8, the miR-22-3p inhibitor group showed a reduction of fat mass and total body weight, whereas its lean and total water fractions were similar to the two control groups (FIG. 4B).

In addition to weight gain reduction over time, the miR-22-3p inhibitor group displayed a significant improvement of random non fasting blood glucose (226±12 mg/dl vs. 289±9 mg/dl, p=0.0015), serum insulin (6.3±1.09 ng/ml vs. 10±2 ng/ml, p=0.01) and serum cholesterol (126±4 mg/dl vs. 175±14 mg/dl, p=0.0011) vs. the saline group. Liver function tests were within normal ranges in all 3 groups.

The following organs/tissues were collected at the end of the study: heart, liver, spleen, inguinal fat, peri-renal fat, subscapular fat (Table 4). There was no difference of heart, liver and spleen weights across the 3 groups. The group treated with the miR-22-3p inhibitor displayed a significant reduction of inguinal (–46%, p=0.032), peri-renal (–47%, p=0.017) and subscapular fat (–67%, p=0.004) depots in comparison to the saline group.

TABLE 4

Anatomy Analysis Results

| Tissue/organ (grams, Mean ± SEM) | PBS | miR-22-3p inhibitor |
|---|---|---|
| Heart | 0.178 ± 0.022 | 0.142 ± 0.005 |
| Liver | 1.217 ± 0.063 | 1.192 ± 0.066 |
| Spleen | 0.082 ± 0.004 | 0.082 ± 0.007 |
| Inguinal fat | 1.074 ± 0.194 | 0.577 ± 0.055 * |
| Peri-renal fat | 0.924 ± 0.107 | 0.489 ± 0.053 * |
| Subscapular fat | 0.381 ± 0.101 | 0.127 ± 0.009 * |

1.1.15 Example 6B 1.1.16 Correction of Obesity Induced by High Fat Diet in Mature Adult Mice Treated for 8 Weeks A study of miR-22-3p inhibition was conducted in the established phase of DIO in 13-week old C57BL/6J Male Mice. Starting at 6-week old, DIO C57BL/6J male mice were fed ad libitum 60% high fat diet (Research Diet D12492) for 8 weeks. After acclimation for one week, the 14-week old mice (n=12 per group) were randomized according to similar body weights and allocated to either normal chow 10% fat diet (Research Diet D12450B) or kept on 60% high fat diet (Research Diet D12492). One group of mice on the 60% high fat diet received subcutaneous injections in the left inguinal fat pad of a commercially available (Exiqon, MA) miR-22-3p inhibitor (15 nucleotides long, 15 mg/kg) on days 0, 2, and 4 of the first week, then once a week for the next 7 weeks. The other two groups on either normal chow or the 60% high fat diet received saline injections instead.

TABLE 5

Group Assignment

| Group | N | Diet | Test Article | Dose (mg/kg) | Route | Dose Schedule |
|---|---|---|---|---|---|---|
| 1 | 12 | 10% kcal | 1 × PBS | n/a | SC | Days 0, 2, 4 and QW thereafter |
| 2 | 12 | 60% kcal | 1 × PBS | n/a | SC | Days 0, 2, 4 and QW thereafter |
| 3 | 12 | 60% kcal | miR-22-3p inhibitor | 15 | SC | Days 0, 2, 4 and QW thereafter |

Definitions: n/a = not applicable; QW = once weekly; SC = subcutaneous

Figure 5A:
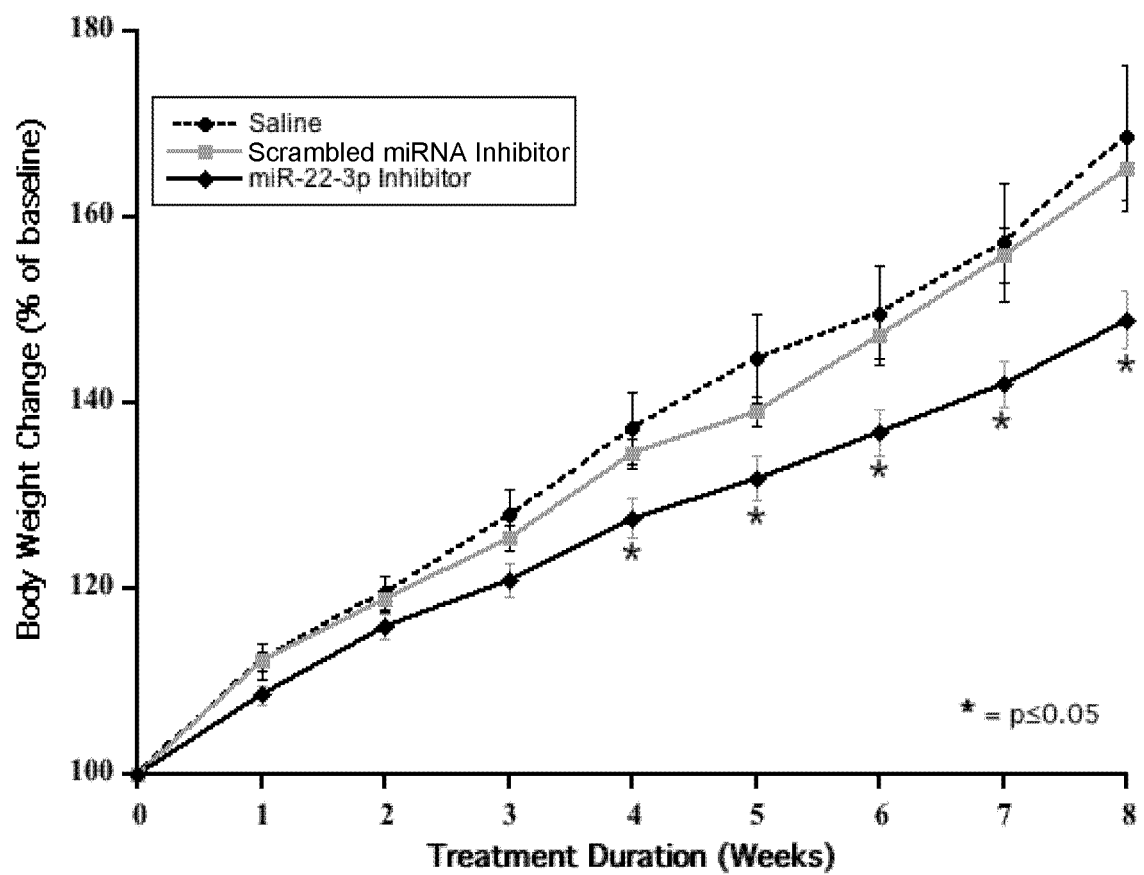
FIGS. 5A-5D.
Figure 5B:

At the end of 8 weeks of high fat diet (22-week old mice), the mice treated with the miR-22-3p inhibitor group kept a stable weight (35.51±0.76 grams at week 8 vs. 34.98±0.54 grams at Week 0) whereas the mice on the 60% high fat diet receiving saline injections kept gaining weight, reaching a 30% weight increase at week 8 (45.85±0.93 grams at week 8 vs. 35.14±0.47 grams at Week 0, p<0.0001) (FIGS. 5A-5B). The mice switched back to a normal chow at week 12 initially dropped their body weight for 2 weeks because of reduced consumption of less palatable food, then displayed an age-related moderate weight gain (+8%) at the end of the study (32.08±0.61 grams at week 8 vs. 29.71±0.40 grams at Week 0, p=0.004) while receiving saline injections.

There was no difference in food consumption between the saline and miR-22-3p inhibitor groups on 60% fat diet (70.57±1.51 and 69.98±1.35 grams over 8 weeks in the saline and miR-22-3p inhibitor groups, respectively) that could have explained the body weight differences. As expected, the group on 10% fat diet and saline injections ate less food (49.71±0.23 grams).

Figure 5C:
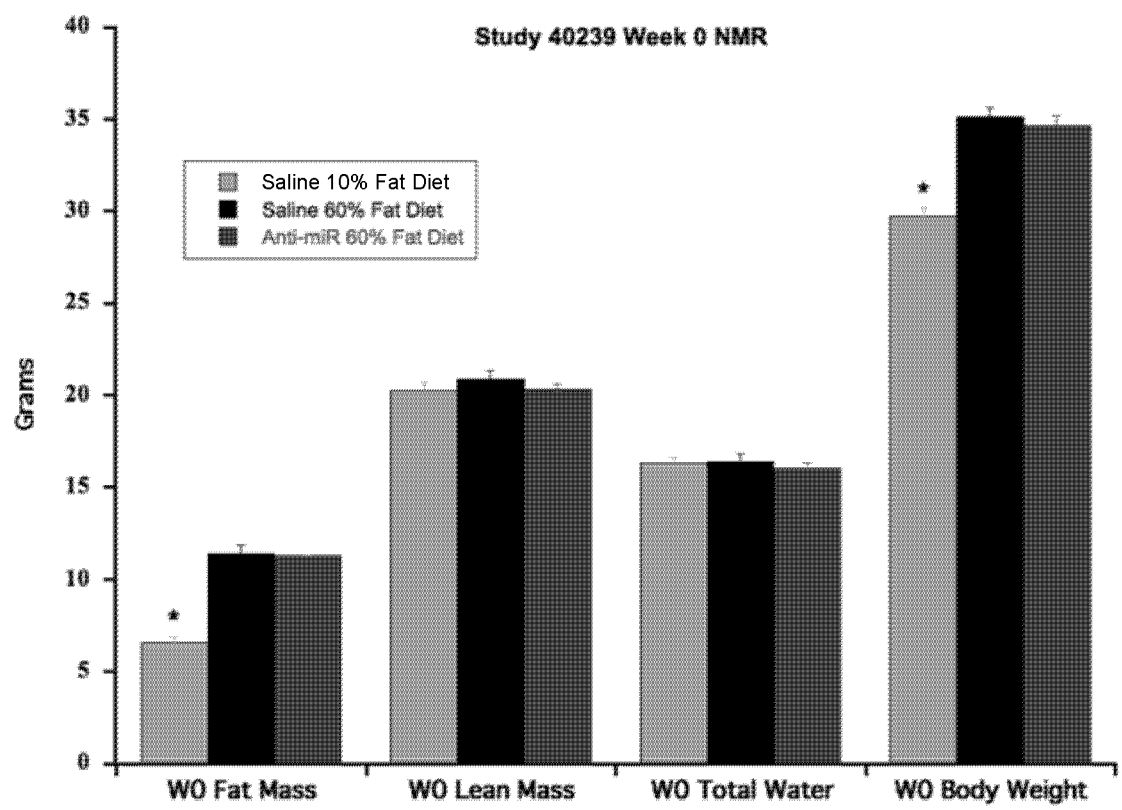

Body composition was measured by NMR at weeks 0, 4 and 8 of treatment (FIG. 5C). At baseline, body weight and fat mass were lower in the group that has been switched from 60% fat diet to 10% fat diet a week before. At week 4, as expected the fat mass was greater in the two groups kept on 60% fat diet versus the group switched to 10% fat diet. However fat mass was 21% lower in the miR-22-3p inhibitor group on 60% fat diet than that in the group on saline and 60% fat diet (11.99±0.47 grams vs. 15.20±0.78 grams, p<0.0003). Lean mass was similar across the 3 groups at week 4. At week 8, fat mass was 29% lower in the miR-22-3p inhibitor group on 60% fat diet than that in the group on saline and 60% fat diet (10.50±0.71 vs. 14.75±1.36 grams, p<0.0015). Lean mass was similar across the 3 groups at week 8.

Figure 5D:
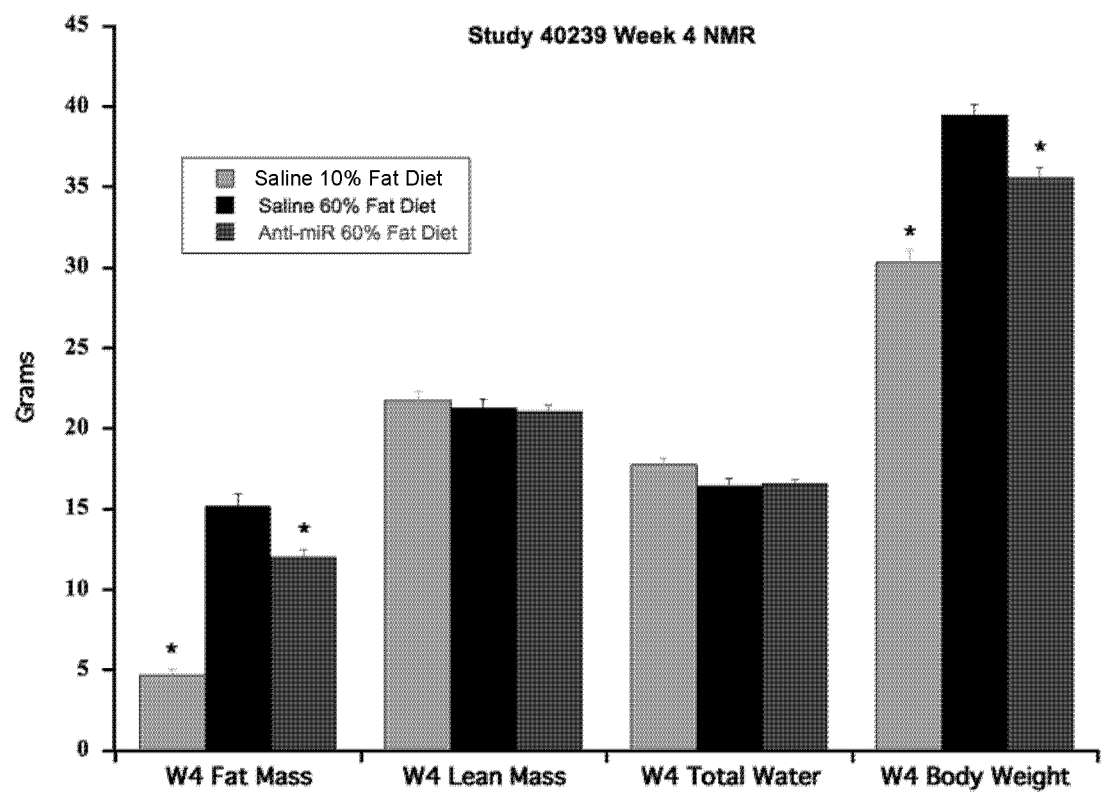
Figure 5E:
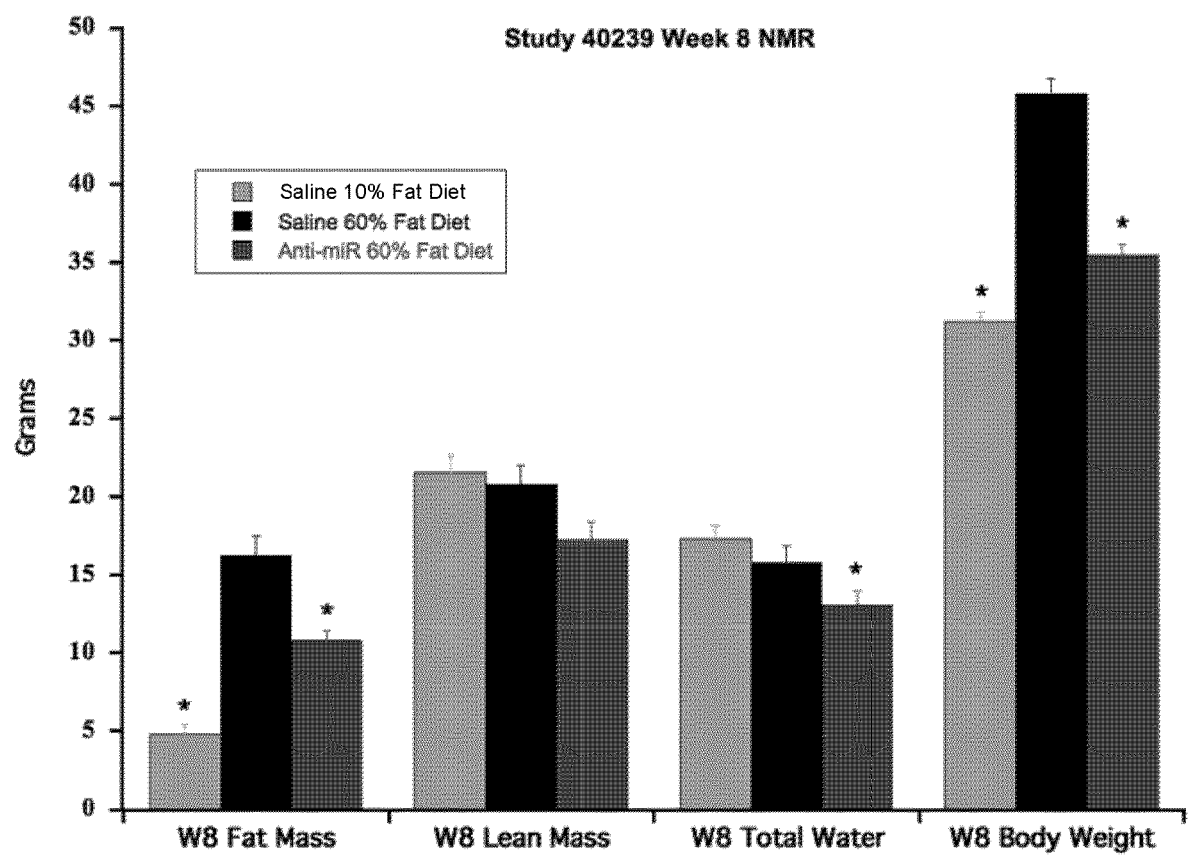
FIG. 5E Body composition measure by NMR analysis at week 8.
Figure 5F:
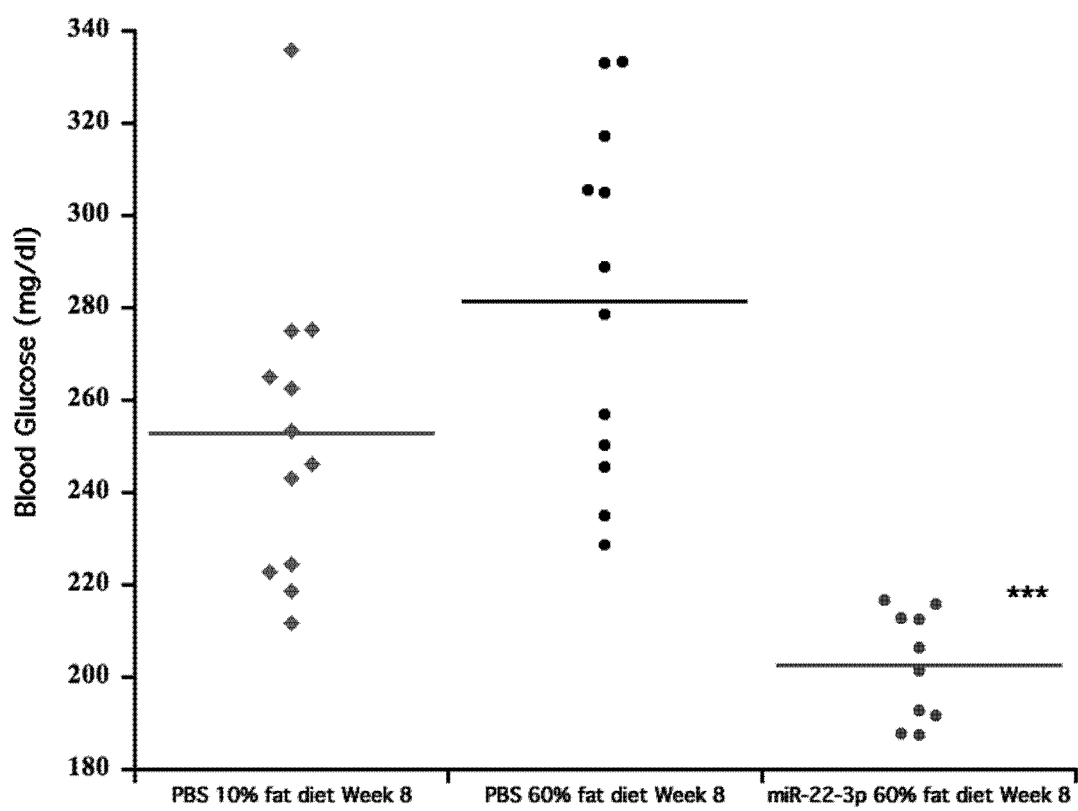
FIG. 5F Random non fasting blood glucose and serum cholesterol and insulin of 22-week old C57Bl/J6 adult male mice on normal diet.
Figure 5G:
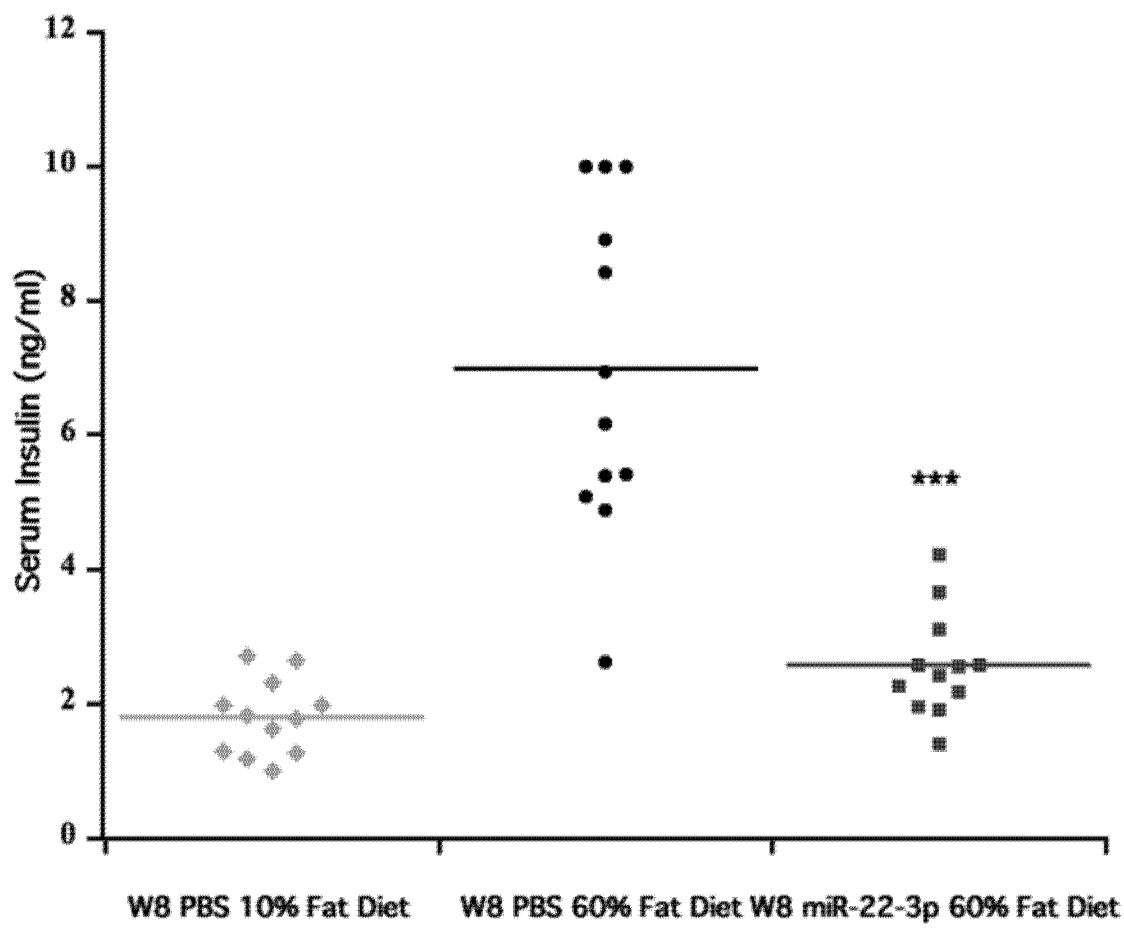
FIG. 5G Random non fasting blood glucose and serum cholesterol and insulin of 22-week old C57Bl/J6 adult male mice on 60% high fat diet alone.
Figure 5H:
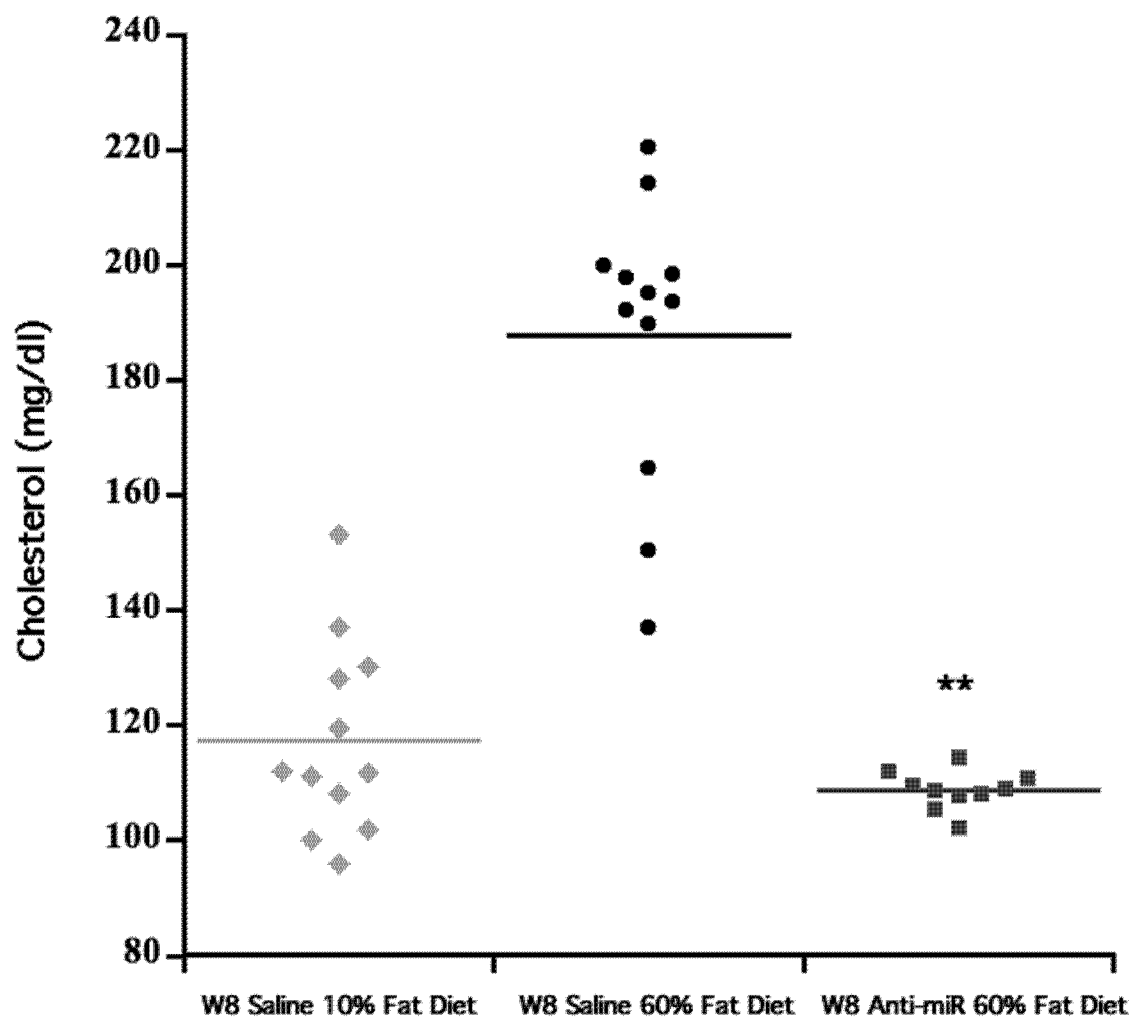
FIG. 5H Random non fasting blood glucose and serum cholesterol and insulin of 22-week old C57Bl/J6 adult male mice on 60% high fat diet plus a miR-22-3p inhibitor at the end of 8 weeks of treatment.

In addition to weight control over time, the miR-22-3p inhibitor group on 60% fat diet displayed a significant improvement of random non fasting blood glucose versus the group on saline and 60% fat diet (203±4 mg/dl vs. 282±11 mg/dl, P<0.0001) at the end of the study (Week 22) (FIG. 5D). The blood glucose at week 22 of the miR-22-3p inhibitor group on 60% fat diet was lower than that of the group on saline that was switched back to 10% fat diet at week 13 (203±4 mg/dl vs. 253±10 mg/dl, p=0.0017), possibly reflecting the metabolic insult (60% fat diet) these animals experienced between weeks 6 and 13 before they were switched back to normal chow. Also at week 22, serum insulin (2.56±0.22 ng/ml vs. 6.99±0.71 ng/ml, p<0.001) and serum cholesterol (109±1 mg/dl vs. 188±7 mg/dl, p<0.0001) were improved in the miR-22-3p inhibitor group on 60% fat diet vs. the saline group on 60% fat diet, reaching values similar to those of the group on 10% fat diet (insulin: 1.80±0.16 ng/ml, cholesterol: 117±5 mg/dl). Liver function tests were within normal ranges in all groups.

Body temperature was measured with a rectal probe during weeks 1, 4 and 8 of the study. No difference was recorded between the 3 groups. At the end of the study, body temperature was 35.51±0.11° C., 35.80±0.17° C. and 36.04±0.12° C. in the 10% fat saline, 60% fat saline and 60% fat miR-22-3p inhibitor groups, respectively (p=0.742, Kruskal-Wallis Rank Sum Test). This suggests that the weight loss observed in the hsa-miR-22-3p inhibitor group was not caused by hyperthermia.

The following organs were collected at the end of the study: liver, spleen, inguinal fat, peri-renal fat, and subscapular fat (Table 6). There was no difference of liver and spleen weights across the 3 groups. The 60% high fat diet group treated with the miR-22-3p inhibitor displayed a size reduction of inguinal (–48%), perirenal (–34%) and subscapular fat (–38%) depots compared to the 60% high fat diet group treated with saline (all p<0.001).

TABLE 6

Anatomy Analysis Results

| Tissue/organ | Weight (g)/Mean ± SEM | | |
|---|---|---|---|
| | PBS on 10% fat diet | PBS on 60% fat diet | miR-22-3p inhibitor on 60% fat diet |
| Liver | 1.417 ± 0.042 | 1.649 ± 0.098 | 1.509 ± 0.078 |
| Spleen | 0.086 ± 0.006 | 0.098 ± 0.007 | 0.105 ± 0.003 |
| Inguinal fat | 0.448 ± 0.036 | 2.271 ± 0.136 | 1.180 ± 0.082* |
| Peri-renal fat | 0.880 ± 0.065 | 2.708 ± 0.108 | 1.788 ± 0.138* |
| Subscapular fat | 0.140 ± 0.009 | 0.322 ± 0.017 | 0.201 ± 0.014* |

A similar study was performed in 14-week old mice (n=9 per group) which were randomized into 2 groups according to similar body weights and kept on 60% high fat diet (Research Diet D12492) for 6 weeks. One group of mice received subcutaneous injections in the left inguinal fat pad of a custom-designed miR-22-3p inhibitor (APT-110, 18 nucleotides long, 15 mg/kg) on days 0, 2, and 4 of the first week, then once a week for the next 5 weeks. The other group kept on 60% high fat diet received saline injections.

At the end of 6 weeks of high fat diet (20-week old mice), the mice treated with the APT-110 miR-22-3p inhibitor displayed a 6% age-dependent weight increase (36.16±0.67 grams at week 6 vs. 34.15±0.53 grams at Week 0) whereas the mice on the 60% high fat diet receiving saline injections gained more weight, reaching a 22% weight increase at week 6 (41.73±1.07 grams at week 6 vs. 34.19±0.79 grams at Week 0, p<0.0001) (FIG. 6). The difference between the two groups became significant as of week 4 on treatment. There was no difference in food consumption between the two groups that could have explained the body weight differences.

Body composition was measured by NMR at the end of the study (week 6 of treatment). Fat mass was 30% lower in the APT-110 miR-22-3p inhibitor group on 60% fat diet than that in the control group on saline and 60% fat diet (11.29±0.87 vs. 16.11±0.87 grams, p<0.0017). Lean mass was similar in both groups at week 6 of treatment (21.74±0.99 vs. 22.33±0.63 grams).

Blood glucose measured after fasting for 4 hours on Day 35 of treatment was significantly lower in the APT-110 miR-22-3p inhibitor group than in the group treated with saline (183±11 mg/dl vs. 245±8 mg/dl, P<0.01). Similarly, random blood glucose measured on Day 44 of treatment at the time of necropsy was significantly lower in the group treated with the APT-110 miR-22-3p inhibitor than in the group treated with saline (212±12 mg/dl vs. 341±9 mg/dl, P<0.0001). Also at the time of necropsy, serum cholesterol was improved in the miR-22-3p inhibitor group on 60% fat diet vs. the saline group on 60% fat diet (110±5 mg/dl vs. 164±6 mg/dl, p<0.0001).

The following organs were collected at the end of the study: Liver, heart, inguinal fat, peri-renal fat, and subscapular fat (Table 7). There was no difference of liver and heart weights across the 2 groups.

TABLE 7

Anatomy Analysis Results

| Tissue/organ | Weight (g)/Mean ± SEM | |
|---|---|---|
| | PBS on 60% fat diet | miR-22-3p inhibitor on 60% fat diet |
| Liver | 1.371 ± 0.066 | 1.507 ± 0.074 |
| Heart | 0.181 ± 0.012 | 0.155 ± 0.006 |
| Inguinal fat | 1.757 ± 0.164 | 1.133 ± 0.154* |
| Peri-renal fat | 0.935 ± 0.083 | 0.593 ± 0.095* |
| Subscapular fat | 0.218 ± 0.023 | 0.133 ± 0.008* |

Figure 6A:
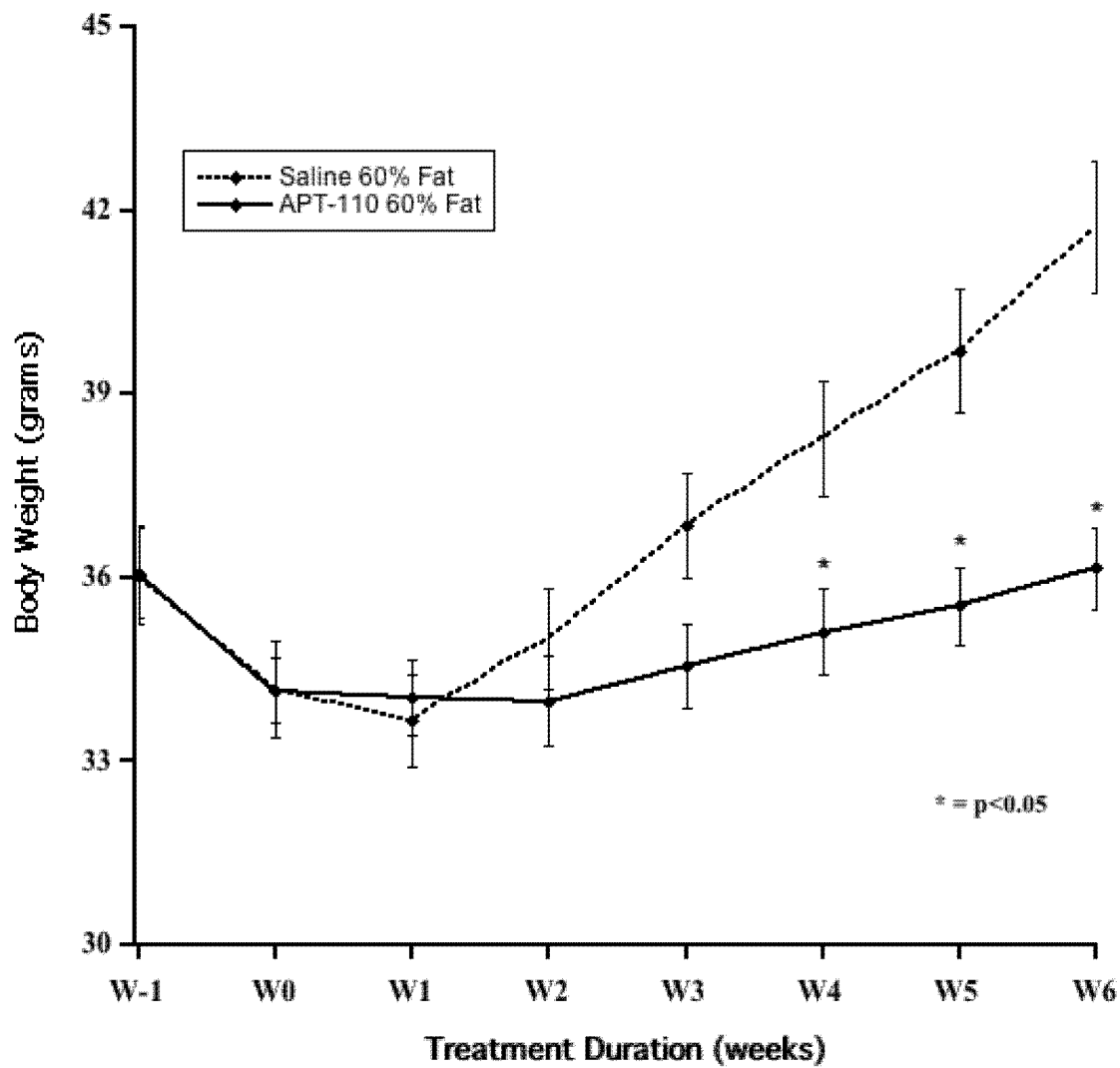
FIGS. 6A-6B.
Figure 6B:
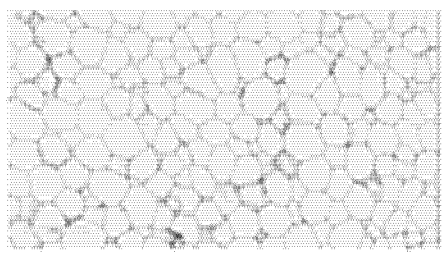
Figure 6B:
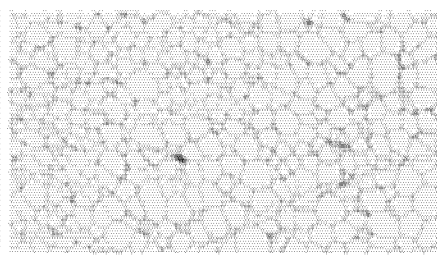
Figure 6B:
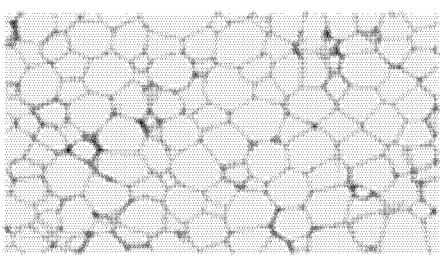
Figure 6B:
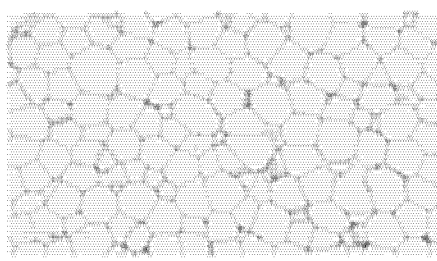
Figure 6B:
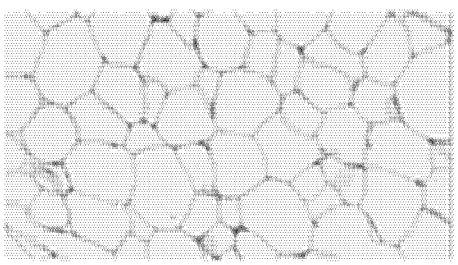
Figure 6B:
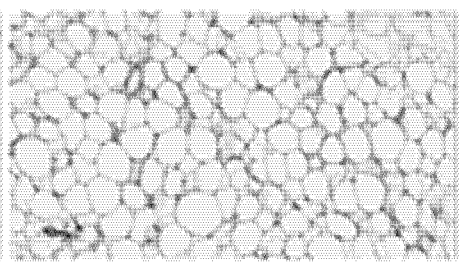
Figure 6B:
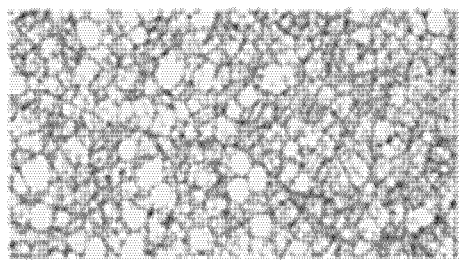
Figure 6B:
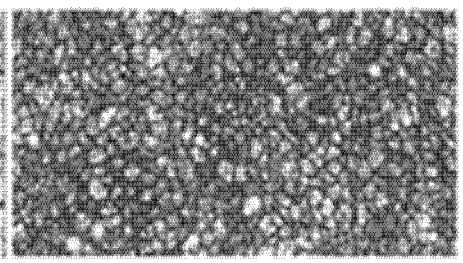

The average size of adipocytes was reduced in all three types of adipose tissues in the 60% high fat diet group treated with the miR-22-3p inhibitor (FIG. 6B).

1.1.17 Example 7

1.1.18 Increase of Energy Expenditure Induced by miR-22 Inhibition

To assess the effects of miR-22 inhibition on mitochondrial mass and activity, metabolic rate and energy expenditure, in vitro and in vivo experiments were carried out. In vitro intra-cellular assessment of mitochondrial mass and activities, as well as energy expenditure during miR-22 inhibition of human subcutaneous adipocytes were examined. In the model of primary culture of human subcutaneous adipocytes differentiated for 3 days, then transfected with 50 nM of the miR-22-3p inhibitor APT-110 and maintained in culture (n=6 per condition), the following parameters were assessed on Day 14.

1.1.19 Example 8

1.1.20 Mitochondrial Content/Mass by MitoTracker

A significant increase of mitochondrial mass/activity was noted in the presence of the miR-22-3p inhibitor, similar to that observed in the presence of a positive control (PPARG agonist Rosiglitazone, 100 nM), although the cell density was significantly higher (3 times more cells) in the presence of rosiglitazone, a well-known adipogenic agent. At Day 14 of culture, about 60% of cells seem to have converted into "beige cells" with increased mitochondrial mass in the presence of miR-22-3p inhibition, similar to what was observed in the presence of Rosiglitazone.

UCP-1 protein expression by immunofluorescence with UCP-1 abcam antibody 10983 (FIG. 8B): A significant increase of UCP1 immunostaining was noted in the presence of the miR-22-3p inhibitor. The number of "UCP1 positive" cells was higher in the presence of the mir-22-3p inhibitor (85±3%, p≥0.0001) than in the presence of PBS (48±3%) or rosiglitazone (58±2%).

1.1.21 Example 9

1.1.22 In Vitro Extra-Cellular Assessment of Energy Expenditure During miR-22 Inhibition of Human Subcutaneous Adipocytes To characterize the effects of miR-22-3p inhibition on energy utilization in human subcutaneous adipocytes in culture, $O_2$ consumption rate (OCR) was measured with the XF24 Analyzer (Seahorse Bioscience) using the XF Palmitate-BSA Fatty Acid Oxidation substrate kit during the successive addition of Oligomycin, FCCP, and Antimycin/Rotenone, following the manufacturer instructions.

Human subcutaneous pre-adipocytes (ZenBio, NC) were seeded into 96-well plates and differentiated for 7 days, then placed in maintenance medium according to the manufacturer's instructions. On Day 14, the adipocytes were transfected with 50 nM of the miR-22-3p inhibitor APT-110. Medium was exchanged every 2 to 3 days and Seahorse assay was performed on Day 21. Negative control was bovine serum albumin (BSA) and positive control was 100 nM rosiglitazone throughout the culture.

Figure 7A:
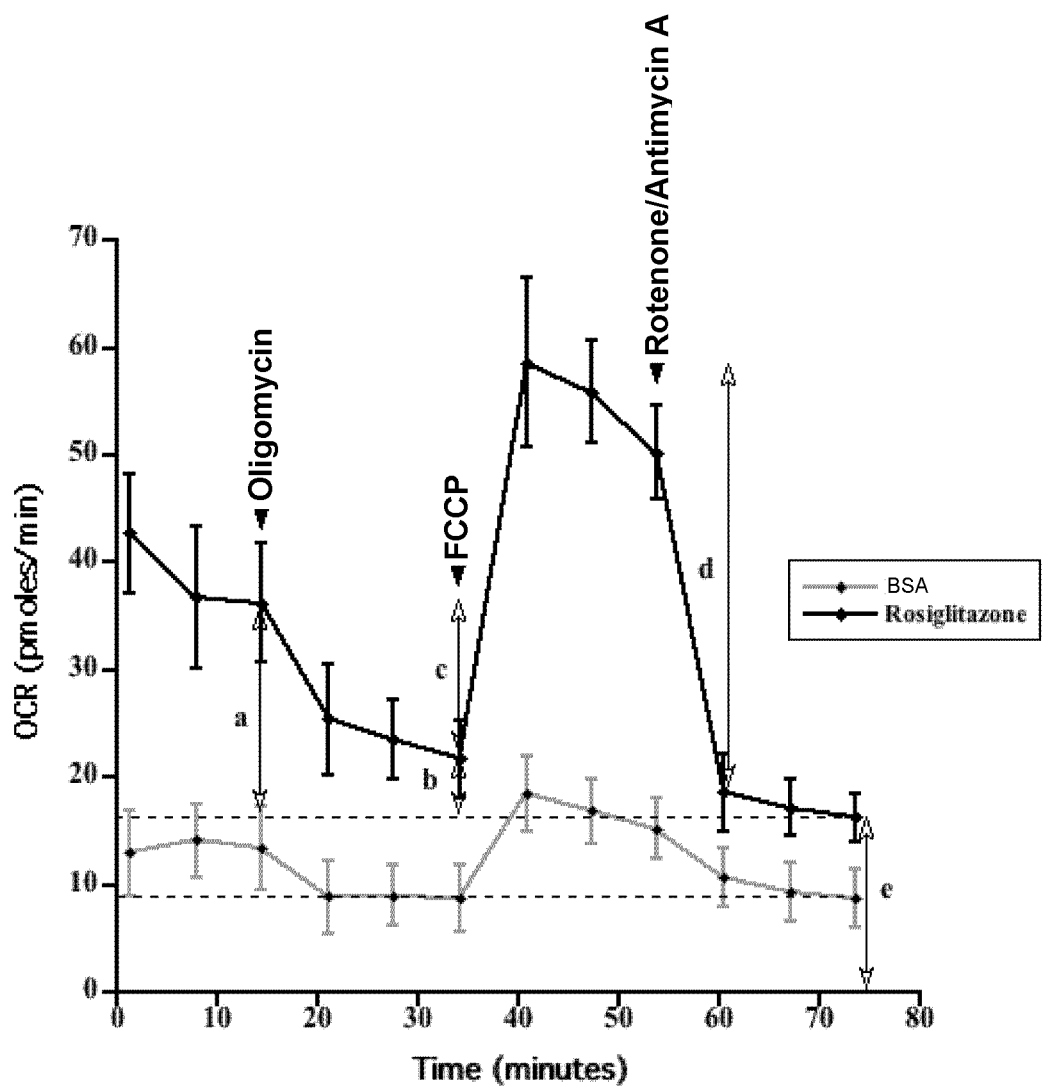
FIGS. 7A-7F.
Figure 7B:
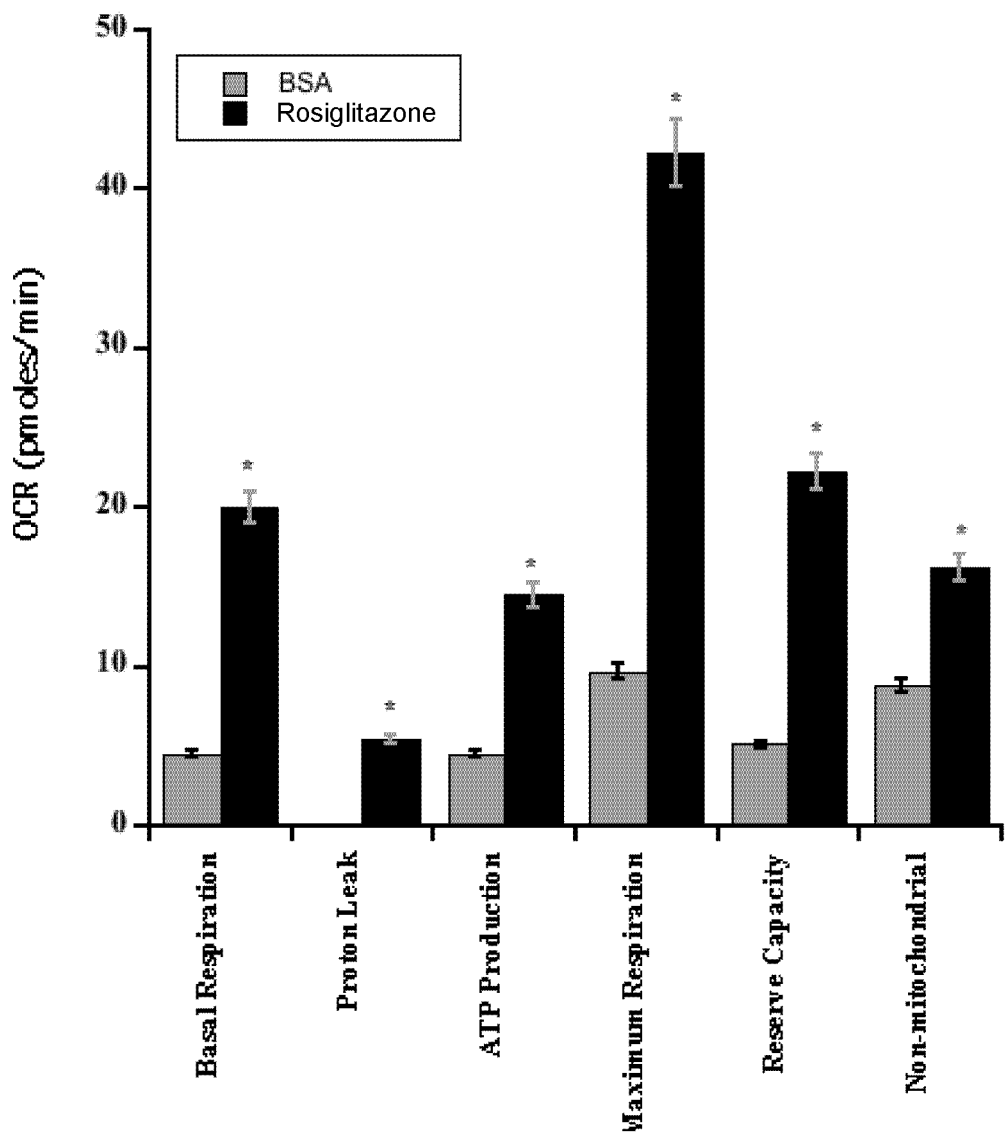

FIG. 7A shows OCR at baseline, then after addition of oligomycin (to assess ATP production and proton leak), FCCP (to assess maximum respiration) and Antimycin A+Rotenone (to assess reserve capacity and non-mitochondrial respiration) in control condition (BSA) and in the presence of Rosiglitazone. Under basal conditions, rosiglitazone-treated adipocytes had higher OCRs than control adipocytes (4-fold). Further analysis of bioenergetics parameters showed that Rosiglitazone treatment increased proton leak (uncoupling), ATP turnover, maximum respiration (4-fold), reserve capacity and non-mitochondrial respiration, similar to the profile recently reported by Bartesaghi et al., 2015 in human adipose-derived progenitor cells converted into beige cells in the presence of Rosiglitazone (FIG. 7B).

Figure 7C:
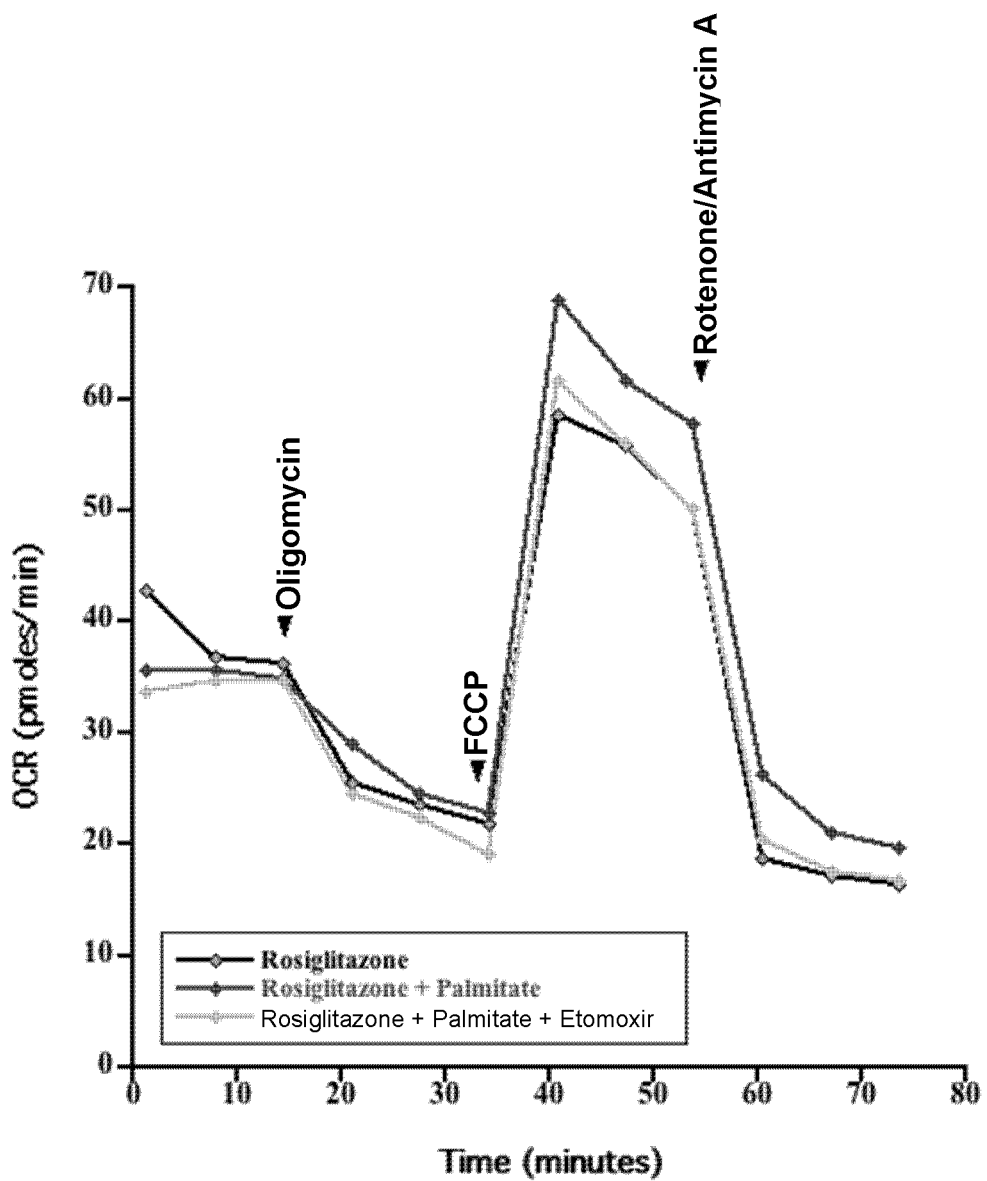
Figure 7D:
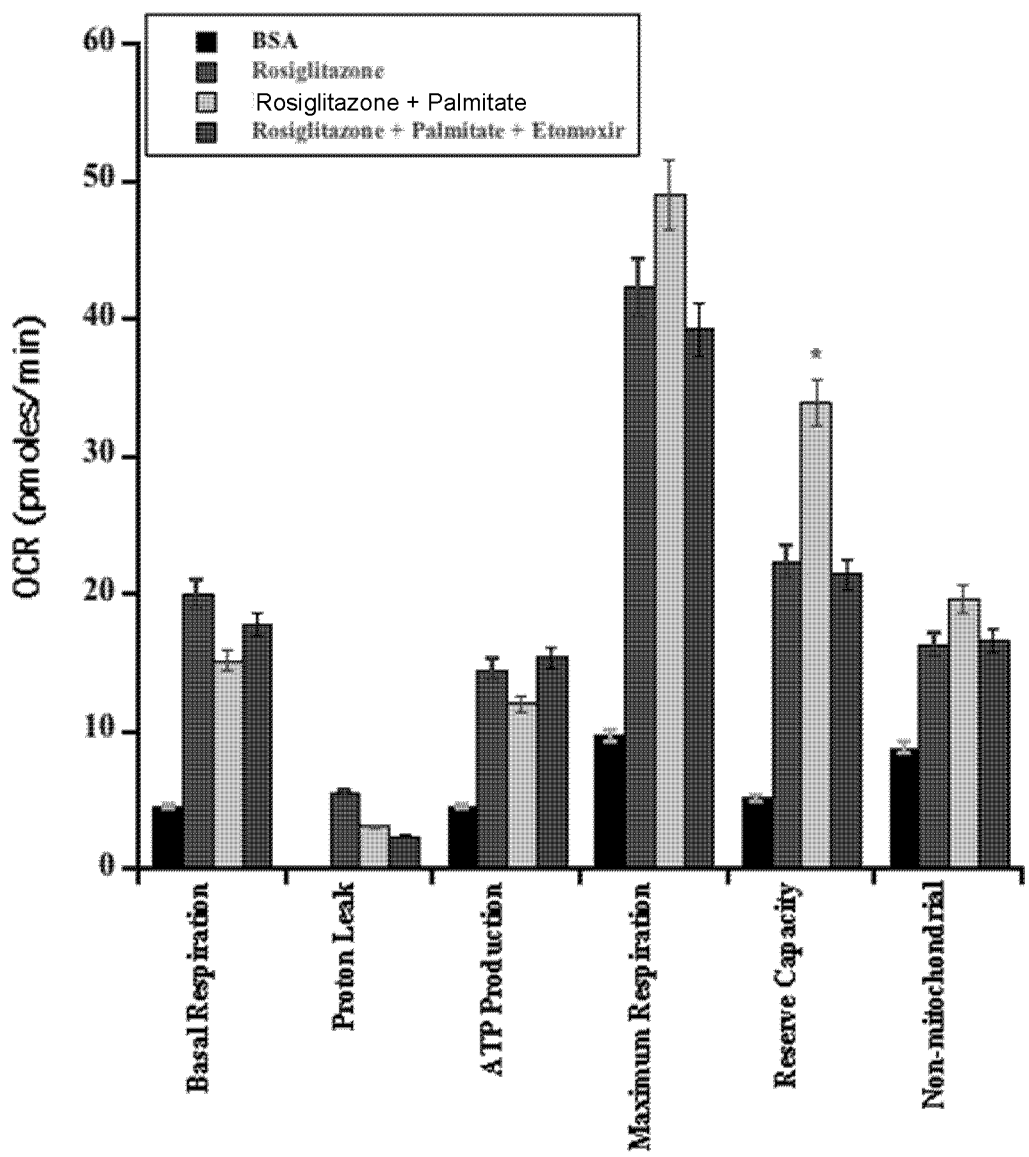
Figure 7E:
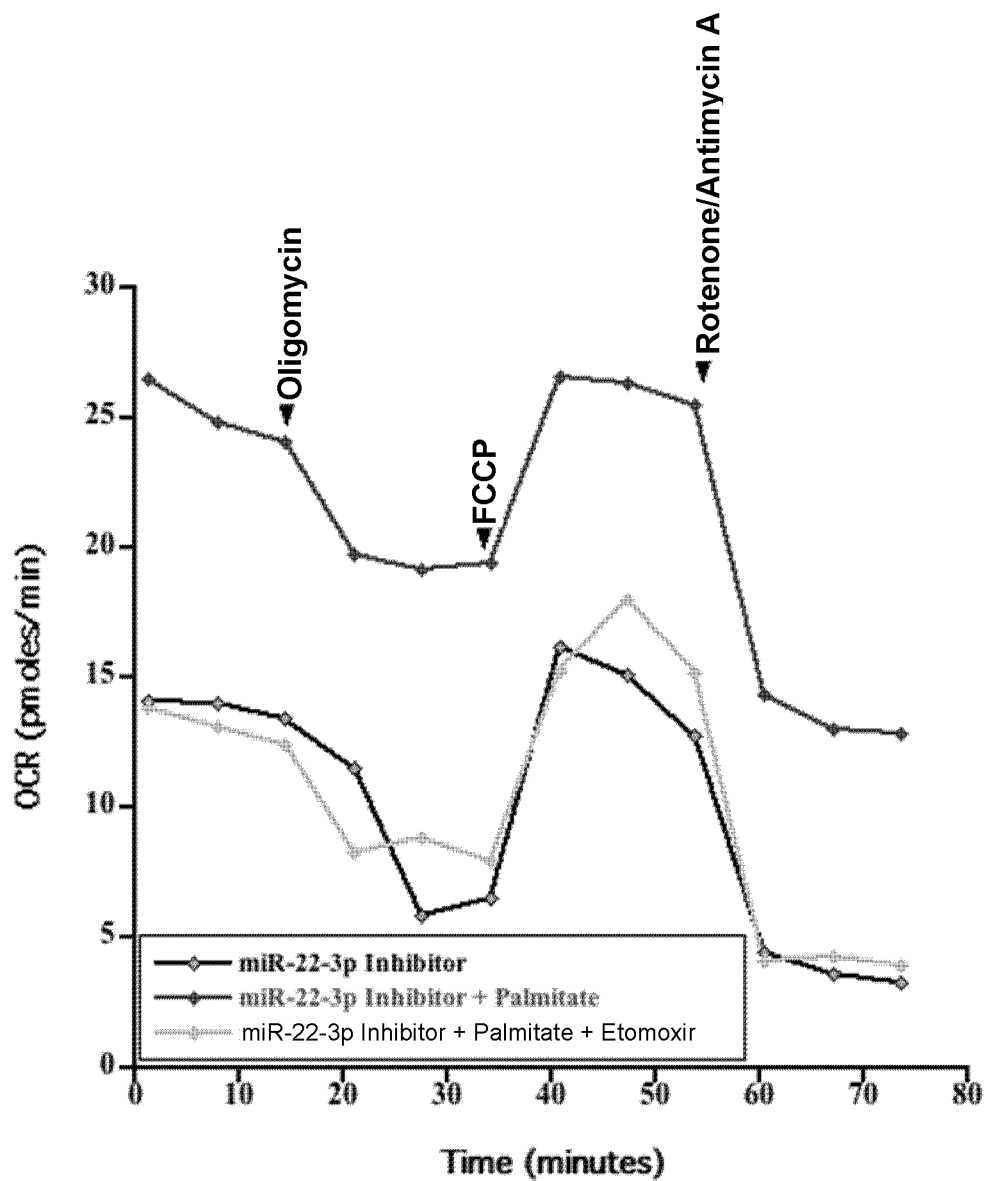
Figure 7F:
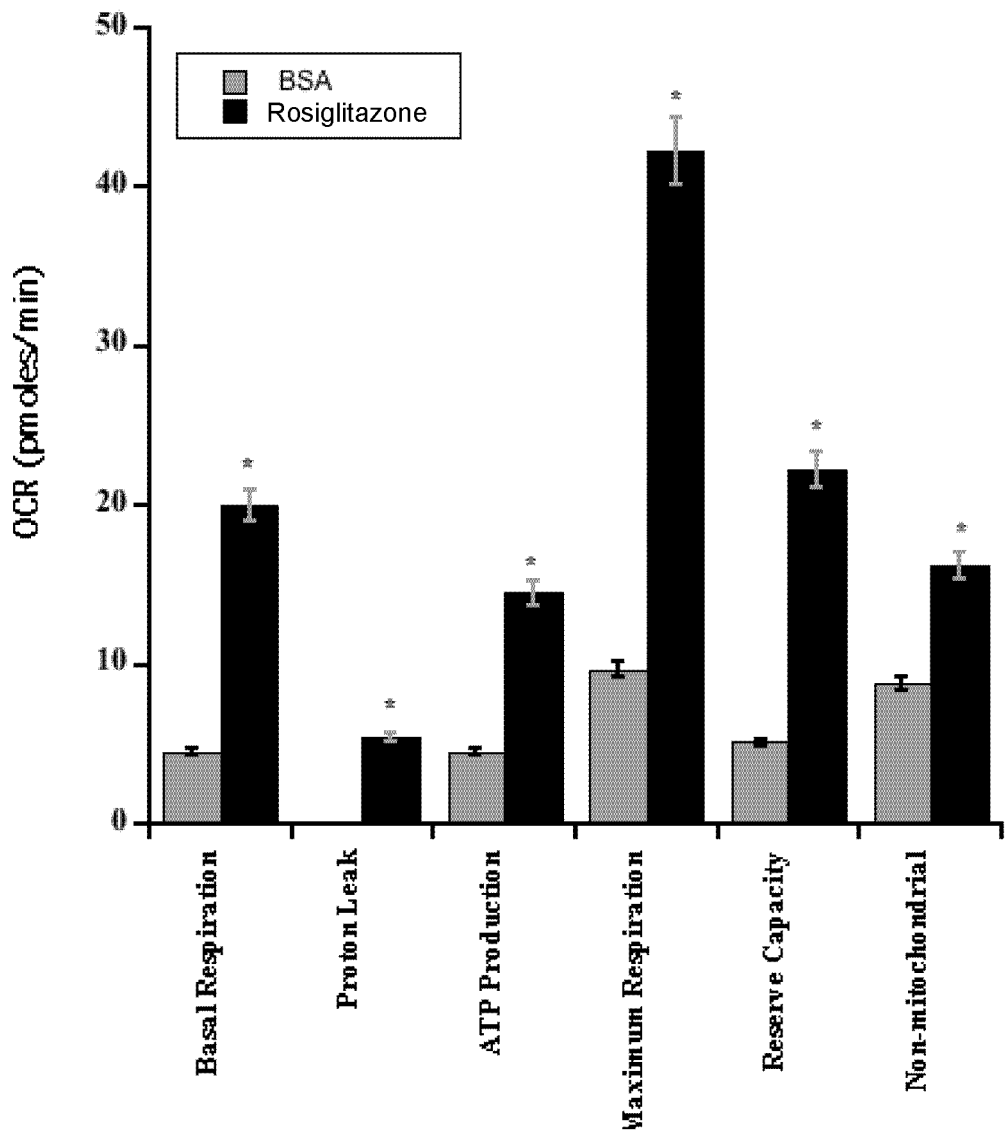

To assess oxidation of endogenous and exogenous fatty acids in the presence of rosiglitazone, Seahorse measurements were performed in the presence of Rosiglitazone alone (utilization of endogenous fatty acids), Rosiglitazone+Palmitate (utilization of exogenous fatty acids) or Rosiglitazone+Palmitate+Etomoxir (blockade of utilization of exogenous fatty acids). FIGS. 7C-7D show that the effects of Rosiglitazone on OCR are mainly due to the utilization of endogenous fatty acids. Under the same conditions, the effects of miR-22-3p inhibition on OCR of human adipocytes in cultures are different (FIGS. 7E-7F). Under basal conditions, miR-22-3 inhibitor-treated adipocytes had higher OCRs than control adipocytes (2-fold) while maximum respiration is increased by 33%. The addition of palmitate to miR-22-3p inhibition induced a dramatic increase of non-mitochondrial respirations as well as proton leak, suggesting that miR-22-3p acts via utilization of both endogenous and exogenous fatty acids, leading to enhanced uncoupling.

1.1.23 Example 10

1.1.24 In Vivo Assessment of Metabolic Responses and Energy Expenditure During 3 Months of Treatment of Adult DIO Mice with a miR-22-3 p Inhibitor A dedicated study was conducted under contract at the University of Buckingham Institute of Translational Medicine (Pr. M A Cawthorne, Pr. P Trayhurn, Dr. C. Stocker) to assess the energetic and metabolic responses to the APT-110 miR-22-3p inhibitor treatment in adult Diet-Inducted-Obese (DIO) C57BL/6 male mice over the course of 3 months. Twenty-four DIO male C57BL/6 mice, who started on 60% high fat diet at the age of 7 weeks, were purchased at 15 weeks of age from the Jackson Laboratory, USA. The mice remained on a 60% high fat diet (Research Diet D12492) throughout the experiment. The mice were kept on a 12 h light/12 h dark light cycle with lights on at 08h00 and at a room temperature of 25±1° C. The mice were allocated to 2 groups of 12 mice each, (2 mice/cage) so that mean and standard deviation for body weight, blood glucose and serum insulin were similar across both groups. Mice were acclimated for two weeks before treatment initiation.

For oral glucose tolerance test, food was removed six hours prior to the start of the glucose tolerance test (09h00) and animals were placed in clean cages. Mice were dosed with glucose at T=0 minutes. Glucose was dissolved in water and given to the mice by oral gavage at a dose of 2.5 g/kg p.o. Blood samples (100) were taken from the cut tip of the tail after the application of Lidocaine gel (Biorex Laboratories UK) for the analysis of glucose concentration at −30, 0, 30, 60, 120 and 180 minutes relative to glucose administration. Blood samples were also taken at −30 and +30 minutes for insulin analysis (Crystal Chem Inc. Cat INS90090). Food was returned to the animals at the end of the glucose tolerance test. Plasma nonesterified Fatty Acids (NEFA, Crystal Wako Chemicals Gmbh, Neuss, Germany, Cat 999-75406), leptin (Crystal Chem. Inc., Cat LEP90030) and adiponectin (Alpco Diagnostics, Salem, New Hampshire, Cat 47-ADPMS-E01) were measured as per the manufacturers' recommendations. Body fat and lean content was measured by Nuclear Magnetic Resonance (NMR). Comparison with calibrated standards allowed identification of types of tissue by their density. Dedicated software was used to quantify amounts of adipose and fat. The mice were gently restrained, sufficient to keep them quiescent during this non-invasive technique.

To measure physical activity, mice were kept in their original cages of 2 mice per cage. Recordings were taken using an infra-red recorder linked to a laptop. Recordings were made on the hour every hour from 7 pm until 8 am. Each recording was of 10-minute duration. Lights went out at 8 pm and came on again at 8 am. Analysis of activity was done by virtually drawing 2 lines across each cage (thus dividing them into 3 equal parts). Recordings were analyzed by eye and the number of times a line was broken by a mouse in each 10-minute segment was scored. Energy expenditure was measured at several time points during the course of the study by open-circuit indirect calorimetry with mice kept in their home cages (6 cages of 2 mice per experimental group (Arch, J. R., et al., 2006; Arch, J. R. and P. Trayhurn, 2013).

At the end of the study, tissues and organs were collected, then frozen for future gene expression analysis or placed in 10% neutral buffered formalin solution (Sigma-Aldrich Cat HT501128), then washed in PBS, pH 7.4 and transferred to 70% ethanol for subsequent processing for histologic and immunohistochemistry analyses.

Figure 8:
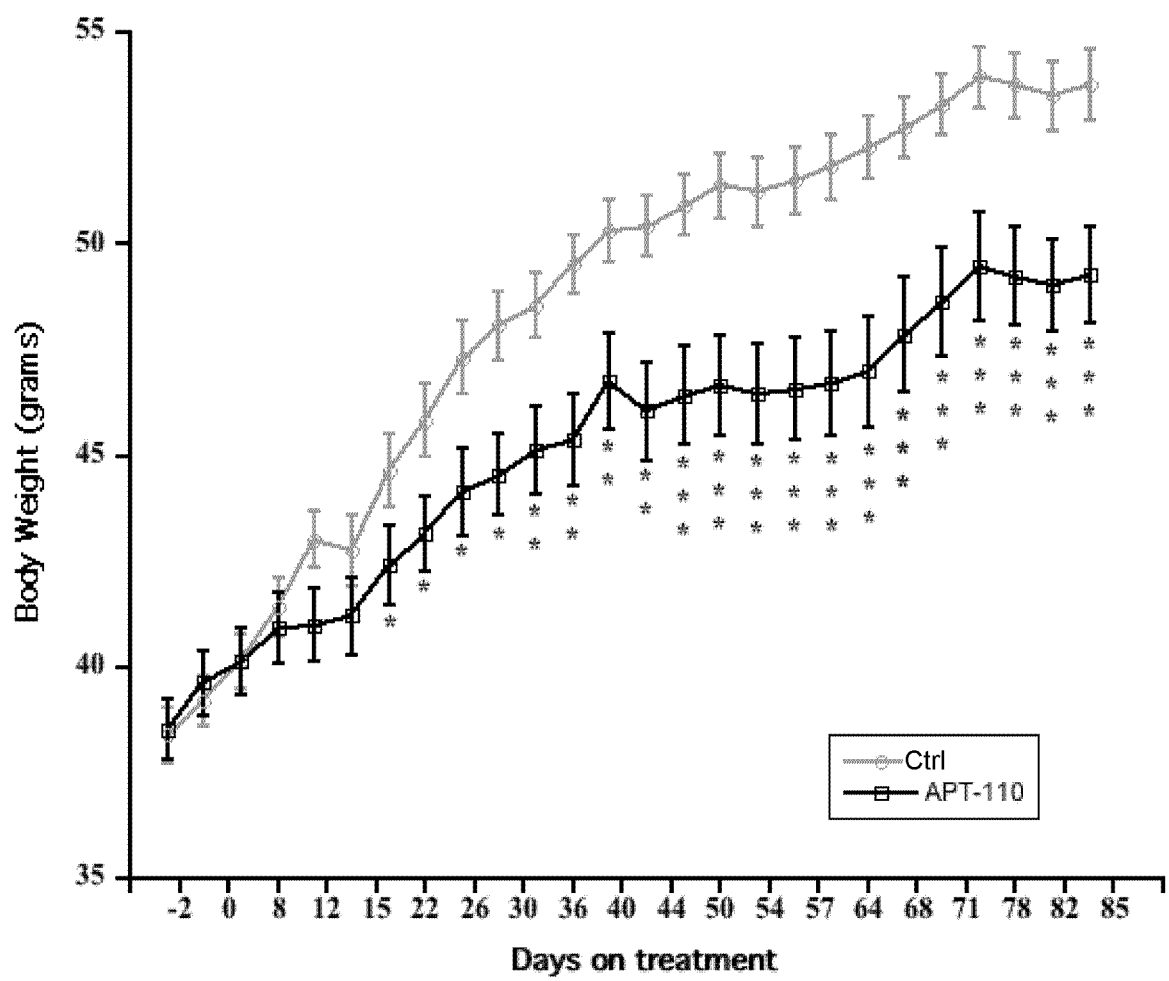
FIG. 8 Body weight profile of C57Bl/J6 adult male mice on 60% high fat diet alone (saline, gray line) or in the presence of the custom-designed APT-110 miR-22-3p inhibitor (black line) during 12 weeks of treatment, beginning at 15 weeks of age.
Figure 9:
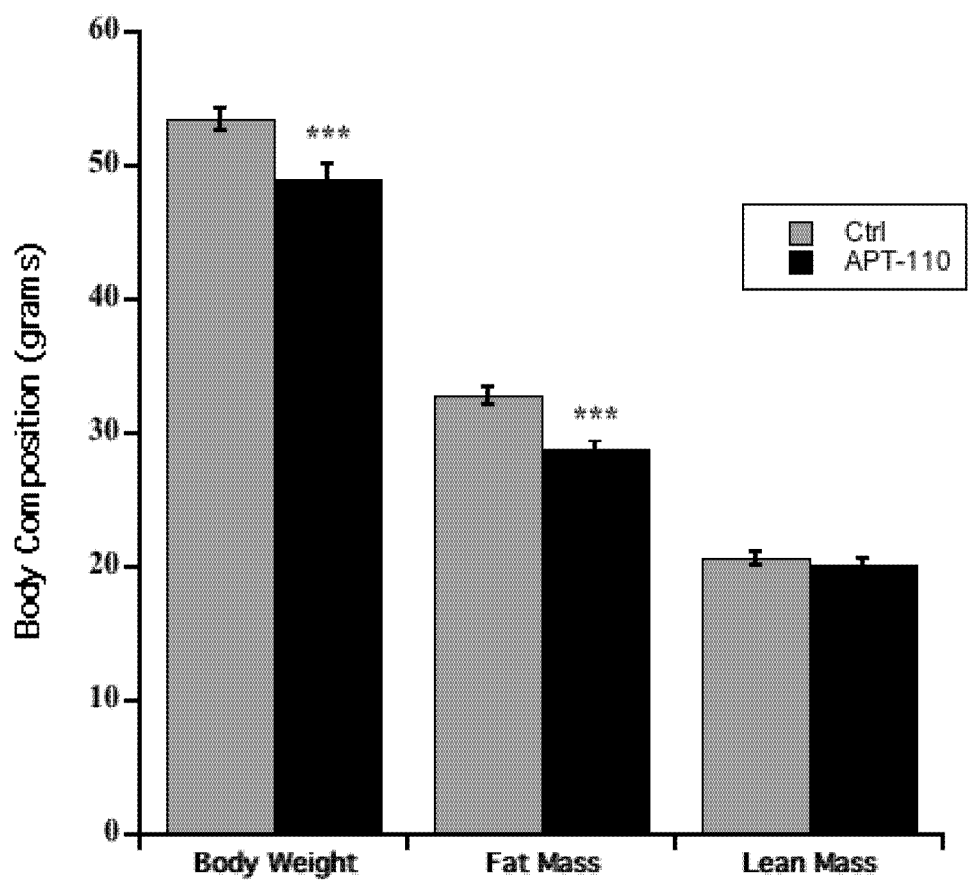
FIG. 9 Body composition by NMR analysis at week 12 (day 82) of C57Bl/J6 adult male mice kept on 60% high fat diet since week 6 and receiving saline injections (gray columns) or the APT-110 miR-22-3p inhibitor (black columns) during 12 weeks of treatment, beginning at 15 weeks of age.

No animal was excluded from this study protocol. At the end of 12 weeks of treatment while on high fat diet (27-week old mice), the mice treated with the APT-110 miR-22-3p inhibitor gained significantly less weight (−30% at week 12 of treatment) than the mice receiving saline injections (FIG. 8). The difference became statistically significant as early as week 3 of treatment. There was no difference in food consumption between the two groups (total consumption of 229±6 grams per cage vs. 223±5 grams per cage). There was no difference in night time physical activity between the two groups (54±8 line breaks per cage vs. 57±8 line breaks per cage). Body composition analysis by NMR at the end of the study (Week 12, Day 82) showed that the body weight difference was due to a fat mass difference only (−12% in the APT-110 group) whereas lean mass was identical in both groups (FIG. 9).

Figure 10A:
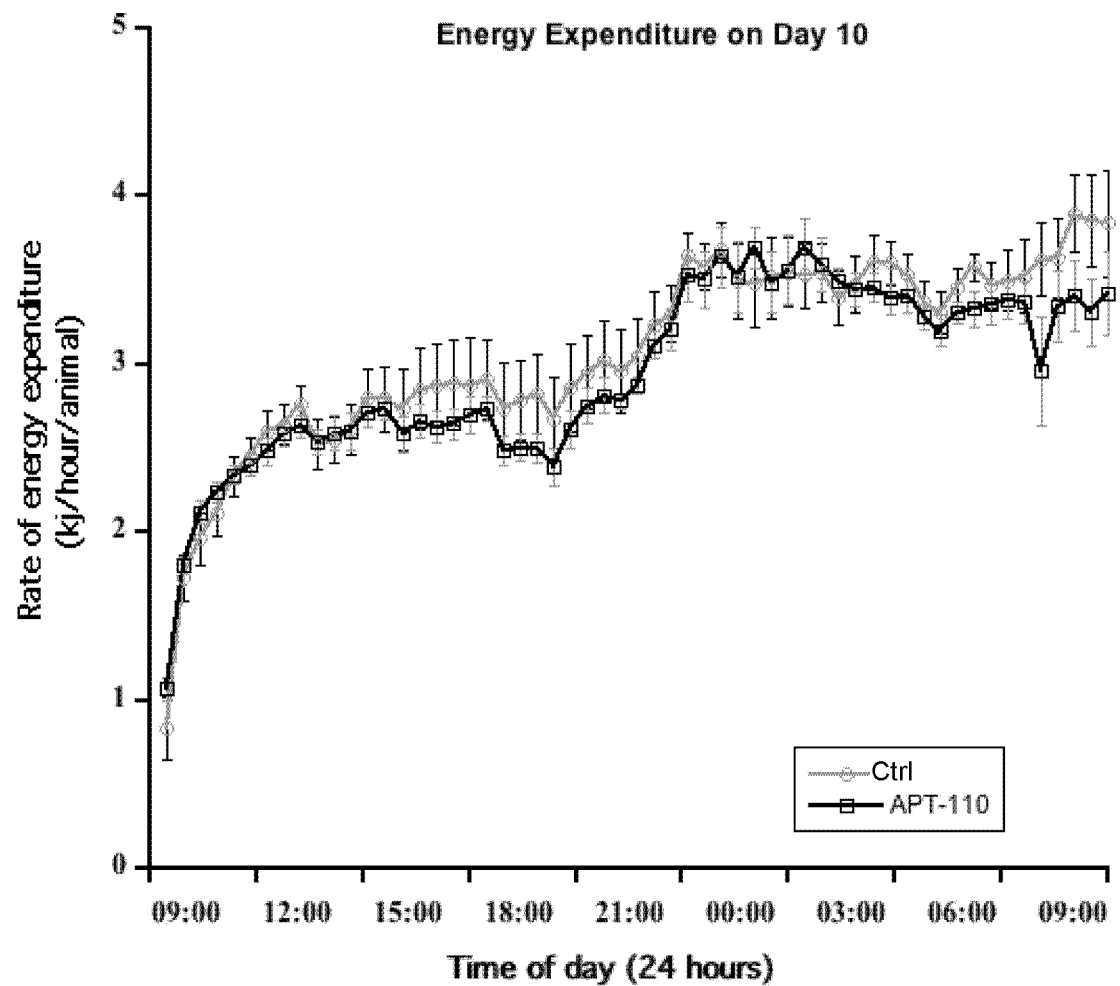
FIGS. 10A-10D Energy expenditure measured over 24 hours at different time points in C57Bl/J6 adult male mice kept on 60% high fat diet since week 6 and receiving saline injections (gray line) or the APT-110 miR-22-3p inhibitor (black line) during 12 weeks of treatment, beginning at 15 weeks of age.
Figure 10B:
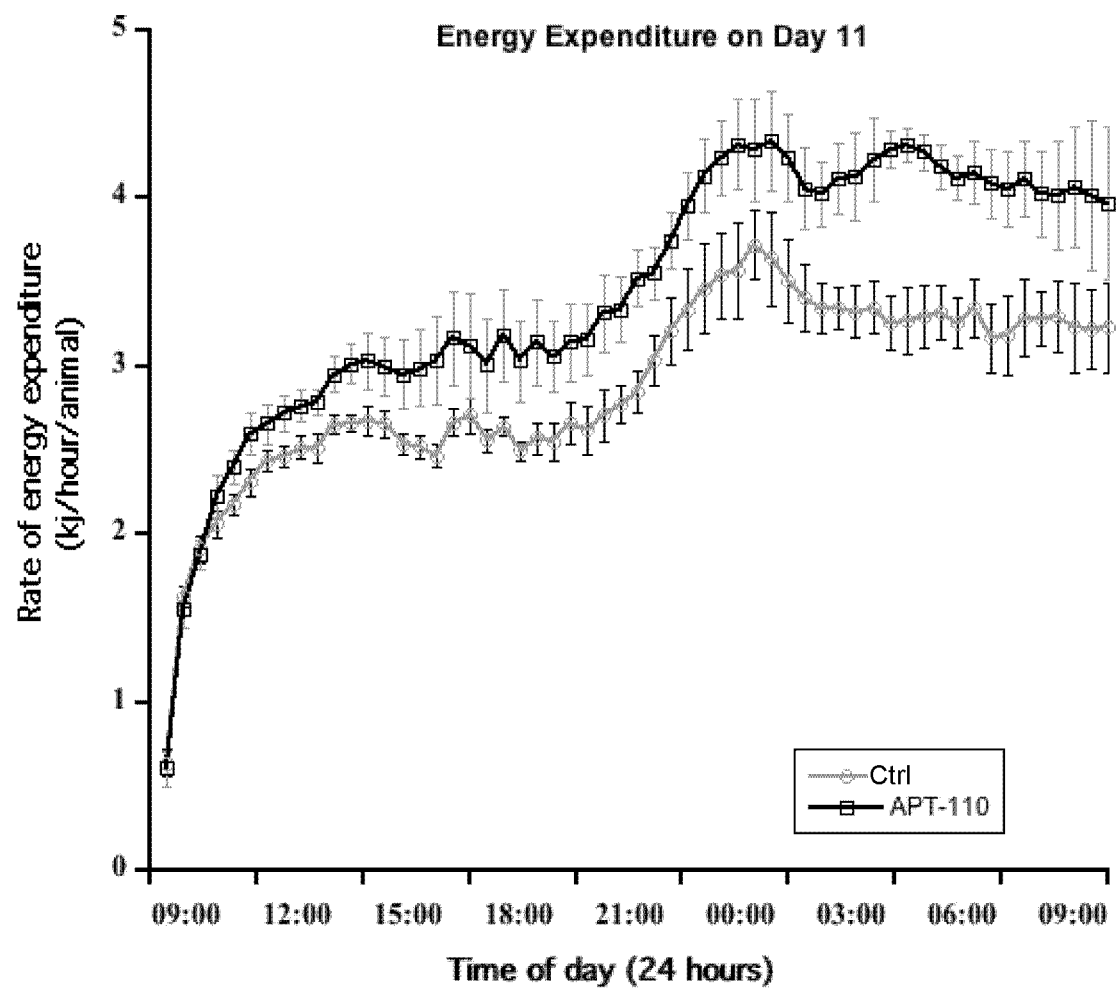
Figure 10C:
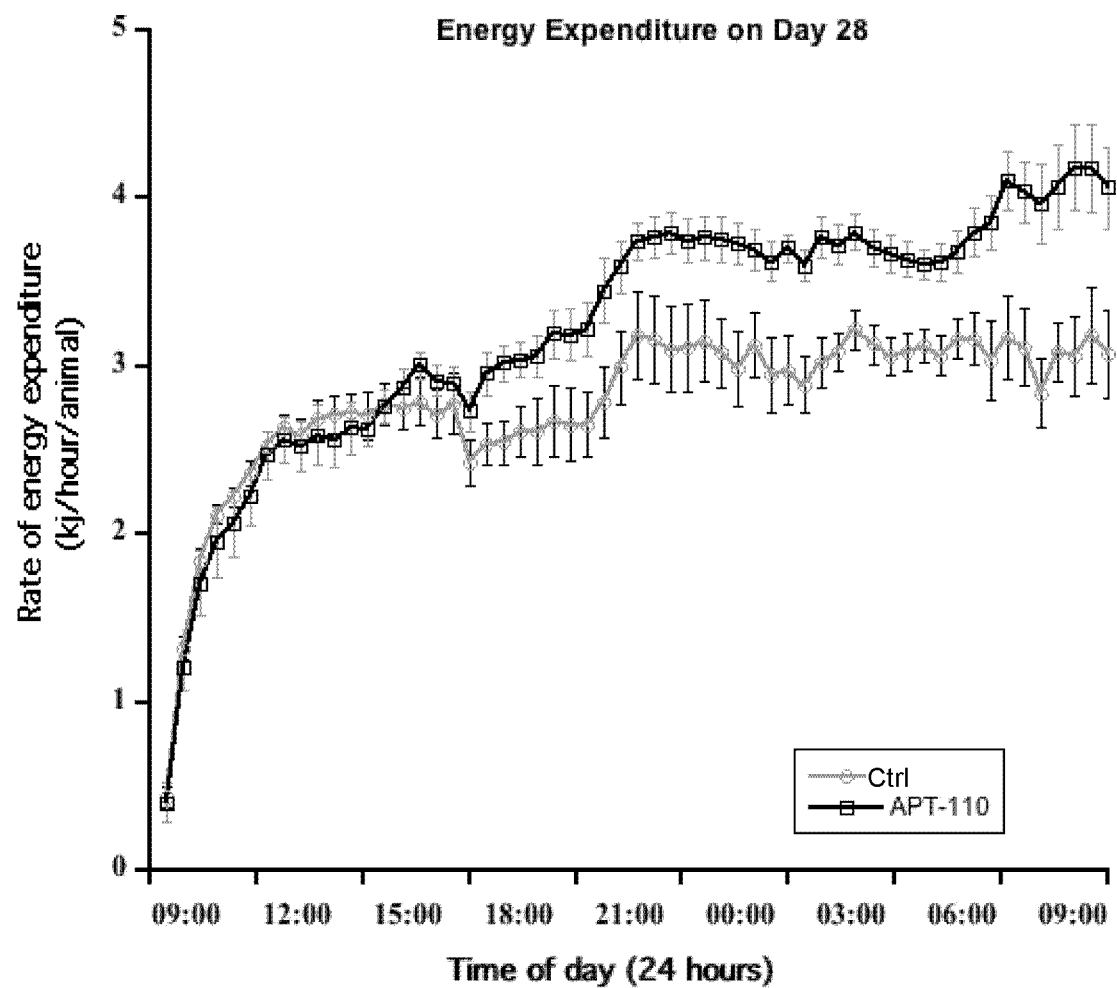
Figure 10D:
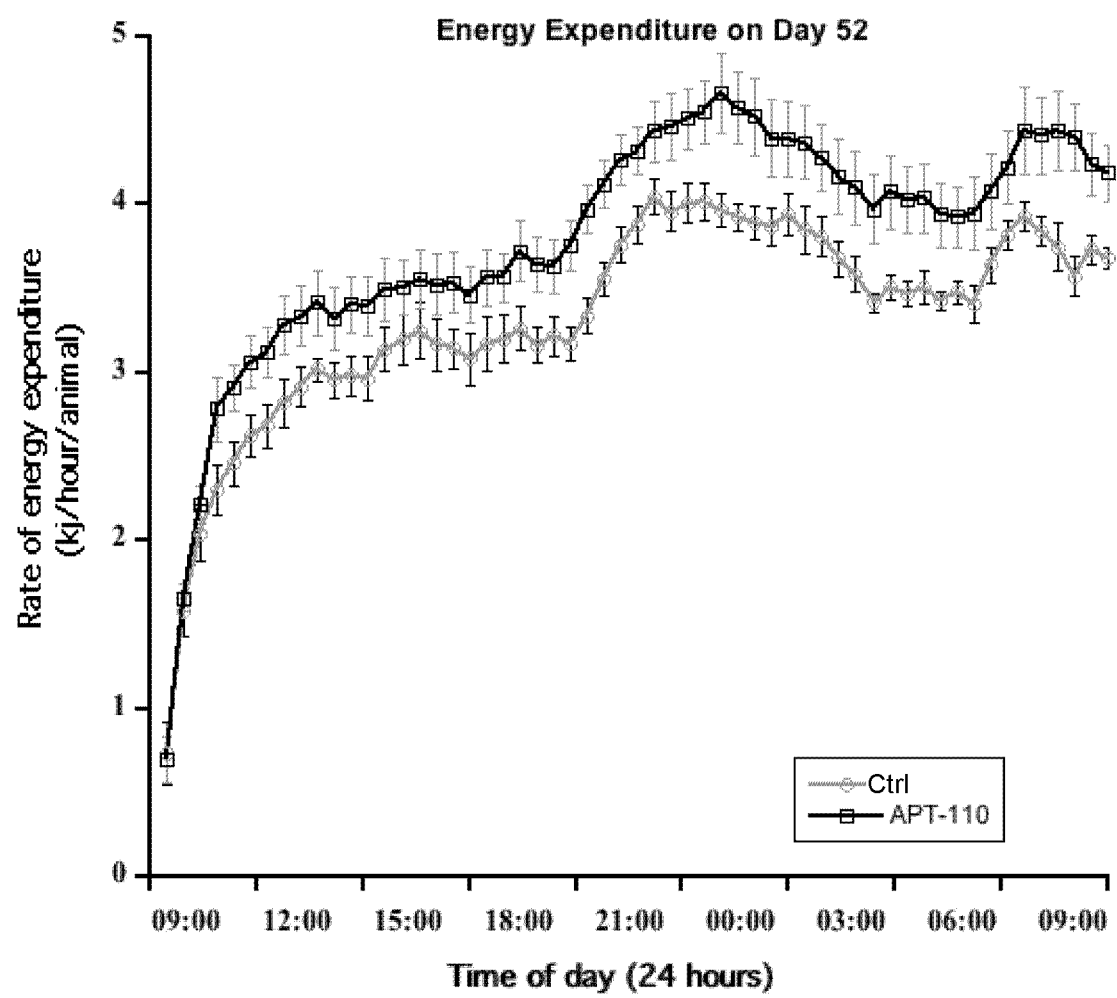
Figure 10E:
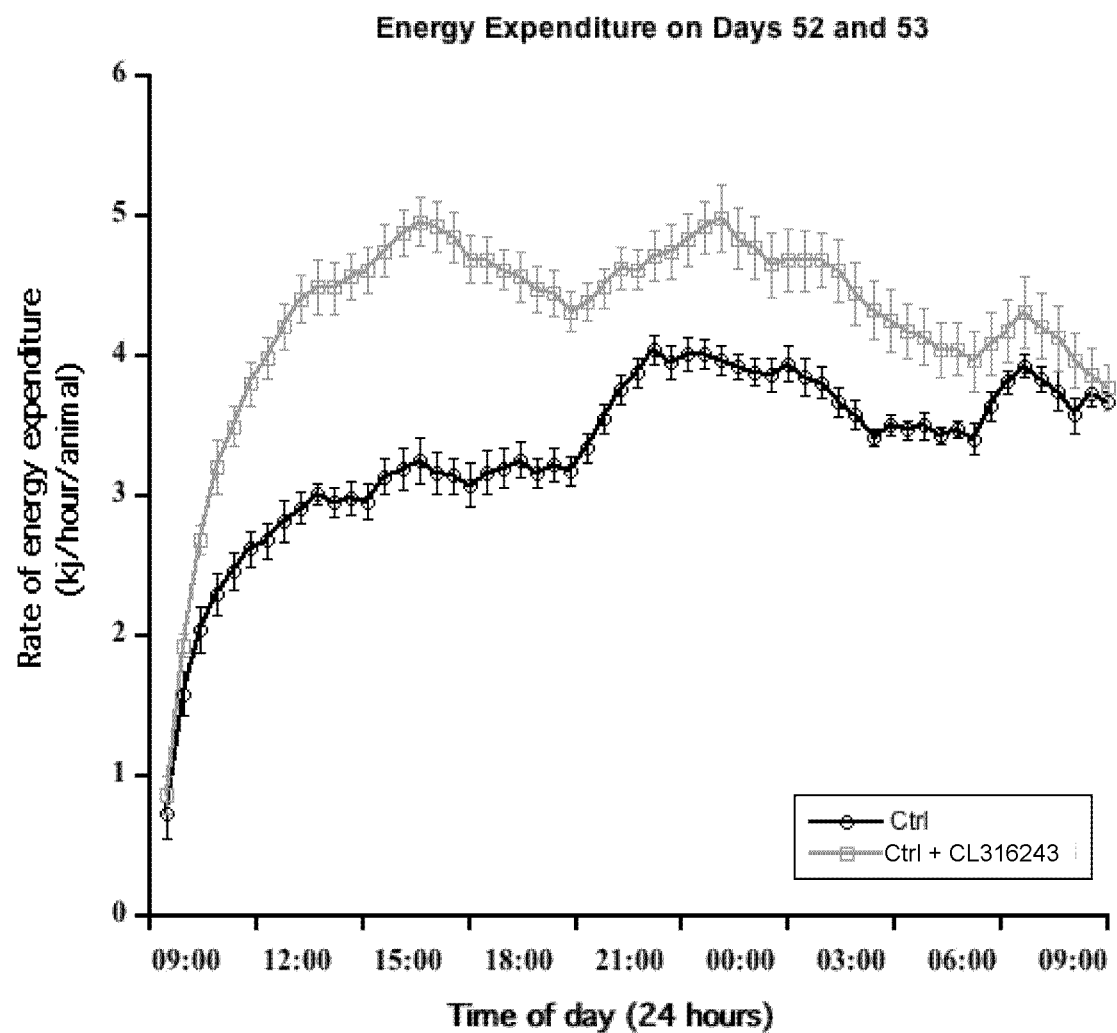
FIG. 10E Energy expenditure measured on days 52 and 53 in C57Bl/J6 adult male mice kept on 60% high fat diet since week 6 and receiving saline injections (gray columns) or the CL316243 β-adrenoceptor agonist (black columns) during 12 weeks of treatment, beginning at 15 weeks of age.
Figure 10F:
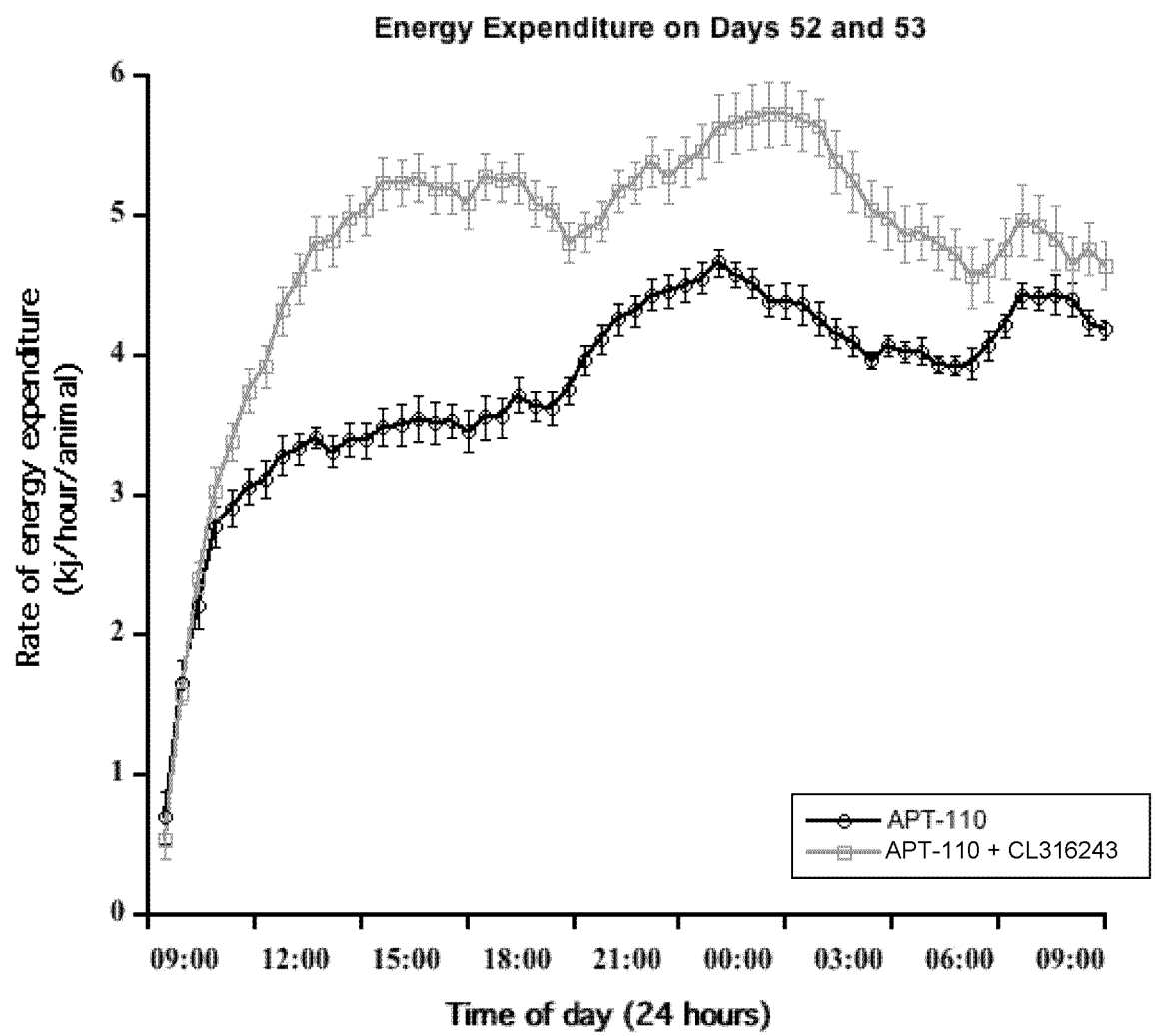
FIG. 10F Energy expenditure measured on days 52 and 53 in C57Bl/J6 adult male mice kept on 60% high fat diet since week 6 and receiving APT-110 miR-22-3p inhibitor (black line) or the CL316243+APT-110 (gray line) during 12 weeks of treatment, beginning at 15 weeks of age.
Figure 11:
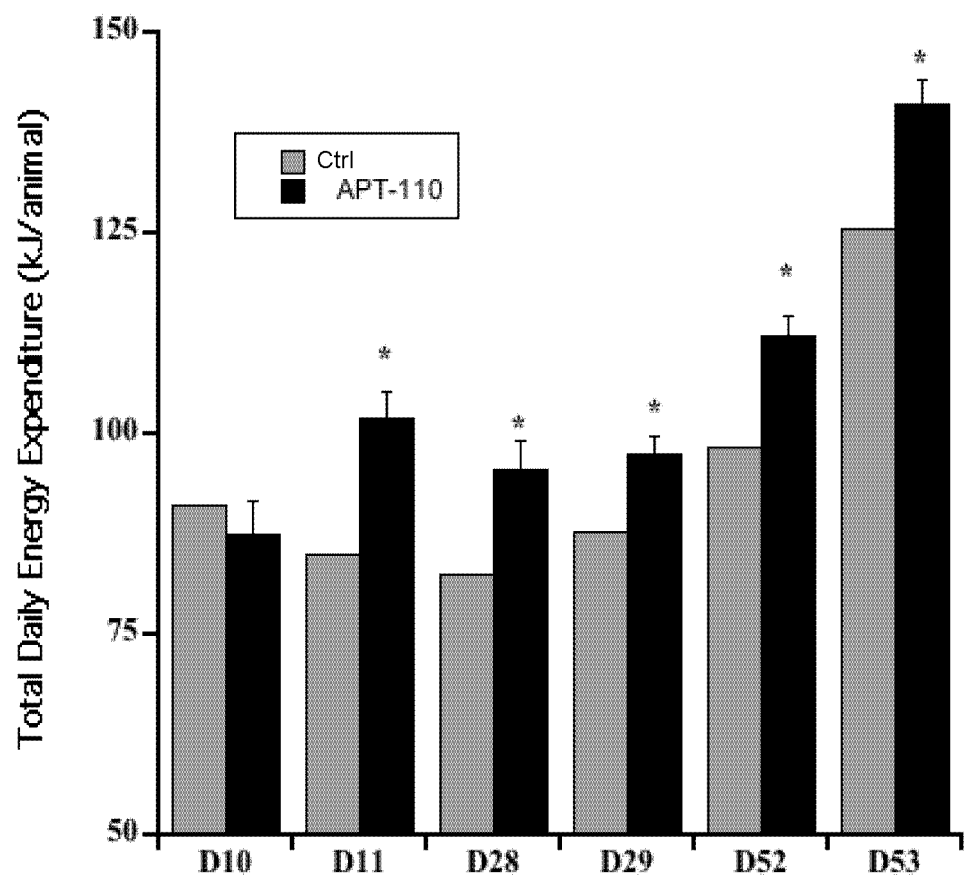
FIG. 11 Total energy expenditure measured over 24 hours at different time points in C57Bl/J6 adult male mice kept on 60% high fat diet since week 6 and receiving saline injections (gray columns) or the APT-110 miR-22-3p inhibitor (black columns) during 12 weeks of treatment, starting at week 15 of age. Measurement on Day 53 were made in the presence of CL316243 β-adrenoceptor agonist.
Figure 12:
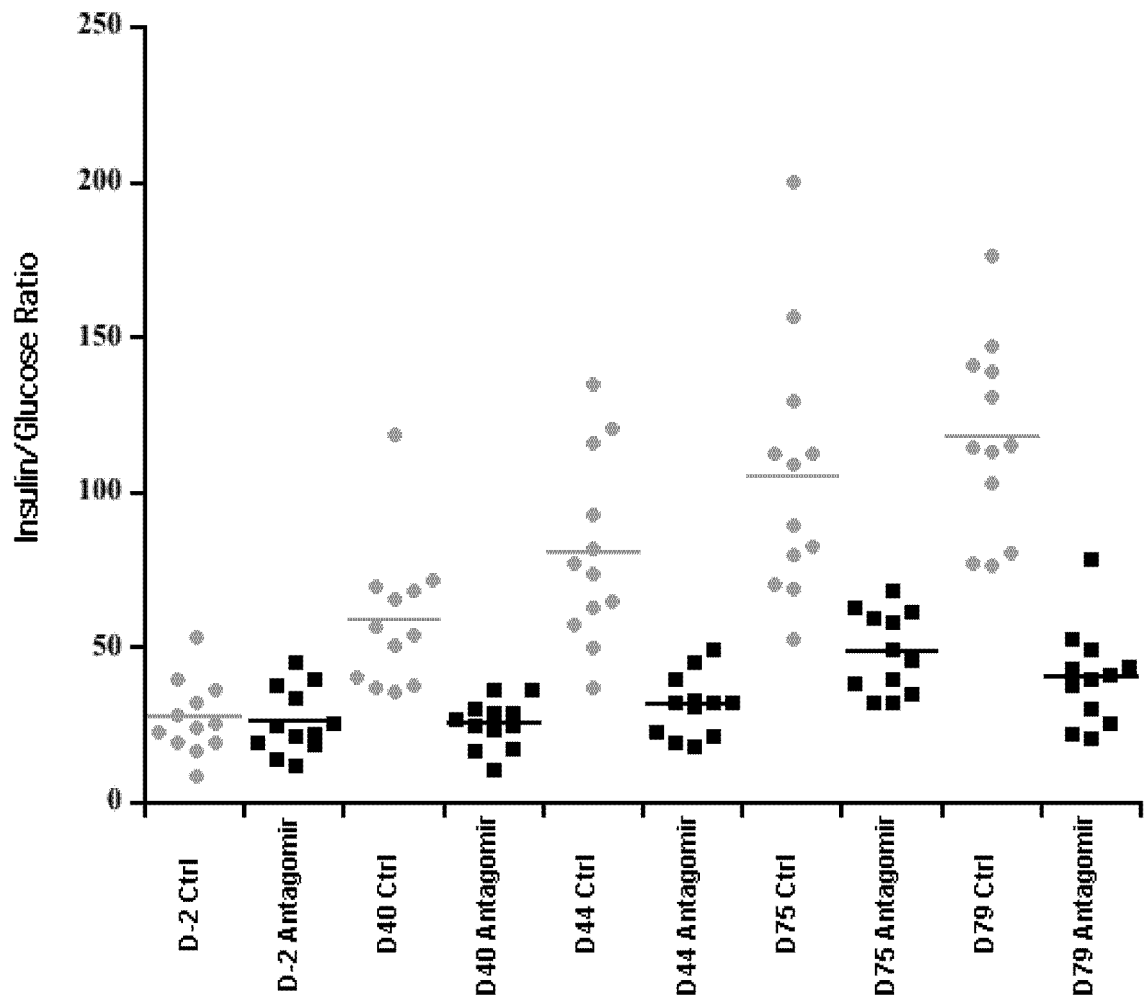
FIG. 12 Fasting Insulin/Glucose ratio in C57Bl/J6 adult male mice kept on 60% high fat diet since week 6 and receiving saline injections (gray circles) or the APT-110 miR-22-3p inhibitor (black squares) during 12 weeks of treatment, beginning at 15 weeks of age.

The first 24-hr energy expenditure recording performed at Day 10 of treatment did not show a difference between the saline and APT-110 groups (FIG. 10A). However, an increase in energy expenditure was observed in the group treated with APT-110 as early as Day 11 (FIG. 10B) and confirmed on Day 28 (FIG. 10C) and Day 52 (FIG. 10D). Furthermore, after i.p. injection of 0.5 mg/kg of the beta3 receptor agonist CL316243, energy expenditure was increased not only in the control group (FIG. 10E) but also in the APT-110 group (FIG. 10F), thus suggesting that miR-22-3p inhibition acts in synergy with activation of the beta3 adrenergic system. The total daily energy expenditure observed from day 11 to day 53 was on average 13% greater on APT-110 treatment (FIG. 12).

Blood glucose, plasma insulin, leptin and adiponectin were measured after fasting the mice for 6 hours on Days −2, 44 and 79 of treatment. As shown in Table 8, blood glucose, plasma insulin and leptin levels were significantly lower on APT-110 treatment, whereas plasma adiponectin levels were similar across both groups.

TABLE 8

Circulating Metabolic Parameters

| | Group | Blood glucose (mmol/L) | Plasma insulin (pmol/L) | Plasma leptin (nmol/L) | Plasma adiponectin (ng/mL) |
|---|---|---|---|---|---|
| Day −2 | Ctrl | 6.65 ± 0.21 | 172 ± 21 | 3.27 ± 0.31 | 3.20 ± 0.15 |
| | APT-110 | 6.69 ± 0.27 | 179 ± 18 | 3.11 ± 0.45 | 3.16 ± 0.13 |
| Day 44 | Ctrl | 10.94 ± 0.34 | 837 ± 91 | 8.23 ± 0.62 | 3.04 ± 0.13 |
| | APT-110 | 9.01 ± 0.19 * | 295 ± 25 * | 4.85 ± 0.42 * | 2.66 ± 0.15 |
| Day 79 | Ctrl | 7.31 ± 0.20 | 843 ± 47 | 7.81 ± 1.09 | 3.82 ± 0.24 |
| | APT-110 | 5.71 ± 0.18 * | 220 ± 17 * | 4.21 ± 0.54 * | 3.16 ± 0.13 |

* = <0.0001 vs control group at the same time point

Figure 13:
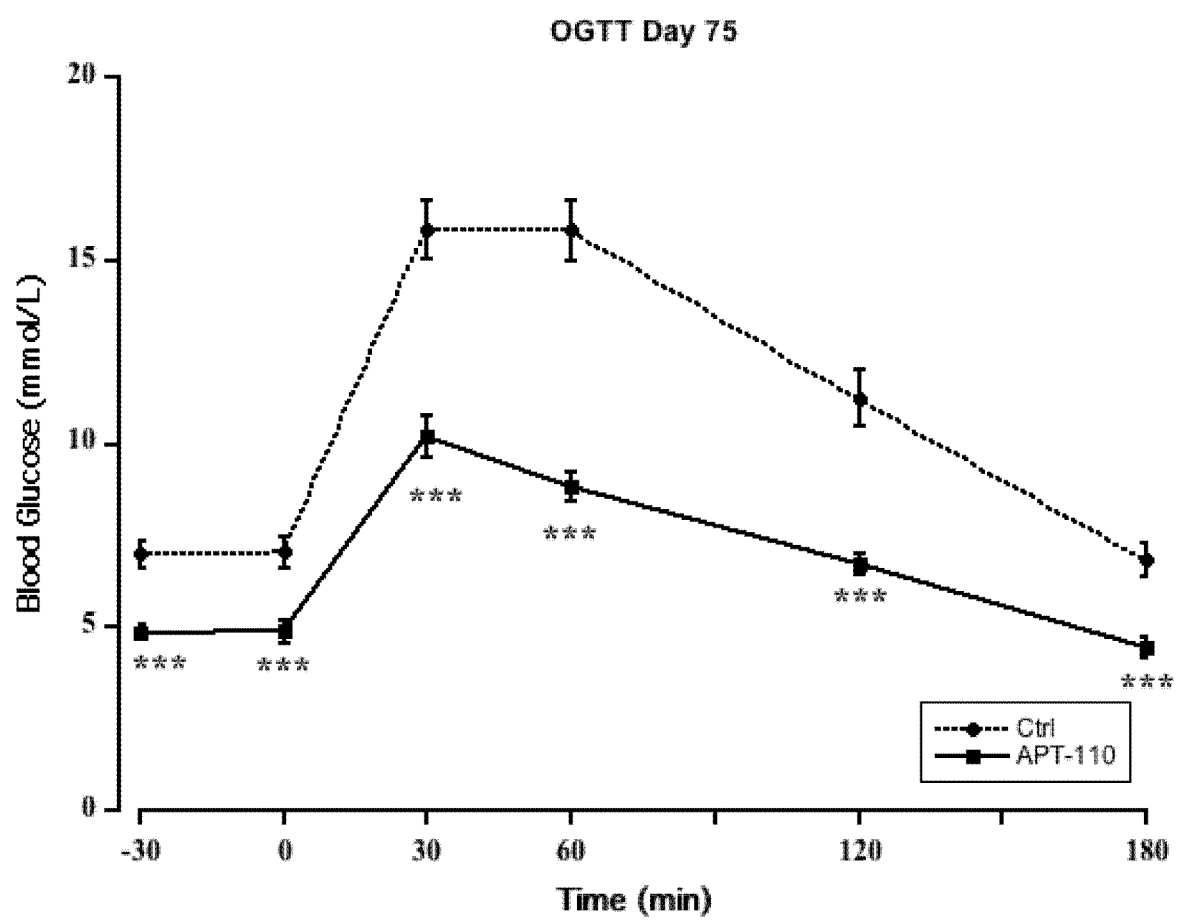
FIG. 13 Oral Glucose Tolerance Test during the last week of treatment in C57Bl/J56 adult male mice kept on 60% high fat diet since week 6 and receiving saline injections (dotted line) or the APT-110 miR-22-3p inhibitor (solid line) during 12 weeks of treatment, beginning at 15 weeks of age.
Figure 14:
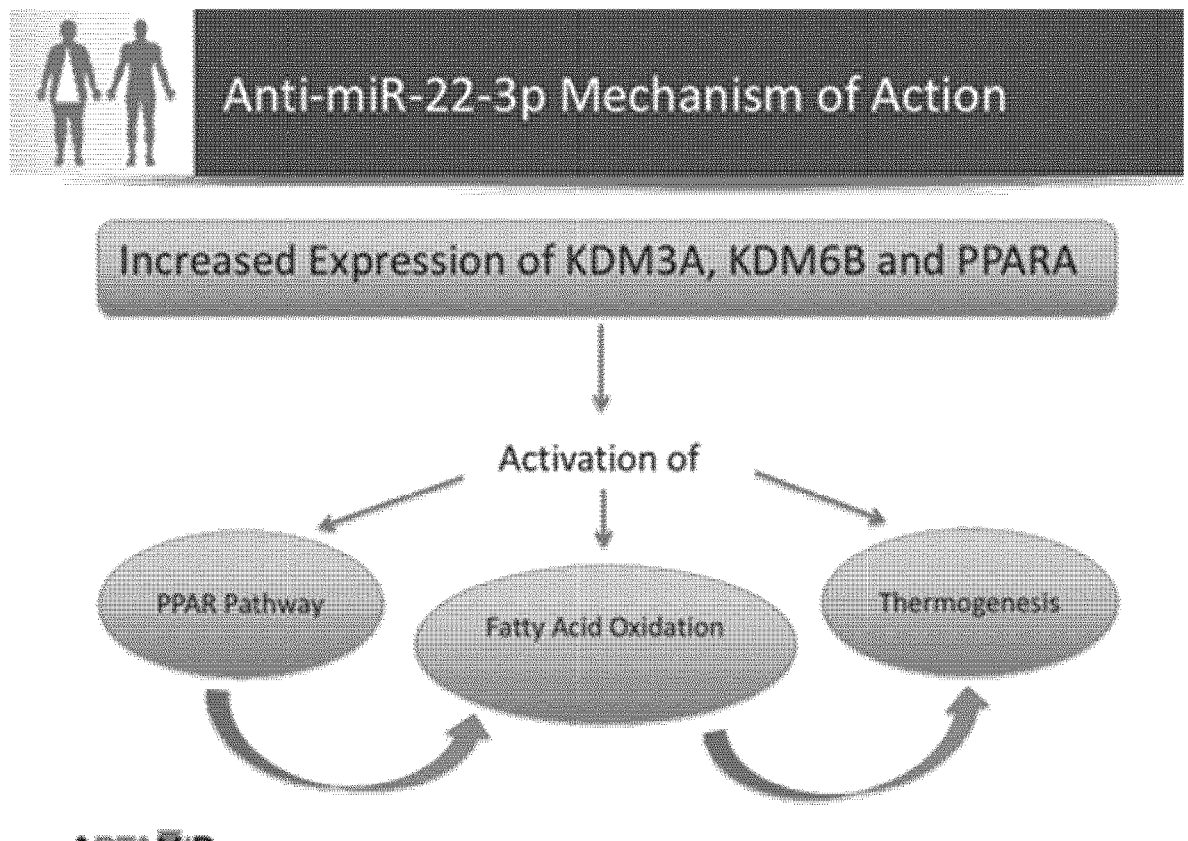
FIG. 14 Proposed mechanisms of action and downstream effects of miR-22-3p inhibitor.
Figure 15:
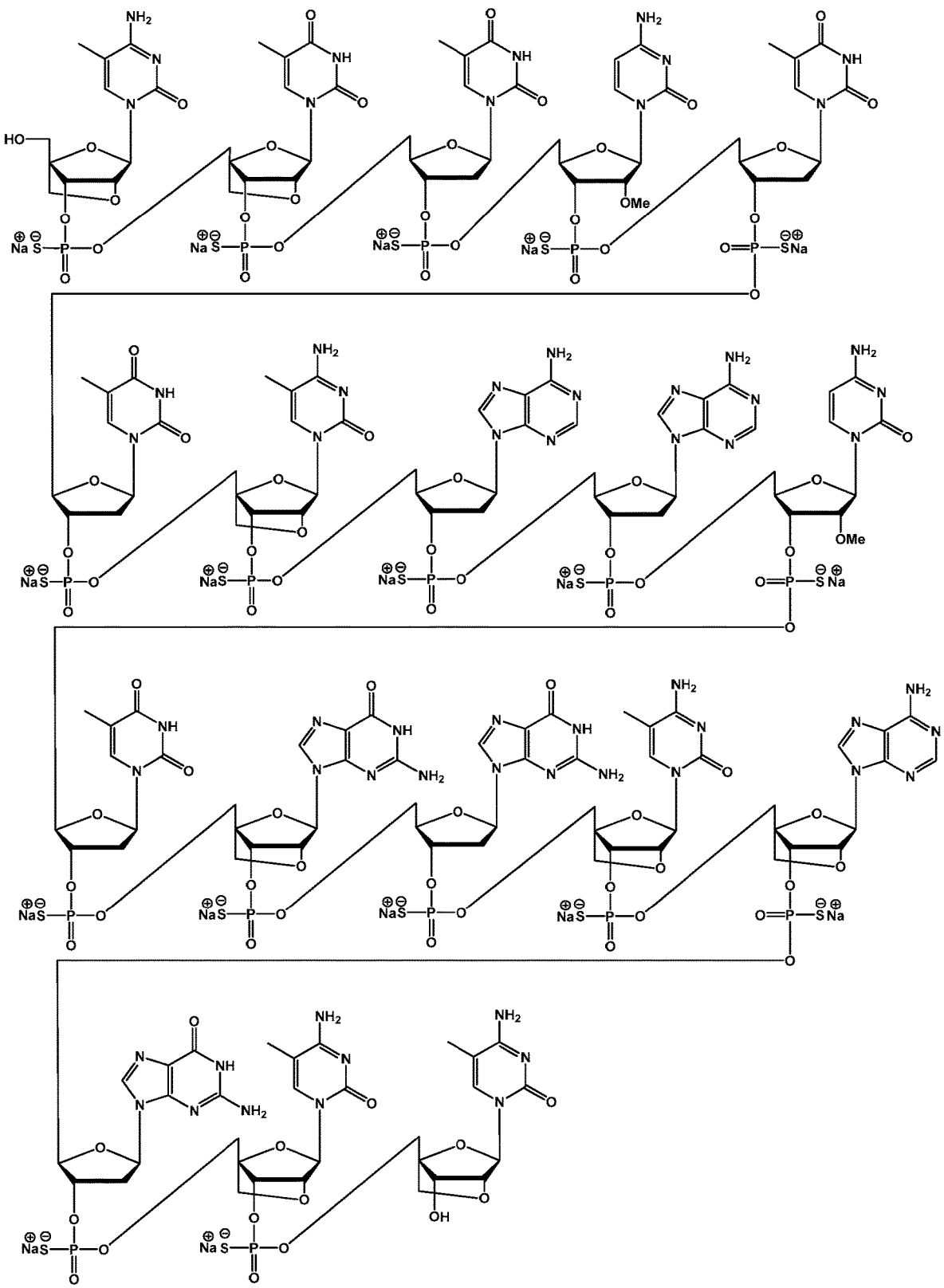
FIG. 15 Chemical structure of (SEQ ID NO: 18).
Figure 16:
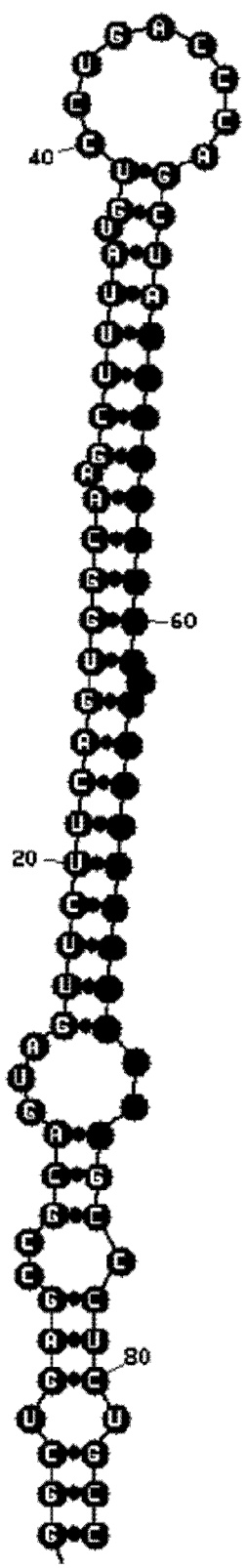
FIG. 16 Stem-loop structure of hsa-mir-22 (SEQ ID NO:11).

Calculation of the fasting Insulin/Glucose ratio at different time points during the course of the study illustrates the development of insulin resistance over time in the control group on 60% fat diet, whereas the group treated with the APT-110 mir-22-3p inhibitor maintain the same level of insulin sensitivity (FIG. 13).

Oral Glucose Tolerance Tests were performed at Day 75 during the last week of 12-week treatment. Mice receiving the saline injections displayed a diabetic profile, whereas the mice receiving the APT-110 miR-22-3p inhibitor had a normal profile.

Circulating lipid profile was measured on Day 85 at the end of the last week of treatment after a 6-hour fast. The group on the APT-110 miR-22-3p inhibitor displayed reduced cholesterol and increased NEFA levels. These changes support the increased metabolic rate in the APT-110 treated mice, an increased lipolytic rate leading to the increase in the release of fatty acids into the blood, so increasing beta oxidation.

TABLE 9

Circulating Lipid Profile

| | Group | Cholesterol (mmol/L) | Non Esterified Fatty Acids (mmol/L) | Triglycerides (mmol/L) |
|---|---|---|---|---|
| Day 85 | Ctrl | 5.93 ± 0.14 | 1.38 ± 0.06 | 1.28 ± 0.08 |
| | APT-110 | 4.67 ± 0.16 | 1.71 ± 0.08 | 1.46 ± 0.08 |
| p value | | <0.0001 | =0.003 | =0.11 |

TABLE 10

Anatomy Analysis Results

| Tissue/organ (grams, Mean ± SEM) | Ctrl | APT-110 |
|---|---|---|
| Heart | 0.194 ± 0.014 | 0.179 ± 0.008 |
| Liver | 3.057 ± 0.114 | 2.442 ± 0.127 * |
| Spleen | 0.117 ± 0.007 | 0.115 ± 0.005 |
| Inguinal fat | 4.087 ± 0.250 | 3.166 ± 0.135 * |
| Epdidymal fat | 2.722 ± 0.126 | 1.8 ± 0.978 * |
| Peri-renal fat | 1.596 ± 0.155 | 1.183 ± 0.096 * |
| Subscapular fat | 0.564 ± 0.022 | 0.202 ± 0.020 * |

As in the previous studies, miR-22-3p inhibition treatment induced a significant size reduction of various adipose tissues. In addition, liver size was also reduced during miR-22-3p inhibition treatment.

1.1.25 Example 11

1.1.26 APT-110 Description and Physicochemical Characteristics

APT-110 is the 17-sodium salt of an oligonucleotide 18 bases in length. All 17 internucleotide linkages are phosphorothioates. The sequence also includes a number of chemically modified nucleotides, including locked nucleic acids (LNA), 2'-OCH3 substitutions, and 5-methyl-cytidine. The sequence contains no ribose. The sequence is shown below: 5'-5mCpsTpsTps2'OMeCpsTpsTps5mCpsAps Aps2'OMeCpsTpsGpsGps5mCpsApsGps5mCpsT-3' (SEQ ID NO: 4)

In the scheme above, 5m designates the 5-methyl substitution on cytosine, 2'OMe designates the 2' OCH3 substitution, and bold underline designates locked nucleic acids. The 2' OCH3 cytidines are not methylated at the 5 position. If no modification is indicated, the nucleotide contains deoxyribose. The distribution of nucleotides in the sequence is shown in Table 11.

TABLE 11

Distribution of Nucleotides in APT-110

| Nucleotide | Frequency |
|---|---|
| dA | 2 |
| LNA A | 1 |
| 2'-OCH3-C | 2 |
| LNA 5-methyl-C | 4 |
| dG | 2 |
| LNA G | 1 |
| dT | 4 |
| LNA T | 2 |

The formula weight of the 17-sodium salt is 6412.57 g/mol. The average molecular weight of the acid form of the molecule is 6038.88 amu, and the monoisotopic mass of the acid form of the molecule is 6034.58 amu. Other physicochemical properties of APT-110 are included in Table 12.

TABLE 12

Physicochemical Characteristics of APT-110

| | |
|---|---|
| Molecular Formula | $C_{188}H_{218}N_{60}Na_{17}O_{102}P_{17}S_{17}$ |
| Formula Weight of Sodium Salt | 6412.57 g/mol |
| Molecular Weight of Free Acid | 6038.88 amu |
| Monoisotopic Mass of Free Acid | 6034.58 amu |
| pKa | The pKa values of APT-110 have not been determined. However, the internucleotide linkages, heterocyclic bases and 5'- and 3'-hydroxy functionalities are each expected to have distinct pKa values. The pKa of a dinucleotide phosphorothioate diester is expected to be close to that of a dinucleotide phosphate (pKa = 0.7). The conjugate acids of adenosine and cytidine have pKa values of 3.52 and 4.17, respectively. The pKa values of thymidine and guanosine are 9.93 and 9.42 (Saenger, W., Principles of Nucleic Acid Structure, Springer-Verlag, New York, 1989: Chapter 5, p.108). The 5' and 3'-hydroxy groups of nucleosides have pKa values of around 16. As the charge density on a single molecule is increased, however, pKa values different from those of the isolated nucleosides and dinucleotide phosphates would be expected. |
| Hygroscopicity | Differential vapor sorption studies have not yet been conducted for APT-110. However, based on ample precedent with closely related molecules, the molecules are expected to be hygroscopic, gaining or losing water rapidly depending on the environment to which the molecules are exposed. |
| pH of Solution | The pH of aqueous solution should be near 7 since the molecule has no pKa values near neutral pH. |
| Solubility | The solubility of the molecules has not yet been determined. Based on ample precedent with closely related molecules, the molecules are expected to be freely soluble in water and in aqueous buffer (pH 3.5 or above), soluble or slightly soluble in methanol, and insoluble in acetone, ethanol, acetonitrile, isopropyl alcohol, and chloroform. |

1.1.27 Example 12

1.1.28 APT-110 Structure, Characterization, and Synthesis

Molecular Weight: The mass of APT-110 was determined on a Sciex API 5000 triple quadrupole mass spectrometer operating in negative ion mode with electrospray ionization. Q1 ions were detected with charges of −10 to −5. These ions gave an average mass of 6041.98 for APT-110, within 0.05% of the calculated mass of 6038.88.

Synthetic Procedure: Familiar and well-established amidite chemistry is used to synthesize APT-110. The manufacture of the sequence is a multi-step process that may be divided into two distinct operations: solid-phase synthesis and downstream processing. In the first operation, the nucleotide sequence is assembled by a computer-controlled solid-phase synthesizer. Subsequent downstream processing includes deprotection steps, preparative high pH ion-pair chromatographic purification, isolation of purified material, and lyophilization to yield drug substance.

During the chemical synthesis, amidite monomers are sequentially coupled to an elongating oligonucleotide that is covalently bound to a solid support. Each elongation cycle consists of the following four steps:

1. Detritylation (removal of the 5'-hydroxyl protecting group with acid)
2. Coupling (attachment of an activated amidite to the support-bound oligonucleotide) at the 5'-hydroxyl
3. Sulfurization (conversion of the newly formed phosphite triester to its phosphorothioate triester with a sulfurizing reagent)
4. Capping (acetylation of unreacted 5'-hydroxyls) to prevent any unreacted deprotected sites from reacting in the next cycle UnyLinker is the designated solid support for this synthesis. It is provided ready to accept linkage to the 3'-terminal nucleotide, locked T in this case. The elongation steps outlined above are repeated the appropriate number of times until the entire sequence is built. The final cycle establishes the 5'-terminal 5-mCps nucleotide, and yields the 5'-OH oligonucleotide still bound to the solid support.

After the final elongation cycle, the solid support-bound oligonucleotide is treated with a solution of 1,8-diazabicyclo[5.4.0]undec-7-ene in acetonitrile to remove the phosphorothioate protecting groups. The oligonucleotide, still bound to the solid support, is then removed from the reactor and treated with ammonium hydroxide at elevated temperature. This step simultaneously releases the oligonucleotide from the solid support and removes the protecting groups from the bases. The support is removed by filtration and the filtrate concentrated under reduced pressure to remove ammonium hydroxide.

The crude product is then purified by ion-pair chromatography at high pH and room temperature. The product is eluted from the column with a gradient of sodium chloride to accomplish both the final deprotection and purification of the drug substance. The elution profile is monitored by continuous UV absorption spectroscopy. The product is collected in fractions, and the fractions are analyzed for yield and purity. A number of mock test pools may be evaluated to determine the final pooling strategy. The acceptable fractions are pooled, and the pH is adjusted to 7.0±0.5. A final desalting step is performed using ultrafiltration. The resulting solution is lyophilized to yield the API.

1.1.29 Example 13

1.1.30 Material and Methods

1. In Silico Experiments

Candidate miRNAs and their target genes were screened and selected from public and commercial databases (e.g. TargetScan, BioGPS), using literature reports and in silico modeling results. Selection was based on the known and/or predicted interactions of miRNAs with selected target genes.

2. In Vitro Experiments

Human subcutaneous preadipocytes purchased from ZenBio, NC (Catalog #: SP-F-SL) were plated at confluence in 96-well plates and allowed to attach overnight in preadipocyte medium (DMEM/Ham's F-12 (1:1, v/v), HEPES buffer, fetal bovine serum and antibiotics) following the supplier's instructions. The next day, the medium was removed and replaced with differentiation medium for 2 days (DMEM/Ham's F-12 (1:1, v/v), 100 μM ascorbic acid, 0.85 μM insulin, 20 nM sodium selenite, 0.2 nM triiodothyronine, 1 μM dexamethasone, 100 μM isobutyl-methylxanthine, 100 nM Rosiglitazone and antibiotics). On Day 3, the cells were transfected with a miRNA analog (50 nM final concentration, each condition in sixplicate) using Dharmafect 1 and allowed to incubate for 3 days. Positive control wells were cultured in maintenance medium (DMEM/ Ham's F-12 (1:1, v/v) 100 µM ascorbic acid, 0.85 µM insulin, 20 nM sodium selenite, 0.2 nM triiodothyronine and antibiotics) supplemented with 100 nM Rosiglitazone. After 3 days, medium was exchanged every other day with fresh maintenance medium until day 14 post differentiation. On day 14, the cells were gently washed. Using a 96-well format, gene expression was determined by q-RT-PCR kit following the Manufacturer's instructions (TaqMan Gene Expression Cells-to-Ct kit, Life Technologies, cat #AM1728) and a 7900 HT Fast Real Time PCR System (Applied Biosystems). Control genes were TBP, GAPDH, LRP10 and UCP3. Using a 6-well format, mRNA Profiling was performed by Next Generation Sequencing (Illumina HiSeq 2500). Mitochondrial mass and activity as well as UCP-1 protein expression were determined by high content imaging (ArrayScan XTI and BMG Fluostar Galaxy reader), with UCP-1 antibody (abcam cat #ab10983), and MitoTracker® Deep Red FM (ThermoFisher M22426).

3. In Vivo Experiments

All animal studies were performed according to IACUC-approved protocols and in compliance with the Guide for the Care and Use of Laboratory Animals (National Research Council, 2011) in OLAW-assured and AAALAC-accredited facilities (The Jackson Laboratory, ME or the University of Buckingham, UK).

DIO male C57BL/6J mice were started on a 60% high fat diet at the age of 6-week old and were randomized according to body weight into treatment groups (8 to 12 animals per group) at various ages. After acclimation for 1 to 2 weeks, the mice were administered subcutaneous injections of saline or a miR-22 antagomir in the left inguinal fat pad (injections on Days 0, 2, and 4, then once a week for up to 12 weeks) while they remained on the 60% high fat diet. In some studies, another control group of mice was switched back to a normal 10% fat chow at the time of treatment randomization.

The mice were housed in positively ventilated polysulfonate cages with HEPA filtered air. The cages were changed every two weeks. The animal room was lighted entirely with artificial fluorescent lighting on controlled 12-hour light/dark cycle (6 a.m. to 6 p.m. light). The temperature and relative humidity ranges in the animal rooms were maintained at 22±4° C. and 50±15%, respectively. The animal room was set for 15 air exchanges per hour. Filtered tap water acidified to a pH of 2.5 to 3.0 was provided ad libitum. Mice were monitored on a daily basis. Body weights were measured weekly. Food consumption per cage (2 to 3 mice) was measured twice weekly at 3 and 4 day intervals. Rectal temperature was measured with a Physitemp, BAT-10 Thermometer.

Blood samples were collected by retro-orbital bleeds or cut tip of the tail. Mice underwent body composition analysis by NMR (Bruker LF50 BCA-Analyzer) while they were gently restrained to keep them quiet during this non-invasive measurement. Liver, heart, inguinal fat, perirenal or epididymal fat, and subscapular fat were weighed and collected for histology (10% formalin fixed, then transferred to 70% ethanol for shipment) and gene expression (flash frozen in duplicate). Spleens were weighed and discarded. Blood was collected and processed into serum or plasma at the time of necropsy by cardiocentesis. Serum level of alanine aminotransferase (ALT), aspartate aminotransferase (AST), glucose, insulin, cholesterol and triglycerides were measured.

In some studies, non-esterified fatty acids (NEFA), plasma leptin and adiponectin were also measured and oral glucose tolerance tests (OGTT) were performed. Oral glucose tolerance test was performed as follows: Six hours prior to the start of the glucose tolerance test (09h00), food was removed and animals were given clean cages. Mice were dosed with glucose at T=0 minutes. Glucose was dissolved in water and given to the mice by oral gavage at a dose of 2.5 g/kg p.o. Blood samples (100) were taken for the analysis of glucose concentration at −30, 0, 30, 60, 120 and 180 minutes relative to glucose administration. Blood samples were also taken at −30 and +30 minutes for insulin analysis. Food was returned at the end of the tolerance test.

Mice energy expenditure was measured by open-circuit indirect calorimetry with the animals in their home cages (Stocker, C. J., et al., 2007; Arch, J. R., et al., 2006). Recording of physical activity of mice from 7:00 pm to 8:00 am was performed with an infra-red recorder linked to a laptop. Analysis of activity was done by virtually drawing two lines across each cage and the number of times a line was broken by a mouse within 10-minute segments was scored.

4. miR-22 Inhibitors miR-22-3p antagomirs were purchased from Dharmacon GE, CO (miRIDIAN microRNA Hairpin Inhibitors) or Exiqon, MA (LNA™ microRNA Inhibitors) or designed (proprietary information) by AptamiR Therapeutics, Inc. and custom synthesized.

5. Statistical Analysis

Results given in the text and data points in the figures are shown as the mean±SEM. Statistical analysis used ANOVA and Student's t test, unless non parametric test were required, based on data distribution.

Example 14

Formulation of AdipomiRs (Adipocyte-Targeting miRNA)

"Omic" profiling of mature human subcutaneous adipocytes revealed high expression of Fatty Acid Translocase (FAT). FAT (a.k.a. scavenger receptor B or CD36), is an integral membrane receptor involved in fatty acid uptake into adipocytes. Therefore, the inventors set out to synthesize and validate a series of miRNA analogs that are covalently attached to fatty acids to facilitate preferential targeting to adipocyte FAT. To test the hypothesis that coupling miRNAs to a fatty acid leads to the selective active transport through FAT present on adipocyte surfaces, chimeras (AdipomiRs) made of single stranded miRNAs conjugated to fatty acids can be synthesized. Fatty acids of varying length can be attached at the 3' of miRNA analogs (Table 13 below). Fluorescently labeled and scrambled miRNA AdipomiRs can be additionally synthesized.

TABLE 13

| miRNA chimeras to be synthesized & tested. | | |
|---|---|---|
| Medium Chain Fatty Acids | C10: Decanoic Acid | C12: Dodecanoic Acid |

TABLE 13-continued miRNA chimeras to be synthesized & tested.

| Long Chain Fatty Acids | C18:1 Oleic Acid | C18: Stearic Acid |
| Very Long Chain Fatty Acids | C22 Docosanoic acid | C32:6 Dotriacontahexaenoic Acid |

Figure 17:
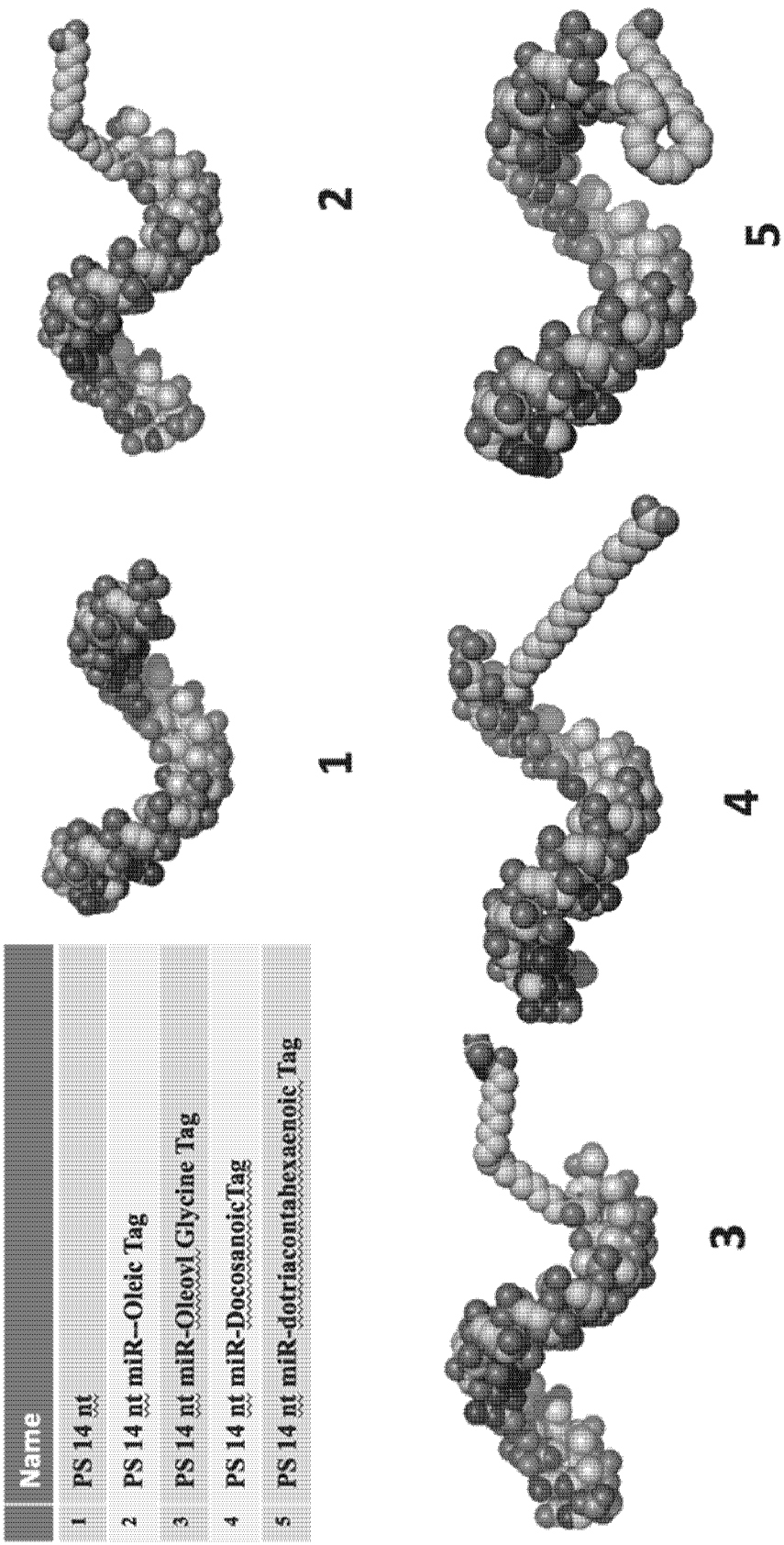
FIG. 17 High-quality 3D images of these AdipomiRs were obtained with the molecular visualization computer software program PyMOL.

High-quality 3D images (FIG. 17) of these AdipomiRs were obtained with the molecular visualization computer software program PyMOL.

Efficacy of AdipomiRs to target and deliver miRNA analogs into adipocytes can be evaluated primarily using pooled primary subcutaneous human adipocytes and control 3T3-L1 cells. Adipocytes can be incubated with various concentrations (25 to 100 nM) of AdipomiRs. At several time points from 1 to 48 hours, cells can be collected for confocal microscopy, high content imaging, and qRT-PCR of miRNA analogs and target genes to validate adipocyte uptake of functional thermogenic miRNAs. To validate that AdipomiR binding and internalization is FAT-dependent, pre-treatment of cells with sulfo-N-succinimidyl oleate (SSO, a known inhibitor of FAT) can be performed. Lastly, AdipomiRs can be tested with human pre-adipocytes, macrophages and hepatocytes as negative and positive controls, respectively.

AdipomiRs showing in vitro enhanced transport of functional thermogenic miRNA analogs in primary human adipocytes can be further tested in vivo. Using diet-induced obese (DIO) C57Bl/6J mice, selected AdipomiRs can be tested for tissue biodistribution and therapeutic efficacy. Toxicity can be monitored by twice daily monitoring of animals. Biodistribution of AdipomiRs to vital tissues and organs can be assessed by harvesting them on Day 7 after subcutaneous injections of the AdipomiRs in the inguinal fat pad on Days 0, 2 and 4, for histology staining and qRT-PCR of miRNA analogs and target genes. "Naked" miRNA analogs (15 mg/kg) can be used as controls. Efficacy of AdipomiRs to induce WAT to BAT thermogenic browning can be determined in DIO mice. At the start of the 8-week study, DIO mice can be maintained on a normal chow or 60% high fat diet and treated with subcutaneous injections of AdipomiRs into the inguinal fat pad on day 0, 2, and 4 of the first week then followed with once weekly injections for the remainder of the study. Post-treatment, animals can be sacrificed with blood collected for analysis along with vital tissues and organs for histological and gene expression analysis. Lastly, mice can undergo body composition analysis by NMR at weeks 1 and 8 of treatment.

Example 15

Formulation and Validation of LipomiRs (Liposome-Carrying miRNAs) Nanoparticles for Drug Delivery While conjugation of fatty acids to miRNAs may prove effective in targeting specifically adipocytes, the use of a nanoparticle drug delivery system can be of further benefit given their high cargo capacity and the need to package double-stranded miRNAs to achieve sufficient intra-cellular delivery. Therefore, this example focuses on the synthesis of lipid nanoparticles for delivering high copy numbers of thermogenic miRNA analogs to subcutaneous adipocytes.

Liposome Synthesis. Inventors conducted pilot experiments in vitro and in vivo with several PEGylated lipid nanoparticles (LNPs) to deliver miRNAs to adipocytes or adipose tissues. Results showed that non-targeted LNPs delivered associated miRNA analogs within tissues proximal to the injection site. However, these PEGylated LNPs exhibited various tissue/organ biodistribution patterns attributable to nanoparticle composition, PEG content and route of administration. Dissociation of nucleic acids from cationic liposomes can occur quickly in the presence of human serum. Furthermore, cationic lipids used to increase loading/association of miRNAs with LNPs trigger an immune reaction via Toll-like Receptors. As such, strategies which replace cationic lipids for miRNA association and delivery are of significant interest. Consequently, inventors began developing novel liposomes free of cationic lipids and PEG for safe and useful for the effective delivery to adipocytes. Using a mini-extruder with 50-200 nm pore size polycarbonate membranes, the inventors characterized a variety of liposomes of differing compositions. To date, the best candidate contains sphingomyelin, 1,2-dimyristoyl-sn-glycero-3-phosphocholine (DMPC), and cholesterol at a 40:40:20% weight to weight ratio. These "SDC" liposomes are well-characterized with a peak mean diameter of 140 nm, a polydispersity index (PDI) of <0.01, and a Zeta potential of +2.32 mV with no significant changes during storage over 1 month at 4° C.

Figure 18:
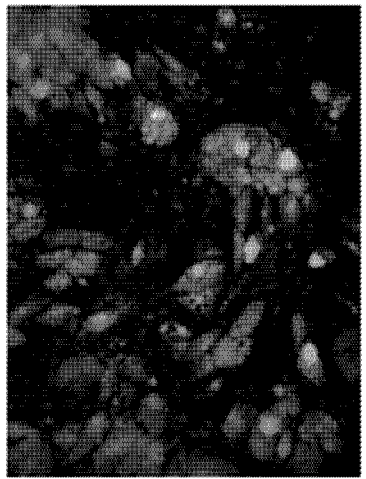
FIG. 18 Using high content fluorescence imaging, these SDC liposome miRNA complexes showed efficient delivery of fluorescent and functional miRNAs into mature human adipocytes in vitro
Figure 18:
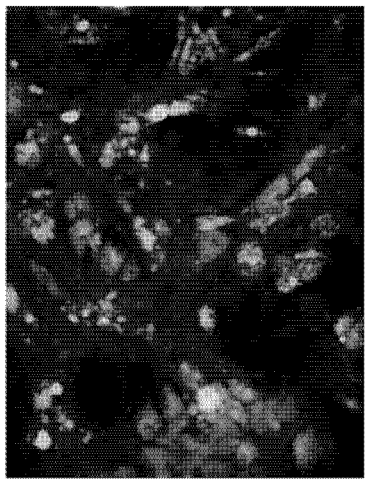
Figure 18:
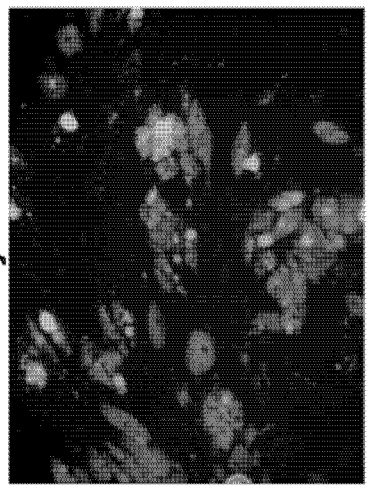

Complexation of SDC Liposomes with thermogenic miRNAs. Introduction of miRNAs post SDC liposome purification slightly increased their size to ~147 nm with PDI of <0.032 and reduced their zeta potential from +2.32 mV to −55.7 mV, indicative of miRNAs surface association. Using high content fluorescence imaging, these SDC liposome miRNA complexes showed efficient delivery of fluorescent and functional miRNAs into mature human adipocytes in vitro (FIG. 18).

Fatty acid conjugated miRNAs anchoring to SDC liposomes (LipomiRs Formulation). To avoid the cationic lipid pitfalls, the inventors propose using the fatty acid conjugated miRNAs (AdipomiRs) to help anchor the thermogenic miRNA analogs (compounds of the disclosure) onto the SDC liposome membrane surfaces. Two approaches can be employed. Firstly, LipomiRs can be introduced during lipid film preparation/hydration, resulting in improved internal and external anchoring to SDC liposomes. Secondly, SDC liposomes can be prepared beforehand followed by incubation with fatty acid conjugated miRNAs for surface membrane anchoring via lipophilic interactions. The first approach suffers from significant loss of conjugated miRNA during the liposome sizing extrusion process but benefits from higher miRNAs internal encapsulation within the liposome lumen, thereby affording additional protection and delivery capacity during systemic transport. As a complementary approach, the inventors can attempt to achieve encapsulation of minimally modified miRNAs conjugated to fatty acid for membrane anchoring during lipid hydration as a means of reducing costs and complexity. Free or fatty acid conjugated miRNA analogs can be added either during or after SDC liposome formation to compare loading efficacy. LipomiR size and charge can be used to assess exterior loading of miRNAs while total miRNA retention levels can be assayed by UV-vis spectroscopy and miRNA extraction using Triton X-100 followed by RiboGreen fluorescence quantification. Ionic competition using dextran sulfate can be used to evaluate fatty acid anchoring of miRNAs to the liposome surface. To evaluate miRNA stability, miRNA-loaded SDC liposomes can be incubated in the presence of human serum. At various time points, miRNAs can be evaluated for degradation by HPLC. While miRNAs can complex with SDC liposomes due to the presence of the weakly cationic DMPC, the conjugation of fatty acid may be a key factor in improving long term stability within assembled LipomiRs. Furthermore, it may allow for removal of DMPC entirely, thereby further simplifying scale-up manufacturability and safety. Additionally, a soluble fluorescent marker can be packaged internally within these liposomes during preparation to reveal a two-tone fluorescent nanoparticle with peripheral rim vs. luminal staining pattern.

In vitro validation of LipomiRs delivery of functional miRNAs. Validation of LipomiR delivery of miRNAs to adipocytes can be conducted as described in example 15. Cell viability assays (MTT & LDH) can be used to evaluate the cytotoxicity of our LipomiRs. Previously, we have shown that an exosome can deliver fluorescent miRNA to mature adipocytes through cationic DMPC association. Uptake of miRNA was visually confirmed by microscopy along with a dose dependent induction of UCP1 seen by qPCR analysis. UCP1 upregulation was analogous to positive control of free miRNA delivered by a DharmaFect transfection reagent. LipomiRs using fatty acid conjugated miRNA should hopefully replicate this enhanced profile.

In vivo LipomiRs biodistribution and efficacy profiles. Biodistribution and efficacy of LipomiR formulation that prove effective in vitro can be tested in vivo as described in example 15.

Example 16

Formulation & Validation of AdipoLipomiRs (Adipocyte-Targeted Liposome-Carrying miRNAs) Nanoparticles for Drug Delivery The use of fatty acid conjugated to miRNAs in LipomiRs may result in a decrease of targeting to adipocytes via FAT binding. Therefore, this example describes adipocyte targeted delivery of miRNAs through bioconjugation to other high binding affinity adipocyte targeting factors (instead of a fatty acid) onto the liposome surface.

Adaptable AdipoLipomiRs surface functionalization. To maximize the ability to generate novel AdipoLipomiRs, the inventors can employ disulfide based bioconjugation for ligand anchoring to the liposomes surface. The inventors can test introduction of 1,2-dioleoyl-sn-glycero-3-phosphoethanolamine-N-[3-(2-pyridyldithio)propionate] (PDP PE) during SDC liposome preparation. PDP-PE lipid head group consists of a pyridine-2-thione ring linked covalently by a [redox] sensitive disulfide bond. Pyridine-2-thione is a strong electron withdrawing group which can be readily displaced by introduction of a reduced thiol (i.e. HS-R1, R1=adipocyte targeting ligand/moiety) or other reducing agent (TCEP, DTT, β-ME, etc.). Reactivity occurs at a 1:1 stoichiometric rate, whereby the displaced pyridine-2-thione ring becomes chemically inert, yet UV-vis spectrophotometrically active at 343 nm, thereby allowing facile quantitation. This is particularly useful when conjugated molecules of choice lack means of detection. PDP-PE can also be used to monitor liposome particle stability as internal PDP-PE will not be susceptible to reducing agents unless membrane breakage occurs. Like PDP-PE, phosphatidylethanolamine (PE) can be used, whereby after preparation, surface PE can be reacted with succinimidyl 3-(2-pyridyldithio)-propionate (SPDP) or 2-iminothiolane (Traut's reagent) and dithio-dipyridine (DTDP) to introduce the same functional disulfide-pyridine-2-thione ring linkage for subsequent conjugations. Lastly, if necessary, the introduction of additional crosslinkers and spacers can be considered.

Conjugation of Thrombospondin-1, anti-FAT targeting peptide. If the use of fatty acids to target AdipoLipomiRs to adipocyte FAT fails, other targeting alternatives can be tested. Anti-FAT antibodies could be employed but suffer from cost and scalability. Instead, Applicants will use adipocyte binding peptides given their advantages of being simpler, ease to modify, cross-linking reactivity, and scalability costs. FAT is a multi-functional protein with numerous binding ligands such as Thrombospondin-1 (TSP-1) involved in cell to cell/matrix binding. Anti-FAT TSP-1 peptide (GVITRIR (SEQ ID NO:1)) was identified and used to generate novel peptide mimetics with enhanced binding (<10 nM) for use as antiangiogenic cancer therapeutics tested in clinical trials by Abbott Laboratories. The inventors can re-purpose these highly specific anti-FAT peptides as AdipoLipomiR targeting moieties. Native TSP-1 peptide, along with enhanced mimetics and scrambled sequences can be synthesized with the addition of a Cysteine with a freely reduced thiol for subsequent conjugation onto SDC Liposomes/LipomiRs via PDP-PE reactivity (JPT Peptide Technologies). To validate functional binding before in vitro experiments, AdipoLipomiRs can be incubated with His-tag purified human FAT (Thermofisher) and assayed for bound FAT binding by gel-electrophoresis. Additionally, fluorescent tags can be introduced to help validate liposome labeling while the use of excess free non-conjugated TSP-1 peptides can be used as binding competitors to validate FAT/CD36 binding. Lastly, because TSP-1 peptide can be attached to the SDC liposome by a disulfide bond, negative controls can be made through pre-treatment with reducing agents.

In vitro validation of AdipoLipomiR to deliver functional miRNAs. Similarly to LipomiRs in Aim 2, AdipoLipomiRs can be administered to cells in culture as described in sections C1.2 and C2.4. Different combinations of AdipoLipomiRs (+/− miRNA, TSP-1 peptides, competitor TSP-1 peptides, etc.) can be used. Aforementioned cell viability assays can also be used to address AdipoLipomiR toxicity profiles.

In vivo AdipoLipomiR biodistribution and efficacy profiles. AdipoLipomiRs utility as a platform technology for delivery of thermogenic miRNAs to treat obesity and diabetes can be tested in DIO C57Bl/6J mice as described in previous examples.

REFERENCES

1. Ng, M., et al., Global, regional, and national prevalence of overweight and obesity in children and adults during 1980-2013: a systematic analysis for the Global Burden of Disease Study 2013. Lancet, 2014. 384 (9945): p. 766-81.
2. Wilborn, C., et al., Obesity: prevalence, theories, medical consequences, management, and research directions. J Int Soc Sports Nutr, 2005. 2: p. 4-31.
3. Wang, Y., et al., Will all Americans become overweight or obese? estimating the progression and cost of the US obesity epidemic. Obesity (Silver Spring), 2008. 16 (10): p. 2323-30.
4. Haslam, D. W. and W. P. James, Obesity. Lancet, 2005. 366 (9492): p. 1197-209.
5. Cinti, S., The adipose organ at a glance. Dis Model Mech, 2012. 5(5): p. 588-94.
6. Cohen, P. and B. M. Spiegelman, Brown and Beige Fat: Molecular Parts of a Thermogenic Machine. Diabetes, 2015. 64 (7): p. 2346-51.

7. Sharp, L. Z., et al., Human BAT possesses molecular signatures that resemble beige/brite cells. PLoS One, 2012. 7(11): p. e49452.
8. Wu, J., P. Cohen, and B. M. Spiegelman, Adaptive thermogenesis in adipocytes: is beige the new brown? Genes Dev, 2013. 27 (3): p. 234-50.
9. Virtanen, K. A., W. D. van Marken Lichtenbelt, and P. Nuutila, Brown adipose tissue functions in humans. Biochim Biophys Acta, 2013. 1831 (5): p. 1004-8.
10. Collins, S., E. Yehuda-Shnaidman, and H. Wang, Positive and negative control of Ucp1 gene transcription and the role of beta-adrenergic signaling networks. International journal of obesity, 2010. 34 Suppl 1: p. S28-33.
11. Mozo, J., et al., Thermoregulation: what role for UCPs in mammals and birds? Bioscience reports, 2005. 25 (3-4): p. 227-49.
12. Shore, A., et al., Role of Ucp1 enhancer methylation and chromatin remodelling in the control of Ucp1 expression in murine adipose tissue. Diabetologia, 2010. 53 (6): p. 1164-73.
13. Tateishi, K., et al., Role of Jhdm2a in regulating metabolic gene expression and obesity resistance. Nature, 2009. 458 (7239): p. 757-61.
14. Okada, Y., K. Tateishi, and Y. Zhang, Histone demethylase JHDM2A is involved in male infertility and obesity. Journal of andrology, 2010. 31 (1): p. 75-8.
15. Aagaard, L. A., et al., Engineering and optimization of the miR-106b cluster for ectopic expression of multiplexed anti-HIV RNAs. Gene therapy, 2008. 15: p. 1536-49.
16. Liang, Y., et al., Characterization of microRNA expression profiles in normal human tissues. BMC Genomics, 2007. 8: p. 166.
17. Stocker, C. J., et al., Prevention of diet-induced obesity and impaired glucose tolerance in rats following administration of leptin to their mothers. Am J Physiol Regul Integr Comp Physiol, 2007. 292 (5): p. R1810-8.
18. Arch, J. R., et al., Some mathematical and technical issues in the measurement and interpretation of open-circuit indirect calorimetry in small animals. Int J Obes (Lond), 2006. 30 (9): p. 1322-31.
19. Hondares, E., et al., PPARalpha induces PGC-1alpha gene expression and contributes to the thermogenic activation of brown fat; involvement of PRDM16. The Journal of biological chemistry, 2011.
20. Xue, B., et al., Transcriptional synergy and the regulation of Ucp1 during brown adipocyte induction in white fat depots. Mol Cell Biol, 2005. 25 (18): p. 8311-22.
21. Kanasaki, K. and D. Koya, Biology of obesity: lessons from animal models of obesity. Journal of biomedicine & biotechnology, 2011. 2011: p. 197636.
22. Bartesaghi, S., et al., Thermogenic activity of UCP1 in human white fat-derived beige adipocytes. Mol Endocrinol, 2015. 29 (1): p. 130-9.
23. Arch, J. R. and P. Trayhurn, Detection of thermogenesis in rodents in response to anti-obesity drugs and genetic modification. Front Physiol, 2013. 4: p. 64.
24. Price, N. L. and C. Fernandez-Hernando, miRNA regulation of white and brown adipose tissue differentiation and function. Biochim Biophys Acta, 2016.
25. Xie, H., L. Sun, and H. F. Lodish, Targeting microRNAs in obesity. Expert Opin Ther Targets, 2009. 13 (10): p. 1227-38.
26. Arner, P. and A. Kulyte, MicroRNA regulatory networks in human adipose tissue and obesity. Nat Rev Endocrinol, 2015. 11 (5): p. 276-88.
27. Abente, E. J., et al., MicroRNAs in obesity-associated disorders. Arch Biochem Biophys, 2016. 589: p. 108-19.
28. Zhu, H. and S. W. Leung, Identification of microRNA biomarkers in type 2 diabetes: a meta-analysis of controlled profiling studies. Diabetologia, 2015. 58 (5): p. 900-11.
29. Son, Y. H., et al., Regulation of Adipocyte Differentiation via MicroRNAs. Endocrinol Metab (Seoul), 2014. 29 (2): p. 122-35.
30. Gurha, P., et al., microRNA-22 promotes heart failure through coordinate suppression of PPAR/ERR-nuclear hormone receptor transcription. PLoS One, 2013. 8 (9): p. e75882.
31. Lidell, M. E. and S. Enerback, Brown adipose tissue—a new role in humans? Nat Rev Endocrinol, 2010. 6 (6): p. 319-25.
32. Algire, C., D. Medrikova, and S. Herzig, White and brown adipose stem cells: from signaling to clinical implications. Biochim Biophys Acta, 2013. 1831 (5): p. 896-904.
33. Cannon, B. and J. Nedergaard, Yes, even human brown fat is on fire! J Clin Invest, 2012. 122 (2): p. 486-9.
34. Celi, F. S., T. N. Le, and B. Ni, Physiology and relevance of human adaptive thermogenesis response. Trends Endocrinol Metab, 2015. 26 (5): p. 238-47.
35. Lee, P., M. M. Swarbrick, and K. K. Ho, Brown adipose tissue in adult humans: a metabolic renaissance. Endocr Rev, 2013. 34 (3): p. 413-38.
36. Nedergaard, J. and B. Cannon, The changed metabolic world with human brown adipose tissue: therapeutic visions. Cell Metab, 2010. 11 (4): p. 268-72.
37. Kim, S. H. and J. Plutzky, Brown Fat and Browning for the Treatment of Obesity and Related Metabolic Disorders. Diabetes Metab J, 2016. 40 (1): p. 12-21.
38. Bonet, M. L., P. Oliver, and A. Palou, Pharmacological and nutritional agents promoting browning of white adipose tissue. Biochim Biophys Acta, 2013. 1831 (5): p. 969-85.
39. Lowell, B. B. and B. M. Spiegelman, Towards a molecular understanding of adaptive thermogenesis. Nature, 2000. 404 (6778): p. 652-60.
40. Cereijo, R., M. Giralt, and F. Villarroya, Thermogenic brown and beige/brite adipogenesis in humans. Ann Med, 2015. 47 (2): p. 169-77.
41. Kozak, L. P., Brown fat and the myth of diet-induced thermogenesis. Cell Metab, 2010. 11 (4): p. 263-7.
42. Vosselman, M. J., W. D. van Marken Lichtenbelt, and P. Schrauwen, Energy dissipation in brown adipose tissue: from mice to men. Mol Cell Endocrinol, 2013. 379 (1-2): p. 43-50.
43. Grundlingh, J., et al., 2,4-dinitrophenol (DNP): a weight loss agent with significant acute toxicity and risk of death. Journal of medical toxicology: official journal of the American College of Medical Toxicology, 2011. 7(3): p. 205-12.
44. Lin, J. Z., et al., Pharmacological Activation of Thyroid Hormone Receptors Elicits a Functional Conversion of White to Brown Fat. Cell Rep, 2015. 13 (8): p. 1528-37.
45. Arch, J. R., Challenges in beta(3)-Adrenoceptor Agonist Drug Development. Ther Adv Endocrinol Metab, 2011.2 (2): p. 59-64.
46. Cypess, A. M., et al., Activation of human brown adipose tissue by a beta3-adrenergic receptor agonist. Cell Metab, 2015. 21 (1): p. 33-8.

47. Perry, R. J., et al., Reversal of hypertriglyceridemia, fatty liver disease, and insulin resistance by a liver-targeted mitochondrial uncoupler. Cell Metab, 2013. 18 (5): p. 740-8.
48. Tao, H., et al., Nat Med, 2014. 20 (11): p. 1263-9.
49. Saito, M., Capsaicin and Related Food Ingredients Reducing Body Fat Through the Activation of TRP and Brown Fat Thermogenesis. Adv Food Nutr Res, 2015. 76: p. 1-28.
50. Stanford, K. I., et al., Brown adipose tissue regulates glucose homeostasis and insulin sensitivity. The Journal of clinical investigation 2013. 123 (1): p. 215-23.
51. Li, Z. and T. M. Rana, Therapeutic targeting of microRNAs: current status and future challenges. Nat Rev Drug Discov 2014. 13 (8): p. 622-38.
52. Beaucage, et al., Tetrahedron 1992. 48, 2223.
53. Alul, et al., Nucleic Acids Research 1991. 19, 1527.
54. Wright, et al., Tetrahedron Letters 1993. 34, 3373.
55. Pon, R. T. in Protocols for Oligonucleotides and Analogs, 8th, ed., Humana Press, Totowa, 1993.
56. Langin, D. et al., Biochimica et Biophysica Acta 2010. 1801, 372-376.
57. Minto C. F. et al., J Pharmacol Exp Ther 1997, 93-102.

The invention claimed is:

1. A mir-22 miRNA antagonist of the formula (SEQ ID NO: 4)

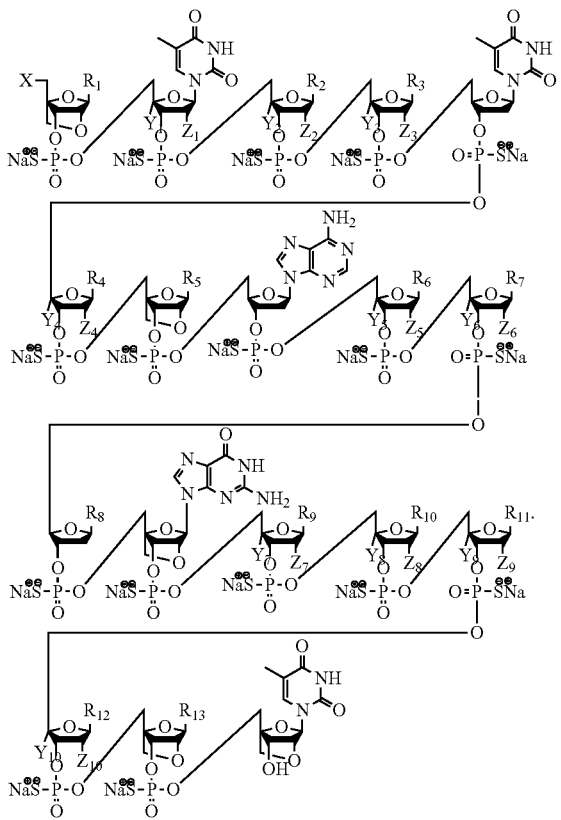

2. The mir-22 miRNA antagonist of claim 1, wherein the mir-22 miRNA is the mature miR-22-3p.

3. A method of increasing thermogenesis in a subject comprising administering to the subject the mir-22 miRNA antagonist of claim 1.

4. The mir-22 miRNA antagonist of claim 1, wherein the mir-22 miRNA antagonist is conjugated to a fatty acid.

5. The mir-22 miRNA antagonist of claim 4, wherein the fatty acid is a C10-35 chain fatty acid.

6. The mir-22 miRNA antagonist of claim 4, wherein the fatty acid is selected from decanoic acid, palmitic acid, dodecanoic acid, oleic acid, stearic acid, eicosapentaenoic acid, docosanoic acid, docosahexaenoic acid, and dotriacontahexaenoic acid.

7. A method for delivering a mir-22 miRNA antagonist to an adipocyte of a subject comprising administering the mir-22 miRNA antagonist of claim 2 to the adipocyte.

8. The method of claim 7, wherein the adipocyte is in vivo.

9. The method of claim 7, wherein at least 50% of the mir-22 miRNA antagonist is delivered to adipocytes of the subject.

10. The mir-22 miRNA antagonist of claim 1, wherein the mir-22 miRNA antagonist is conjugated to a polypeptide.

11. The mir-22 miRNA antagonist of claim 10, wherein the polypeptide is a polypeptide comprising the sequence GVITRIR (SEQ ID NO: 1).

12. The mir-22 miRNA antagonist of claim 10, wherein the polypeptide is a polypeptide comprising the sequence CKGGRAKDC (SEQ ID NO: 3).

13. The mir-22 miRNA antagonist of claim 10, wherein the polypeptide is Hexarelin (His-(D)2-methyl-Trp-Ala-Trp-(D)Phe-Lys-NH$_2$).

14. The mir-22 miRNA antagonist of claim 1, wherein the mir-22 miRNA antagonist is conjugated to a targeting element.

15. A mir-22 miRNA antagonist, wherein the mir-22 miRNA antagonist structure comprises SEQ ID NO: 16.

16. A mir-22 miRNA antagonist, wherein the mir-22 miRNA antagonist structure comprises SEQ ID NO: 18.

* * * * *

SEQUENCE LISTING

```
<160> NUMBER OF SEQ ID NOS: 18

<210> SEQ ID NO 1
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 1

Gly Val Ile Thr Arg Ile Arg
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 2

His Trp Ala Trp Phe Leu
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 3

Cys Lys Gly Gly Arg Ala Lys Asp Cys
1               5

<210> SEQ ID NO 4
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(18)
<223> OTHER INFORMATION: All internucleotide linkages are
      phosphorothioates
<220> FEATURE:
<221> NAME/KEY: modified_base
<222> LOCATION: (1)..(1)
<223> OTHER INFORMATION: Locked nucleic acid
<220> FEATURE:
<221> NAME/KEY: modified_base
<222> LOCATION: (1)..(1)
<223> OTHER INFORMATION: 5-methyl substitution
<220> FEATURE:
<221> NAME/KEY: modified_base
```

```
<222> LOCATION: (2)..(2)
<223> OTHER INFORMATION: Locked nucleic acid
<220> FEATURE:
<221> NAME/KEY: modified_base
<222> LOCATION: (4)..(4)
<223> OTHER INFORMATION: 2' OCH3 substitution and not methylated at the
      5 position
<220> FEATURE:
<221> NAME/KEY: modified_base
<222> LOCATION: (7)..(7)
<223> OTHER INFORMATION: Locked nucleic acid
<220> FEATURE:
<221> NAME/KEY: modified_base
<222> LOCATION: (7)..(7)
<223> OTHER INFORMATION: 5-methyl substitution
<220> FEATURE:
<221> NAME/KEY: modified_base
<222> LOCATION: (10)..(10)
<223> OTHER INFORMATION: 2' OCH3 substitution and not methylated at the
      5 position
<220> FEATURE:
<221> NAME/KEY: modified_base
<222> LOCATION: (12)..(12)
<223> OTHER INFORMATION: Locked nucleic acid
<220> FEATURE:
<221> NAME/KEY: modified_base
<222> LOCATION: (14)..(14)
<223> OTHER INFORMATION: Locked nucleic acid
<220> FEATURE:
<221> NAME/KEY: modified_base
<222> LOCATION: (14)..(14)
<223> OTHER INFORMATION: 5-methyl substitution
<220> FEATURE:
<221> NAME/KEY: modified_base
<222> LOCATION: (15)..(15)
<223> OTHER INFORMATION: Locked nucleic acid
<220> FEATURE:
<221> NAME/KEY: modified_base
<222> LOCATION: (17)..(17)
<223> OTHER INFORMATION: Locked nucleic acid
<220> FEATURE:
<221> NAME/KEY: modified_base
<222> LOCATION: (17)..(17)
<223> OTHER INFORMATION: 5-methyl substitution
<220> FEATURE:
<221> NAME/KEY: modified_base
<222> LOCATION: (18)..(18)
<223> OTHER INFORMATION: Locked nucleic acid

<400> SEQUENCE: 4
cttcttcaac tggcagct                                                 18

<210> SEQ ID NO 5
<211> LENGTH: 23
<212> TYPE: RNA
<213> ORGANISM: Artificial Sequence
<220> FEATURE:
<223> OTHER INFORMATION: Synthetic oligonucleotide

<400> SEQUENCE: 5
uggaaaugaa uuacaggcag cug                                           23

<210> SEQ ID NO 6
<211> LENGTH: 22
<212> TYPE: RNA
<213> ORGANISM: Artificial Sequence
<220> FEATURE:
<223> OTHER INFORMATION: Synthetic oligonucleotide

<400> SEQUENCE: 6
aagcugccag uugaagaacu gu                                            22

<210> SEQ ID NO 7
```

```
<211> LENGTH: 23
<212> TYPE: RNA
<213> ORGANISM: Artificial Sequence
<220> FEATURE:
<223> OTHER INFORMATION: Synthetic oligonucleotide

<400> SEQUENCE: 7
cccuuccacc ccauuggcag cuc                                             23

<210> SEQ ID NO 8
<211> LENGTH: 22
<212> TYPE: RNA
<213> ORGANISM: Artificial Sequence
<220> FEATURE:
<223> OTHER INFORMATION: Synthetic oligonucleotide

<400> SEQUENCE: 8
aagcugccag uugaagaacu gu                                              22

<210> SEQ ID NO 9
<211> LENGTH: 23
<212> TYPE: RNA
<213> ORGANISM: Artificial Sequence
<220> FEATURE:
<223> OTHER INFORMATION: Synthetic oligonucleotide

<400> SEQUENCE: 9
cuccgggccc cauuuggcag cuc                                             23

<210> SEQ ID NO 10
<211> LENGTH: 22
<212> TYPE: RNA
<213> ORGANISM: Artificial Sequence
<220> FEATURE:
<223> OTHER INFORMATION: Synthetic oligonucleotide

<400> SEQUENCE: 10
aagcugccag uugaagaacu gu                                              22

<210> SEQ ID NO 11
<211> LENGTH: 84
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: variation
<222> LOCATION: (62)..(62)
<223> OTHER INFORMATION: n is a, c, g, or u
<220> FEATURE:
<221> NAME/KEY: variation
<222> LOCATION: (72)..(73)
<223> OTHER INFORMATION: n is a, c, g, or u

<400> SEQUENCE: 11
ggcugagccg caguaguucu ucaguggcaa gcuuuauguc cugacccagc uaaagcugcc     60
ancugaagaa cnnugcccuc ugcc                                            84

<210> SEQ ID NO 12
<211> LENGTH: 22
<212> TYPE: RNA
<213> ORGANISM: Artificial Sequence
<220> FEATURE:
<223> OTHER INFORMATION: Synthetic oligonucleotide

<400> SEQUENCE: 12
aguucuucag uggcaagcuu ua                                              22
```

```
<210> SEQ ID NO 13
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(18)
<223> OTHER INFORMATION: All internucleotide linkages are
      phosphorothioates
<220> FEATURE:
<221> NAME/KEY: modified_base
<222> LOCATION: (1)..(1)
<223> OTHER INFORMATION: Locked nucleic acid
<220> FEATURE:
<221> NAME/KEY: modified_base
<222> LOCATION: (1)..(1)
<223> OTHER INFORMATION: cytosine, 5-methyl cytosine, guanine, or
      thymine
<220> FEATURE:
<221> NAME/KEY: modified_base
<222> LOCATION: (3)..(4)
<223> OTHER INFORMATION: cytosine, 5-methyl cytosine, or thymine
<220> FEATURE:
<221> NAME/KEY: modified_base
<222> LOCATION: (6)..(6)
<223> OTHER INFORMATION: cytosine, 5-methyl cytosine, or thymine
<220> FEATURE:
<221> NAME/KEY: modified_base
<222> LOCATION: (7)..(7)
<223> OTHER INFORMATION: Locked nucleic acid
<220> FEATURE:
<221> NAME/KEY: modified_base
<222> LOCATION: (7)..(7)
<223> OTHER INFORMATION: adenine, 5-methyl cytosine, or cytosine
<220> FEATURE:
<221> NAME/KEY: modified_base
<222> LOCATION: (9)..(9)
<223> OTHER INFORMATION: adenine, 5-methyl cytosine, or cytosine
<220> FEATURE:
<221> NAME/KEY: modified_base
<222> LOCATION: (10)..(10)
<223> OTHER INFORMATION: cytosine, 5-methyl cytosine, or thymine
<220> FEATURE:
<221> NAME/KEY: modified_base
<222> LOCATION: (11)..(11)
<223> OTHER INFORMATION: guanine or thymine
<220> FEATURE:
<221> NAME/KEY: modified_base
<222> LOCATION: (12)..(12)
<223> OTHER INFORMATION: Locked nucleic acid
<220> FEATURE:
<221> NAME/KEY: modified_base
<222> LOCATION: (13)..(13)
<223> OTHER INFORMATION: cytosine, 5-methyl cytosine, or guanine
<220> FEATURE:
<221> NAME/KEY: modified_base
<222> LOCATION: (14)..(14)
<223> OTHER INFORMATION: adenine, 5-methyl cytosine, or cytosine
<220> FEATURE:
<221> NAME/KEY: modified_base
<222> LOCATION: (15)..(15)
<223> OTHER INFORMATION: adenine or guanine
<220> FEATURE:
<221> NAME/KEY: modified_base
<222> LOCATION: (16)..(16)
<223> OTHER INFORMATION: cytosine, 5-methyl cytosine, or guanine
<220> FEATURE:
<221> NAME/KEY: modified_base
<222> LOCATION: (17)..(17)
<223> OTHER INFORMATION: Locked nucleic acid
<220> FEATURE:
<221> NAME/KEY: modified_base
<222> LOCATION: (17)..(17)
<223> OTHER INFORMATION: cytosine, 5-methyl cytosine, or thymine
<220> FEATURE:
```

<221> NAME/KEY: modified_base
<222> LOCATION: (18)..(18)
<223> OTHER INFORMATION: Locked nucleic acid

<400> SEQUENCE: 13
ntnntnnann ngnnnnnt                                                18

<210> SEQ ID NO 14
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(18)
<223> OTHER INFORMATION: All internucleotide linkages are
      phosphorothioates
<220> FEATURE:
<221> NAME/KEY: modified_base
<222> LOCATION: (1)..(2)
<223> OTHER INFORMATION: Locked nucleic acid
<220> FEATURE:
<221> NAME/KEY: modified_base
<222> LOCATION: (3)..(3)
<223> OTHER INFORMATION: 5-methyl substitution
<220> FEATURE:
<221> NAME/KEY: modified_base
<222> LOCATION: (3)..(3)
<223> OTHER INFORMATION: 2' OCH3 substitution
<220> FEATURE:
<221> NAME/KEY: modified_base
<222> LOCATION: (6)..(6)
<223> OTHER INFORMATION: 5-methyl substitution
<220> FEATURE:
<221> NAME/KEY: modified_base
<222> LOCATION: (6)..(6)
<223> OTHER INFORMATION: 2' OCH3 substitution
<220> FEATURE:
<221> NAME/KEY: modified_base
<222> LOCATION: (7)..(7)
<223> OTHER INFORMATION: Locked nucleic acid
<220> FEATURE:
<221> NAME/KEY: modified_base
<222> LOCATION: (9)..(9)
<223> OTHER INFORMATION: 5-methyl substitution
<220> FEATURE:
<221> NAME/KEY: modified_base
<222> LOCATION: (9)..(9)
<223> OTHER INFORMATION: 2' OCH3 substitution
<220> FEATURE:
<221> NAME/KEY: modified_base
<222> LOCATION: (12)..(12)
<223> OTHER INFORMATION: Locked nucleic acid
<220> FEATURE:
<221> NAME/KEY: modified_base
<222> LOCATION: (13)..(13)
<223> OTHER INFORMATION: 5-methyl substitution
<220> FEATURE:
<221> NAME/KEY: modified_base
<222> LOCATION: (13)..(13)
<223> OTHER INFORMATION: 2' OCH3 substitution
<220> FEATURE:
<221> NAME/KEY: modified_base
<222> LOCATION: (14)..(15)
<223> OTHER INFORMATION: Locked nucleic acid
<220> FEATURE:
<221> NAME/KEY: modified_base
<222> LOCATION: (16)..(16)
<223> OTHER INFORMATION: 2' OCH3 substitution
<220> FEATURE:
<221> NAME/KEY: modified_base
<222> LOCATION: (17)..(18)
<223> OTHER INFORMATION: Locked nucleic acid

<400> SEQUENCE: 14
ttcttcaact ggcagctt                                                   18

<210> SEQ ID NO 15
<211> LENGTH: 19
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(18)
<223> OTHER INFORMATION: All internucleotide linkages are
      phosphorothioates
<220> FEATURE:
<221> NAME/KEY: modified_base
<222> LOCATION: (1)..(2)
<223> OTHER INFORMATION: Locked nucleic acid
<220> FEATURE:
<221> NAME/KEY: modified_base
<222> LOCATION: (5)..(5)
<223> OTHER INFORMATION: 5-methyl substitution
<220> FEATURE:
<221> NAME/KEY: modified_base
<222> LOCATION: (5)..(5)
<223> OTHER INFORMATION: Locked nucleic acid
<220> FEATURE:
<221> NAME/KEY: modified_base
<222> LOCATION: (8)..(8)
<223> OTHER INFORMATION: 5-methyl substitution
<220> FEATURE:
<221> NAME/KEY: modified_base
<222> LOCATION: (8)..(8)
<223> OTHER INFORMATION: Locked nucleic acid
<220> FEATURE:
<221> NAME/KEY: modified_base
<222> LOCATION: (11)..(11)
<223> OTHER INFORMATION: Locked nucleic acid
<220> FEATURE:
<221> NAME/KEY: modified_base
<222> LOCATION: (14)..(14)
<223> OTHER INFORMATION: Locked nucleic acid
<220> FEATURE:
<221> NAME/KEY: modified_base
<222> LOCATION: (15)..(15)
<223> OTHER INFORMATION: 5-methyl substitution
<220> FEATURE:
<221> NAME/KEY: modified_base
<222> LOCATION: (15)..(15)
<223> OTHER INFORMATION: 2' OCH3 substitution
<220> FEATURE:
<221> NAME/KEY: modified_base
<222> LOCATION: (18)..(18)
<223> OTHER INFORMATION: 5-methyl substitution
<220> FEATURE:
<221> NAME/KEY: modified_base
<222> LOCATION: (17)..(19)
<223> OTHER INFORMATION: Locked nucleic acid

<400> SEQUENCE: 15
agttcttcaa ctggcagct                                                  19

<210> SEQ ID NO 16
<211> LENGTH: 22
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(18)
<223> OTHER INFORMATION: All internucleotide linkages are
      phosphorothioates
<220> FEATURE:
<221> NAME/KEY: modified_base
<222> LOCATION: (1)..(1)
<223> OTHER INFORMATION: 2' OCH3 substitution

```
<220> FEATURE:
<221> NAME/KEY: modified_base
<222> LOCATION: (2)..(2)
<223> OTHER INFORMATION: 5-methyl substitution
<220> FEATURE:
<221> NAME/KEY: modified_base
<222> LOCATION: (3)..(3)
<223> OTHER INFORMATION: 2' OCH3 substitution
<220> FEATURE:
<221> NAME/KEY: modified_base
<222> LOCATION: (4)..(4)
<223> OTHER INFORMATION: 8-Fluoro substitution
<220> FEATURE:
<221> NAME/KEY: modified_base
<222> LOCATION: (5)..(6)
<223> OTHER INFORMATION: 6-Fluoro substitution
<220> FEATURE:
<221> NAME/KEY: modified_base
<222> LOCATION: (7)..(7)
<223> OTHER INFORMATION: 5-fluoro substitution
<220> FEATURE:
<221> NAME/KEY: modified_base
<222> LOCATION: (8)..(9)
<223> OTHER INFORMATION: 6-Fluoro substitution
<220> FEATURE:
<221> NAME/KEY: modified_base
<222> LOCATION: (10)..(10)
<223> OTHER INFORMATION: 5-methyl substitution
<220> FEATURE:
<221> NAME/KEY: modified_base
<222> LOCATION: (11)..(11)
<223> OTHER INFORMATION: 2' OCH3 substitution
<220> FEATURE:
<221> NAME/KEY: modified_base
<222> LOCATION: (12)..(12)
<223> OTHER INFORMATION: 2-Fluoro substitution
<220> FEATURE:
<221> NAME/KEY: modified_base
<222> LOCATION: (13)..(13)
<223> OTHER INFORMATION: 5-fluoro substitution
<220> FEATURE:
<221> NAME/KEY: modified_base
<222> LOCATION: (14)..(14)
<223> OTHER INFORMATION: Locked nucleic acid
<220> FEATURE:
<221> NAME/KEY: modified_base
<222> LOCATION: (14)..(14)
<223> OTHER INFORMATION: 6-Fluoro substitution
<220> FEATURE:
<221> NAME/KEY: modified_base
<222> LOCATION: (15)..(16)
<223> OTHER INFORMATION: 8-Fluoro substitution
<220> FEATURE:
<221> NAME/KEY: modified_base
<222> LOCATION: (17)..(17)
<223> OTHER INFORMATION: 5-fluoro substitution
<220> FEATURE:
<221> NAME/KEY: modified_base
<222> LOCATION: (18)..(18)
<223> OTHER INFORMATION: 2-Fluoro substitution
<220> FEATURE:
<221> NAME/KEY: modified_base
<222> LOCATION: (19)..(19)
<223> OTHER INFORMATION: 8-Fluoro substitution
<220> FEATURE:
<221> NAME/KEY: modified_base
<222> LOCATION: (20)..(20)
<223> OTHER INFORMATION: 5-fluoro substitution
<220> FEATURE:
<221> NAME/KEY: modified_base
<222> LOCATION: (21)..(22)
<223> OTHER INFORMATION: 2' OCH3 substitution

<400> SEQUENCE: 16
acaattcttc aactaacaac tt                                              22

<210> SEQ ID NO 17
```

```
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(18)
<223> OTHER INFORMATION: All internucleotide linkages are
      phosphorothioates
<220> FEATURE:
<221> NAME/KEY: modified_base
<222> LOCATION: (1)..(1)
<223> OTHER INFORMATION: Locked nucleic acid
<220> FEATURE:
<221> NAME/KEY: modified_base
<222> LOCATION: (1)..(1)
<223> OTHER INFORMATION: 5-methyl substitution
<220> FEATURE:
<221> NAME/KEY: modified_base
<222> LOCATION: (2)..(2)
<223> OTHER INFORMATION: Locked nucleic acid
<220> FEATURE:
<221> NAME/KEY: modified_base
<222> LOCATION: (4)..(4)
<223> OTHER INFORMATION: 2' OCH3 substitution
<220> FEATURE:
<221> NAME/KEY: modified_base
<222> LOCATION: (4)..(4)
<223> OTHER INFORMATION: 5-methyl substitution
<220> FEATURE:
<221> NAME/KEY: modified_base
<222> LOCATION: (7)..(7)
<223> OTHER INFORMATION: Locked nucleic acid
<220> FEATURE:
<221> NAME/KEY: modified_base
<222> LOCATION: (7)..(7)
<223> OTHER INFORMATION: 5-methyl substitution
<220> FEATURE:
<221> NAME/KEY: modified_base
<222> LOCATION: (10)..(10)
<223> OTHER INFORMATION: 2' OCH3 substitution and not methylated at the
      5 position
<220> FEATURE:
<221> NAME/KEY: modified_base
<222> LOCATION: (12)..(12)
<223> OTHER INFORMATION: Locked nucleic acid
<220> FEATURE:
<221> NAME/KEY: modified_base
<222> LOCATION: (14)..(14)
<223> OTHER INFORMATION: Locked nucleic acid
<220> FEATURE:
<221> NAME/KEY: modified_base
<222> LOCATION: (14)..(14)
<223> OTHER INFORMATION: 5-methyl substitution
<220> FEATURE:
<221> NAME/KEY: modified_base
<222> LOCATION: (15)..(15)
<223> OTHER INFORMATION: Locked nucleic acid
<220> FEATURE:
<221> NAME/KEY: modified_base
<222> LOCATION: (17)..(17)
<223> OTHER INFORMATION: Locked nucleic acid
<220> FEATURE:
<221> NAME/KEY: modified_base
<222> LOCATION: (17)..(17)
<223> OTHER INFORMATION: 5-methyl substitution
<220> FEATURE:
<221> NAME/KEY: modified_base
<222> LOCATION: (18)..(18)
<223> OTHER INFORMATION: Locked nucleic acid

<400> SEQUENCE: 17
cttcttcaac tggcagct                                                 18

<210> SEQ ID NO 18
<211> LENGTH: 18
```

```
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(18)
<223> OTHER INFORMATION: All internucleotide linkages are
      phosphorothioates
<220> FEATURE:
<221> NAME/KEY: modified_base
<222> LOCATION: (1)..(1)
<223> OTHER INFORMATION: Locked nucleic acid
<220> FEATURE:
<221> NAME/KEY: modified_base
<222> LOCATION: (1)..(1)
<223> OTHER INFORMATION: 5-methyl substitution
<220> FEATURE:
<221> NAME/KEY: modified_base
<222> LOCATION: (2)..(2)
<223> OTHER INFORMATION: Locked nucleic acid
<220> FEATURE:
<221> NAME/KEY: modified_base
<222> LOCATION: (4)..(4)
<223> OTHER INFORMATION: 2' OCH3 substitution and not methylated at the
      5 position
<220> FEATURE:
<221> NAME/KEY: modified_base
<222> LOCATION: (7)..(7)
<223> OTHER INFORMATION: Locked nucleic acid
<220> FEATURE:
<221> NAME/KEY: modified_base
<222> LOCATION: (7)..(7)
<223> OTHER INFORMATION: 5-methyl substitution
<220> FEATURE:
<221> NAME/KEY: modified_base
<222> LOCATION: (10)..(10)
<223> OTHER INFORMATION: 2' OCH3 substitution and not methylated at the
      5 position
<220> FEATURE:
<221> NAME/KEY: modified_base
<222> LOCATION: (12)..(12)
<223> OTHER INFORMATION: Locked nucleic acid
<220> FEATURE:
<221> NAME/KEY: modified_base
<222> LOCATION: (14)..(14)
<223> OTHER INFORMATION: Locked nucleic acid
<220> FEATURE:
<221> NAME/KEY: modified_base
<222> LOCATION: (14)..(14)
<223> OTHER INFORMATION: 5-methyl substitution
<220> FEATURE:
<221> NAME/KEY: modified_base
<222> LOCATION: (15)..(15)
<223> OTHER INFORMATION: Locked nucleic acid
<220> FEATURE:
<221> NAME/KEY: modified_base
<222> LOCATION: (17)..(17)
<223> OTHER INFORMATION: Locked nucleic acid
<220> FEATURE:
<221> NAME/KEY: modified_base
<222> LOCATION: (17)..(17)
<223> OTHER INFORMATION: 5-methyl substitution
<220> FEATURE:
<221> NAME/KEY: modified_base
<222> LOCATION: (18)..(18)
<223> OTHER INFORMATION: Locked nucleic acid
<220> FEATURE:
<221> NAME/KEY: modified_base
<222> LOCATION: (18)..(18)
<223> OTHER INFORMATION: 5-methyl substitution

<400> SEQUENCE: 18
cttcttcaac tggcagcc                                                 18
```